(12) United States Patent
Hackett et al.

(10) Patent No.: US 7,615,613 B2
(45) Date of Patent: *Nov. 10, 2009

(54) ANTIGEN CONSTRUCTS USEFUL IN THE DETECTION AND DIFFERENTIATION OF ANTIBODIES TO HIV

(75) Inventors: John R. Hackett, Libertyville, IL (US); Julie Yamaguchi, Chicago, IL (US); Alan M. Golden, Wilmette, IL (US); Catherine A. Brennan, Libertyville, IL (US); Robert K. Hickman, Mundelein, IL (US); Sushil G. Devare, Northbrook, IL (US)

(73) Assignee: Abbott Laboratories, Inc., Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/954,351

(22) Filed: Dec. 12, 2007

(65) Prior Publication Data

US 2008/0090994 A1    Apr. 17, 2008

Related U.S. Application Data

(62) Division of application No. 11/008,351, filed on Dec. 9, 2004, which is a division of application No. 08/911,824, filed on Aug. 15, 1997, now Pat. No. 6,846,905.

(51) Int. Cl.
    C07K 14/16    (2006.01)
(52) U.S. Cl. .................... 530/350; 530/300
(58) Field of Classification Search .......... None
    See application file for complete search history.

(56) References Cited

U.S. PATENT DOCUMENTS

| 4,946,778 | A | 8/1990 | Ladner et al. |
| 5,055,391 | A | 10/1991 | Montagnier et al. |
| 5,071,972 | A | 12/1991 | Larsen |
| 5,124,255 | A | 6/1992 | Bolling et al. |
| 5,254,458 | A | 10/1993 | Mimms |
| 5,304,466 | A | 4/1994 | De Leys et al. |
| 5,322,769 | A | 6/1994 | Bolling et al. |
| 6,153,377 | A * | 11/2000 | Devare et al. ............ 435/5 |
| 6,846,905 | B2 | 1/2005 | Hackett, Jr. et al. |

FOREIGN PATENT DOCUMENTS

| EP | 0212914 | 3/1987 |
| EP | 0273115 | 7/1988 |
| EP | 0276846 | 8/1988 |
| EP | 0317804 | 5/1989 |
| EP | 0326100 | 8/1989 |
| EP | 0370458 | 11/1989 |
| EP | 0347365 | 12/1989 |
| EP | 0406473 | 1/1991 |
| EP | 0424634 | 5/1991 |
| EP | 0425633 | 5/1991 |
| EP | 0473065 | 3/1992 |
| EP | 0591914 | 4/1994 |
| EP | 0617132 | 9/1994 |
| EP | 0727497 | 8/1996 |
| GB | 2188639 | 10/1997 |
| WO | 8912094 | 12/1989 |
| WO | 9107664 | 5/1991 |
| WO | 9400594 | 1/1994 |
| WO | 9523973 | 9/1995 |
| WO | 9532293 | 11/1995 |
| WO | 9612809 | 5/1996 |
| WO | 9909410 | 2/1999 |

OTHER PUBLICATIONS

EMBL X96526 from U.S. Appl. No. 08/911,824 dated Jan. 25, 2001.*
Rayfield et al Emerging Infectious Diseases 1996 vol. 2, pp. 209-212.*
EMBL and NCBI Accession No. X96526, sequence comparison sheet.
Delaporte et al., AIDS 1996, vol. 10, pp. 903-910.
Amino Acid Sequence Comparison dated Jan. 25, 2001 (one two-sided page).
Hampl, H. et al., "First case of HIV-1 subtype O infection in Germany", Infection, vol. 23, No. 6, Nov. 1995, pp. 369-370.
Kuhnel, H. et al., "Molecular cloning of two West African human immunodeficiency virus type 2 isolates that replicate well in macrophages: A Gambian isolate, from a patient with neuralgic acquired immunodeficiency syndrome, and a highly divergent Ghanian isolate", Proc. Natl. Acad Sci., USA, vol. 86, Apr. 1989, pp. 2383-2387.
Kuhnel, H. et al., "Nucleotide sequence of HIV-2 D194, an isolate from a Gambian case of 'Neuro-AIDS', which showed excellent growth in macrophages", Nucleic Acids Research, vol. 18, No. 20, Aug. 28, 1990, p. 6142.
Shoeman, R.L. et al., "Comparison of Recombinant Human Immunodeficiency Virus gag Precursor and gag/env Fusion Proteins and a Synthetic env Peptide as Diagnostic Reagents", Analytical Biochemistry, vol. 161, No. 2 (1987) pp. 370-379.
Yuan, Xin et al., "Human Immunodeficiency Virus vpr Gene Enclodes a Virion-Associated Protein", AIDS Research and Human Retroviruses, vol. 6, No. 11, (1990) pp. 1265-1271.

(Continued)

*Primary Examiner*—Mary E Mosher
*Assistant Examiner*—Myron G Hill
(74) *Attorney, Agent, or Firm*—Audrey L. Bartnicki; Lisa V. Mueller

(57) ABSTRACT

Isolated HIV-1 Group O env polypeptides obtained from the HIV-1 isolate HAM112 are claimed, as well as (a) antigen constructs comprising fusions of one or more of each of HIV-1 Group O env polypeptides and HIV-1 Group M env polypeptide and (b) further antigen constructs containing additional Group O sequences and especially the gp41 IDR of isolate HAM112. Also claimed are polynucleotide sequences encoding the above, expression vectors comprising the same, host cells transformed thereby, and immunoassay methods and kits utilizing the antigen constructs of the invention.

3 Claims, No Drawings

OTHER PUBLICATIONS

"Construction of Immunoglobulin Fusion Proteins", Current Protocols in Immunology, Supp. 4, pp. 10.19.1-10.19.11 (1992) John Wiley and Sons, New York, New York.

"The EBV-Hybridoma Technique and Its Application to Human Lung Cancer", S.P.C. Cole et al., Monoclonal Antibodies and Cancer Therapy, Alan R. Liss, Inc., New York, New York, pp. 77-96 (1985).

Human Retroviruses and AIDS 1995, G. Meyers et al., Los Alamos National Laboratory, Los Alamos, NM (1995) [Table of Contents (partial)].

J.D. Watson et al. (Eds.), molecular Biology of the Gene, fourth edition, Benjamin/Cummings Publishing Company, Inc., (1987), p. 440.

J. Sambrook et al., Molecular Cloning: A Laboratory Manual, second edition, Cold Spring Harbor Laboratory Press (1989).

P. Charneau et al., "Isolation and Envelope Sequence of a Highly Divergent HIV-1 Isolate: Definition of a New HIV-1 Group", Virology, vol. 205 (1994) pp. 247-253.

M. Vanden Haesevelde et al., "Genomic Cloning and Complete Sequence Analysis of a Highly Divergent African Human Immunodeficiency Virus Isolate", Journal of Virology, vol. 68, No. 3 (1994) pp. 1586-1596.

I. Loussert —Ajaka et al., "HIV-1/HIV-2 Seronegativity In HIV-1 Subtype O Infected Patients", Lancet, vol. 343, (1994) pp. 1393-1394.

L.G. Gurtler et al., "A New Subtype of Human Immunodeficiency Virus Typ 1 (MVP-5180) From Cameroon", Journal of Virology, vol. 68, No. 3 (1994) pp. 1581-1585.

R. De Leys et al., "Isolation and Partial characterization of an Unusual Human Immunodeficiency Retrovirus from Two Persons of West-Central African Origin", Journal of Virology, vol. 64, No. 3 (1990) pp. 1207-1216.

CDC, "AIDS Due to HIV-2 Infection-New Jersey", MMWR, vol. 39 (1987) pp. 33-35.

M.A. Rey et al., Lancet, vol. i, (1987) pp. 388-389.

A.G. Saimot et al., Lancet, vol. i, (1987) p. 688.

A. Werner et al., Lancet, vol. i (1987) pp. 868-869.

I. Loussert-Ajaka et al., "Variability of Human Immunodeficiency Virus Type 1 Group O Strains Isolated from Cameroonian Patients Livig in France", Journal of Virology, vol. 69, No. 9 (1995) pp. 5640-5649.

M. Peeters et al., "Geographical Distribution of Hiv-1 Group O Viruses in Africa", AIDS, vol. 11, (1997) pp. 493-498.

F. Denis et al., "Comparison of 10 Enzyme Immunoassays for Detection of Antibody to Human immunodeficiency Virus Type 2 in West African Sera", Journal of Clinical Microbiology, vol. 26, No. 5 (1988) p. 1000-1004.

W.H. Landschulz et al., "The Leucine Zipper: A Hypothetical Structure Common to a New Class of DNA Binding Proteins", Science, vol. 240 (1988) pp. 1759-1764.

H. Kuhnet et al., "Molecular Cloning of Two West African Human Immunodeficiency Virus Type 2 Isolates that Replicate Well in Macrophages . . .", Proceedings of the National Acad. Sci., vol. 86, (1989) pp. 2383-2387.

D. Kozbor et al., "The Production of Monoclonal Antibodies from Human Lymphocytes", Immunology Today, vol. 4, No. 3 (1983) pp. 72-79.

C. Schable et al., "Sensitivity of United States HIV Antibody Tests for Detection of HIV-1 Group O Infections", Lancet, vol. 344, (1994) pp. 1333-1334.

H. Kuhnet et al., "Nucleotide Sequence of HIV-2D194, an Isolate from a Gambian Case of 'Neuro-AIDS', Which Showed Excellent Growth in Macrophages", Nucleic Acids Research, vol. 18, No. 20 (1990) p. 6142.

M. Gouy et al., "Codon Usage in Bacteria: Correlation with Gene Expressivity", Nucleic Acids Research, vol. 10, No. 22 (1982) pp. 7055-7074.

L. Gurtler et al., "Reactivity of Five Anti-HIV-1 Subtype O Specimens with Six Different Anti-HIV Screening ELISA's and Three Immunoblots", Journal of Virological Methods, vol. 51 (1995), pp. 177-187.

V. Gluzman, "SV40-Transformed Simian Calls Support the Replication of Early SV40 Mutants", Cell, vol. 23 (1981), pp. 175-182.

I. Wilson et al., "The Structure of an Antigenic Determinant in a Protein", Cell, vol. 37 (1984) pp. 767-778.

H. Hampl et al., "First Case of HIV-1 Subtype O Infection in Germany", Infection, vol. 23 No. 6 (1995) pp. 369-370.

P.A. Price et al., "Propertied of Chromatography Purified Bovine Pancratic Deoxyribonuclease", The Journal of Biol. Chem., vol. 244 No. 4 (1969) p. 917-923.

H.U. Benard et al., "Construction of Plasmid Cloning Vehicles that Promote Gene Expression from the Bacteriophage Lambida pL Promoter", Gene, vol. 5 (1979) pp. 59-76.

H. Grosjean et al., "Preferential Codon Usage in Prokaryotic Genes: the Optimal Codon-Anticodon Interaction Energy and the Selective Codon in Efficiently Expressed Genes", Gene, vol. 18 (1982) pp. 199-209.

Kohler et al., "Continuous Cultures of Fused Cells Secreting Antibody f Predefined Specificity", Nature, vol. 256, (1975) pp. 495-497.

Anonymous, Nature, vol. 332 (1988) pp. 295.

A. Mas et al., "env Gene Characterization of the First HIV Type 1 Group O Spanish Isolate", AIDS Research and Human Retroviruses, vol. 12, No. 17 (1996) pp. 1647-1649.

M.A. Rayfield et al., "HIV-1 Group O Virus Identified for the First Time in the United States", Emerging Infectious Diseases, vol. 2 (1996) pp. 209-212.

F. Clavel, "HIV-2 the West African AIDS Virus", AIDS, vol. 1 (1987) pp. 135-140.

K. Marquart et al., "HIV-2 in West Germany", AIDS, vol. 2 (1988) p. 141.

G. Brucker et al., "HIV-2 Infection in Two Homosexual Men in France", Lancet, vol. i, (1987) p. 223.

L. Davis et al., Basic Methods in Molecular Biology, Elsevier Science Publishing Co., Inc., New York, NY (1986).

* cited by examiner

ANTIGEN CONSTRUCTS USEFUL IN THE DETECTION AND DIFFERENTIATION OF ANTIBODIES TO HIV

RELATED APPLICATION INFORMATION

This application is a divisional of U.S. patent application Ser. No. 11/008,351 filed on Dec. 9, 2004, which is a divisional of U.S. patent application Ser. No. 08/911,824 filed on Aug. 15, 1997, which is now U.S. Pat. No. 6,846,905.

BACKGROUND OF THE INVENTION

This invention relates generally to immunoassays for the detection and differentiation of antibodies to Human Immunodeficiency Virus Type 1 (HIV-1) Group M, HIV-1 Group O and Human Immunodeficiency Virus Type 2 (HIV-2). More particularly, the invention relates to novel antigen constructs useful as reagents in such assays, as well as polynucleotides, DNA clones, expression vectors, transformed host cells and the like which are useful in the preparation of such antigens.

Detection of HIV infection in a patient, and characterization of the viral type, are typically carried out using immunoassays which rely on the highly specific interaction between antigens used as reagents in the assay and circulating antibodies in the patient's serum. The immunoreactivity of patient antibodies with some antigens, and to a lesser extent or not at all with others, permits the identification of the type and subtype of the HIV which is present.

Currently, there are two major phylogenetic groups of HIV-1 designated as Groups "M" and "O." G. Meyers et al., *Human Retroviruses and AIDS* 1995, Los Alamos National Laboratory, Los Alamos, N. Mex. (1995). HIV-1 Group M isolates further have been divided into subgroups (A to J) that are phylogenetically approximately equidistant from each other. Group M isolates predominate worldwide. The earliest reports about the sequence of HIV-1 Group O indicated that these viruses were as closely related to a chimpanzee virus as to other HIV-1 subgroups. See, for example, L. G. Gürtler et al., *J. Virology* 68:1581-1585 (1994); M. Vanden Haesevelde et al., *J. Virology* 68:1586-1596 (1994); De Leys et al., *J. Virology* 64:1207-1216 (1990); DeLeys et al., U.S. Pat. No. 5,304,466; L. G. Gürtler et al., European Patent Publication No. 591914 A2. The Group O sequences are the most divergent of the HIV-1 sequences described to date. Although HIV-1 Group O strains are endemic to west central Africa (Cameroon, Equatorial Guinea, Nigeria and Gabon), patients infected with Group O isolates now have been identified in Belgium, France, Germany, Spain and the United States. See, for example, R. DeLeys et al., supra; P. Charneau et al., *Virology* 205:247-253 (1994); I. Loussert-Ajaka et al., *J. Virology* 69:5640-5649 (1995); H. Hampl et al., *Infection* 23:369-370 (1995); A. Mas et al., *AIDS Res. Hum. Retroviruses* 12:1647-1649 (1996); M. Peters et al., *AIDS* 11:493-498 (1997); and M. A. Rayfield et al., *Emerging Infectious Diseases* 2:209-212 (1996).

HIV-1 Group M serology is characterized in large part by the amino acid sequences of the expressed viral proteins (antigens), particularly those comprising the core and envelope (env) regions. As between various strains of this rapidly-mutating virus, these antigens are structurally and functionally similar but have divergent amino acid sequences which elicit antibodies that are similar but not identical in their specificity for a particular antigen.

One of the key serological targets for detection of HIV-1 infection is the 41,000 MW transmembrane protein (TMP), glycoprotein 41 (gp41). gp41 is a highly immunogenic protein which elicits a strong and sustained antibody response in individuals considered seropositive for HIV. Antibodies to this protein are among the first to appear at seroconversion. The immune response to gp41 apparently remains relatively strong throughout the course of the disease, as evidenced by the near universal presence of anti-gp41 antibodies in asymptomatic patients as well as those exhibiting clinical stages of AIDS. A significant proportion of the antibody response to gp41 is directed toward a well-characterized immunodominant region (IDR) within gp41.

Infections with HIV Type 2 (HIV-2), a virus initially found in individuals from Africa, now have been identified in humans outside of the initial endemic area of West Africa, and have been reported in Europeans who have lived in West Africa or those who have had sexual relations with individuals from this region. See, for example, A. G. Saimot et al., *Lancet* i:688 (1987); M. A. Rey et al., *Lancet* i:388-389 (1987); A. Werner et al., *Lancet* i:868-869 (1987); G. Brucker et al., *Lancet* i:223 (1987); K. Marquart et al., *AIDS* 2:141 (1988); CDC, MMWR 37:33-35 (1987); Anonymous, *Nature* 332:295 (1988). Cases of AIDS due to HIV-2 have been documented world-wide. Serologic studies indicate that while HIV-1 and HIV-2 share multiple common epitopes in their core antigens, the envelope glycoproteins of these two viruses are much less cross-reactive. F. Clavel, *AIDS* 1:135-140 (1987). This limited cross-reactivity of the envelope antigens is believed to explain why currently available serologic assays for HIV-1 may fail to react with certain sera from individuals with antibody to HIV-2. F. Denis et al., *J. Clin. Micro.* 26:1000-1004 (1988). Recently-issued U.S. Pat. No. 5,055,391 maps the HIV-2 genome and provides assays to detect the virus.

These viral strains are, for the most part, readily identified and characterized using commercially-available diagnostic tests. However, concerns have arisen regarding the capability of currently-available immunoassays, designed for the detection of antibody to HIV-1 (Group M) and/or HIV-2, to detect the presence of antibody to HIV-1 Group O. I Loussert-Ajaka et al., *Lancet* 343:1393-1394 (1994); C. A. Schable et al., *Lancet* 344:1333-1334 (1994); L. Gürtler et al., *J. Virol. Methods* 51:177-184 (1995). Although, to date, few patients outside of west Central Africa have been found to be infected with HIV-1 Group O isolates, health officials fear the emergence of this subtype in other geographic areas as well.

Consequently, there is a continued need for new antigens, suitable for use in immunoassays, which alone or in conjunction with other antigens permit the recognition of all HIV-1 (Group M and Group O) and HIV-2 isolates and/or infections.

SUMMARY OF THE INVENTION

It has now been found that certain polypeptides or combinations of are particularly useful in the detection of HIV-1 Group O and other HIV infections. Consequently, in a first aspect of the present invention is disclosed an isolated HIV-1 Group O env polypeptide having an amino acid sequence consisting essentially of the sequence of SEQ ID NO:61 representing the full-length env region of the HIV-1 Group O isolate HAM112. Similarly disclosed is an isolated HIV-1 Group O env polypeptide comprising an immunoreactive portion of the above full-length polypeptide, as well as polynucleotides encoding such polypeptides.

In a second aspect of the present invention, an antigen construct is disclosed which comprises a first HIV-1 Group O env polypeptide fused to a second HIV-1 Group O env polypeptide. Preferably, the first polypeptide of such an antigen construct is a gp120 polypeptide and the second polypeptide is a gp41 polypeptide, optionally with a portion of the hydrophobic region of the gp41 polypeptide being deleted so as to facilitate expression when expressed as a recombinant product. Also preferred among the above antigen constructs are those in which at least one of the first and second HIV-1 Group O env polypeptides is derived from HIV-1 Group O isolate HAM112, as are those in which the first polypeptide comprises an immunoreactive portion of the gp120 protein of HIV-1 Group O isolate HAM112.

In the above Group O env constructs, the first polypeptide may have an amino acid sequence which consists essentially of residues 1 through 520 of the sequence of SEQ ID NO:61, or alternatively an immunoreactive portion thereof. A shortened and preferred first polypeptide is one having an amino acid sequence consisting essentially of residues 476 through 520 of the sequence of SEQ ID NO:61. Along with any of the above polypeptides, the second polypeptide used in the constructs of the invention may be an immunoreactive portion of the gp41 protein of HIV-1 Group O isolate HAM112, from which a portion of the hydrophobic region of the gp41 protein of HIV-1 Group O isolate HAM112 is optionally absent. In particular, the deleted portion may be that part of gp41 which has an amino acid sequence consisting essentially of residues 690 through 715 of the sequence of SEQ ID NO:61.

The above second polypeptide will preferably have an amino acid sequence consisting essentially of residues 521 through 873 of the sequence of SEQ ID NO:61 or a portion thereof. More preferably, the second polypeptide may have an amino acid sequence consisting essentially of residues 47 through 373 of the sequence of SEQ ID NO:52; still more preferably, the amino acid sequence may consist essentially of residues 47 through 245 of the sequence of SEQ ID NO:48; and even more preferably, the amino acid sequence may consist essentially of residues 47 through 215 of the sequence of SEQ ID NO:58. Representative of the Group O env constructs of the invention are constructs pGO-8PL, pGO-8CKS, pGO-9PL, pGO-9CKS, pGO-11 PL and pGO-11CKS, as well as any derivatives, variants and analogs thereof.

In a further aspect of the present invention, there is disclosed an antigen construct comprising a fusion of at least one HIV-1 Group O env polypeptide with at least one HIV-1 Group M env polypeptide, and more preferably an antigen construct comprising a fusion of:

(a) a first HIV-1 Group O env polypeptide;

(b) a second HIV-1 Group O env polypeptide;

(c) a first HIV-1 Group M env polypeptide; and (d) a second HIV-1 Group M env polypeptide.

The HIV-1 Group M polypeptides in the above constructs may be derived from an HIV-1 isolate of Subtype B, and preferably at least one is derived from HIV-1 Group M isolate HXB2R. In any of these Group O/Group M env constructs, at least one of the HIV-1 Group O sequences may be derived from HIV-1 Group O isolate HAM112.

More particularly, the first Group O env polypeptide and the first Group M env polypeptide may both be gp120 polypeptides, while the second Group O env polypeptide and the second Group M env polypeptide may both be gp41 polypeptides. To enhance expression, a portion of the hydrophobic region of at least one of the gp41 polypeptides may be deleted. Antigen constructs included among the above are those in which:

(a) the first HIV-1 Group O env polypeptide comprises an immunoreactive portion of the gp120 protein of HIV-1 Group O isolate HAM112;

(b) the second HIV-1 Group O env polypeptide comprises an immunoreactive portion of the gp41 protein of HIV-1 Group O isolate HAM12

(c) the first HIV-1 Group M env polypeptide comprises an immunoreactive portion of the gp120 protein of a first HIV-1 Group M isolate of Subtype B; and (d) the second HIV-1 Group M env polypeptide comprises an immunoreactive portion of the gp41 protein of a second HIV-1 Group M isolate of Subtype B.

Preferred among these are constructs wherein the first and second HIV-1 Group M isolates of Subtype B are the same and are HIV-1 Group M isolate HXB2R, as well as those wherein a portion of the hydrophobic region of the gp41 protein of HIV-1 Group M isolate HXB2R is absent from the second HIV-1 Group M env polypeptide.

Preferred Group O/Group M env constructs include those in which (a) the first HIV-1 Group M env polypeptide has an amino acid sequence consisting essentially of residues 251 through 292 of the sequence of SEQ ID NO:108, and (b) the second HIV-1 Group M env polypeptide has an amino acid sequence consisting essentially of residues 293 through 599 of the sequence of SEQ ID NO:108 or a portion thereof. Especially preferred are those in which the second HIV-1 Group M env polypeptide has an amino acid sequence consisting essentially of residues 293 through 492 of the sequence of SEQ ID NO:108.

Also preferred are the above Group O/Group M env constructs in which the first HIV-1 Group O env polypeptide has an amino acid sequence consisting essentially of residues 1 through 520 of the sequence of SEQ ID NO:61 or a portion thereof, and especially those comprising a first HIV-1 Group O env polypeptide which has an amino acid sequence consisting essentially of residues 476 through 520 of the sequence of SEQ ID NO:61. The second HIV-1 Group O env polypeptide may be one having an amino acid sequence consisting essentially of residues 521 through 873 of the sequence of SEQ ID NO:61 or a portion thereof, from which a portion of the hydrophobic region of the gp41 protein of HIV-1 Group O isolate HAM112 may optionally be absent. Preferred constructs are those in which such second HIV-1 Group O env polypeptides have an amino acid sequence consisting essentially of residues 47 through 373 of the sequence of SEQ ID NO:52; more preferred are those in which the second HIV-1 Group O env polypeptide has an amino acid sequence consisting essentially of residues 47 through 245 of the sequence of SEQ ID NO:48; and even more preferred are those in which the second HIV-1 Group O env polypeptide has an amino acid sequence consisting essentially of residues 47 through 215 of the sequence of SEQ ID NO:58. Representative of the Group O/Group M env constructs of the invention are constructs pGO-12CKS, pGO-13CKS and pGO-14PL, and derivatives, variants and analogs thereof.

In yet another aspect of the present invention, an antigen construct is disclosed which comprises a fusion of a first HIV-1 env polypeptide, a second HIV-1 env polypeptide, and at least one additional HIV-1 polypeptide, and especially one in which each such HIV-1 env polypeptides are HIV-1 Group O polypeptides. The first HIV-1 Group O env polypeptide of this construct may be a gp120 polypeptide, and the second HIV-1 Group O env polypeptide a gp41 polypeptide. More particularly, the first HIV-1 Group O env polypeptide of this construct may comprise an immunoreactive portion of the gp120 protein of HIV-1 Group O isolate HAM112, while the second HIV-1 Group O env polypeptide may comprise an immunoreactive portion of the gp41 protein of HIV-1 Group O isolate HAM12.

Among these constructs, those in which the first HIV-1 Group O env polypeptide has an amino acid sequence consisting essentially of residues 1 through 520 of the sequence of SEQ ID NO:61, or a portion thereof, are preferred; more preferred are those in which the first HIV-1 Group O env polypeptide has an amino acid sequence consisting essentially of residues 476 through 520 of the sequence of SEQ ID NO:61. As to the second HIV-1 Group O env polypeptide, which may have an amino acid sequence consisting essentially of residues 521 through 873 of the sequence of SEQ ID NO:61 or a portion thereof and from which a portion of the hydrophobic region of the gp41 protein of HIV-1 Group O isolate HAM112 may optionally be absent, preferred are those constructs in which that second HIV-1 Group O env polypeptide has an amino acid sequence consisting essentially of residues 47 through 373 of the sequence of SEQ ID NO:52. Even more preferred are those having a second HIV-1 Group O env polypeptide with an amino acid sequence consisting essentially of residues 47 through 245 of the sequence of SEQ ID NO:48, and especially those in which the amino acid sequence consists essentially of residues 47 through 215 of the sequence of SEQ ID NO:58.

The additional HIV-1 polypeptide in any of these constructs may be a Group O env polypeptide; however, it is intended that it may alternatively be an immunogenic polypeptide from any of HIV-1 Groups M or O or HIV-2, including env, gag, pol, reverse transcriptase, and regulatory and other viral components. Preferred in any case are those constructs in which the additional HIV-1 Group O polypeptide comprises an immunoreactive portion of the gp41 protein of HIV-1 Group O isolate HAM112. Also preferred are those wherein the additional HIV-1 Group O polypeptide has an amino acid sequence consisting essentially of residues 521 through 873 of the sequence of SEQ ID NO:61 or a portion thereof, from which the hydrophobic region of the gp41 protein of HIV-1 Group O isolate HAM112 may optionally be absent. Even more preferred are constructs in which the additional HIV-1 Group O env polypeptide has an amino acid sequence consisting essentially of residues 47 through 373 of the sequence of SEQ ID NO:52; particularly preferred are those in which the additional HIV-1 Group O env polypeptide has an amino acid sequence consisting essentially of residues 47 through 245 of the sequence of SEQ ID NO:48, and especially those wherein the additional HIV-1 Group O env polypeptide has an amino acid sequence consisting essentially of residues 47 through 215 of the sequence of SEQ ID NO:58. Most preferred are constructs having as the additional HIV-1 Group O env polypeptide the so-called immunodominant region (IDR) of HIV-1 Group O, which has an amino acid sequence consisting essentially of residues 250 through 281 of the sequence of SEQ ID NO:120. Representative of the above constructs are pGO-15CKS and pGO-15PL, as well as any derivatives, variants and analogs thereof.

In still another aspect of the present invention is disclosed an antigen construct comprising a first HIV-2 env polypeptide fused to a second HIV-2 env polypeptide, and especially one in which the first HIV-2 env polypeptide is a gp120 polypeptide and the second HIV-2 env polypeptide is a gp36 polypeptide. Preferred among the such constructs are those in which:

(a) the first HIV-2 env polypeptide has an amino acid sequence consisting essentially of residues 248 through 307 of the sequence of SEQ ID NO:55 or a portion thereof; and (b) the second HIV-2 env polypeptide has an amino acid sequence consisting essentially of residues 308 through 466 of the sequence of SEQ ID NO:55 or a portion thereof.

Representative of the HIV-2 constructs of the invention is pHIV-210 (SEQ ID NO:55), as well as any derivatives, variants and analogs thereof.

An additional aspect of the present invention comprises polynucleotides encoding any of the above antigen construct, which polynucleotide may be operably linked to a control sequence capable of directing expression in a suitable host and/or have a coding sequence which has been modified to provide a codon bias appropriate to the expression host. Still other aspects of the present invention include expression vectors comprising such polynucleotides and host cells transformed thereby, particularly where the host is *Escherichia coli*.

In a further aspect of the present invention, there is disclosed a method for detecting antibodies to HIV-1 in a test sample comprising the steps of:

(a) combining at least one antigen construct according to the invention with the test sample to form a mixture;

(b) incubating the mixture under conditions suitable for formation of complexes between the antigen and antibodies, if any, which are present in the sample and are immunologically reactive with the antigen; and (c) detecting the presence of any complexes formed.

In one embodiment of the method, detection of the presence of complexes in step (c) is carried out using an additional antigen construct of the invention to which a signal-generating compound has been attached. In another embodiment, detection is carried out using an additional antigen construct of the invention to which a first member of a specific binding pair is attached, and further using an indicator reagent comprising a second member of the specific binding pair to which is attached a signal-generating compound. A further embodiment provides that detection of the presence of complexes in step (c) is carried out using an antibody directed to the complexes formed in step (b), to which antibody is attached a signal-generating compound. Still another embodiment provides that detection of the presence of complexes in step (c) is carried out using an antibody directed to the complexes formed in step (b) and attached thereto a first member of a specific binding pair; such detection further requires the use of an indicator reagent comprising a second member of the specific binding pair to which is attached a signal-generating compound.

In a final aspect of the present invention are disclosed immunoassay kits for the detection of antibodies to HIV-1, which kits comprise an antigen construct of the invention. Such construct may be used as a capture reagent or an indicator reagent. Alternatively, the antigen construct may be attached to a first member of a specific binding pair, the kit additionally comprising an indicator reagent comprising a second member of the specific binding pair attached to a signal-generating compound.

DETAILED DESCRIPTION OF THE INVENTION

In one embodiment of an isolated polypeptide of the present invention, the amino acid sequence of the env protein of the HIV-1 Group O isolate HAM112 is shown as SEQ ID NO:61. In the present context, "isolated" is intended to mean that such polypeptides are relatively purified with respect to other viral or cellular components which normally would be present in situ, up to and including a substantially pure preparation of the protein. Such polypeptides can be utilized as assay reagents, for the production of monoclonal or polyclonal antibodies, in the manufacture of vaccines, or otherwise.

Immunoreactive portions, or fragments, of the above polypeptides are also expected to be useful. By "immunoreactive" is meant portions of such length as are capable of eliciting an immune response in a host and/or of reacting with antibodies directed specifically thereto; preferably, such partial polypeptides will be five or more amino acids in length. It should also be noted that the term "portion" as used herein is directed to both terminally truncated sequences and those which are shortened by the removal of an intervening sequence.

The above polypeptides and portions will best be produced by expression of polynucleotides encoding the same. These too permit a degree of variability in their sequence, as for example due to degeneracy of the genetic code, codon bias in favor of the host cell expressing the polypeptide, and conservative amino acid substitutions in the resulting protein. Moreover, it is anticipated that some variation of sequences will occur between—and possibly even within—a given HIV-1 isolate or other phylogenetic unit. Consequently, the polypeptides and constructs of the invention include not only those which are identical in sequence to the above sequence but also those which have an amino acid sequence that consist essentially of that reference sequence, where the term "consisting essentially" is meant to embrace variant polypeptides the structural and functional characteristics of which remain substantially the same. Preferably, such variants (or "analogs") will have a sequence homology ("identity") of 80% or more with the reference sequence of SEQ ID NO:61. In this sense, techniques for determining amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known in the art.

According to another embodiment of the invention, antigen constructs are provided which are suitable for use in the detection of anti-HIV-1 antibodies. As described in greater detail below, such constructs may be prepared by recombinant means, as synthetic peptides, or otherwise; moreover, they may be glycosylated or unglycosylated depending on the manner and/or host cell by which they are made. Consequently, although referred to as if comprising glycoproteins (for example, "a gp120 polypeptide"), the antigen constructs of the invention are intended to include those which are expressed in bacterial hosts such as E. coli and are therefore unglycosylated.

It should be noted that the above constructs are fusions of various sequences, that is, the constructs are formed by joining various epitope-containing sequences, as for example by co-expression, ligation or sequential synthesis. Also joined thereto, and optionally included in the constructs of the invention, are other polypeptide sequences such as expression (CKS) polylinkers and other linker sequences. The order of the various polypeptide sequences is not critical; consequently, the polypeptides and their epitopes may be re-arranged as a matter of convenience. Further modifications are also possible, as for example by random mutation or site-directed mutagenesis or even the deletion (removal or omission) of certain regions such as the gp41 hydrophobic region, the absence of which has been found to enhance expression of the remaining polypeptide. In any case, whether nearly the same or substantially changed, polypeptides which undergo these modifications may be said to be "derived" from their respective sources, and the resulting polypeptides may be regarded as "derivatives".

In yet another aspect of the present invention, assay methods are provided which utilize the constructs of the invention in the detection of anti-HIV-1 antibodies in test samples. Such methods permit the direct testing of biological specimens; however, the assay methods may also be modified to permit the testing of pre-processed specimens such as sera, lysed cells, and extracts or preparations made therefrom (as by concentration, dilution, separation, fixation and/or immobilization). Depending on the desired assay format, the antigen constructs may also be modified for use in such assays, as for example by labeling, immobilization on a solid phase or otherwise, or conjugation to other assay reagents.

Certain terms used herein are intended to have specialized meanings. Unless otherwise stated, the terms below shall have the following meanings: The term "primer" denotes a specific oligonucleotide sequence complementary to a target nucleotide sequence and used to hybridize to the target nucleotide sequence. It serves as an initiation point for nucleotide polymerization catalyzed by either DNA polymerase, RNA polymerase or reverse transcriptase.

The term "polynucleotide" as used herein means a polymeric form of nucleotides of any length, either ribonucleotides or deoxyribonucleotides. This term refers only to the primary structure of the molecule. Thus, the term includes double- and single-stranded DNA as well as double- and single-stranded RNA. It also includes modifications, such as methylation or capping, and unmodified forms of the polynucleotide.

"Encoded by" refers to a nucleic acid sequence which codes for a polypeptide sequence. Also encompassed are polypeptide sequences which are immunologically identifiable with a polypeptide encoded by the sequence. Thus, a "polypeptide," "protein," or "amino acid" sequence as claimed herein may have at least 60% similarity, more preferably at least about 70% similarity, and most preferably about 80% similarity to a particular polypeptide or amino acid sequence specified below.

The terms "recombinant polypeptide" or "recombinant protein", used interchangeably herein, describe a polypeptide which by virtue of its origin or manipulation is not associated with all or a portion of the polypeptide with which it is associated in nature and/or is linked to a polypeptide other than that to which it is linked in nature. A recombinant or encoded polypeptide or protein is not necessarily translated from a designated nucleic acid sequence. It also may be generated in any manner, including chemical synthesis or expression of a recombinant expression system.

"Polypeptide" and "protein" are used interchangeably herein and indicate a molecular chain of amino acids linked through covalent and/or noncovalent bonds. The terms do not refer to a specific length of the product. Thus, peptides, oligopeptides and proteins are included within the definition of polypeptide. The terms include post-expression modifications of the polypeptide, for example, glycosylations, acetylations, phosphorylations and the like. In addition, protein fragments, analogs, mutated or variant proteins, fusion proteins and the like are included within the meaning of polypeptide.

A "fragment" of a specified polypeptide refers to an amino acid sequence which comprises at least about 3-5 amino acids, more preferably at least about 8-10 amino acids, and even more preferably at least about 15-20 amino acids, derived from the specified polypeptide.

The term "synthetic peptide" as used herein means a polymeric form of amino acids of any length, which may be chemically synthesized by methods well-known to those skilled in the art. These synthetic peptides are useful in various applications.

"Purified polypeptide" means a polypeptide of interest or fragment thereof which is essentially free, that is, contains less than about 50%, preferably less than about 70%, and more preferably, less than about 90% of cellular components with which the polypeptide of interest is naturally associated. Methods for purifying are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon to which another polynucleotide segment is attached, such as to bring about the replication and/or expression of the attached segment.

The term "control sequence" refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

A "coding sequence" is a polynucleotide sequence which is transcribed into mRNA and translated into a polypeptide when placed under the control of appropriate regulatory sequences. The boundaries of the coding sequence are determined by and include a translation start codon at the 5'-terminus and one or more translation stop codons at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the skilled artisan and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens.

"Purified product" refers to a preparation of the product which has been isolated from the cellular constituents with which the product is normally associated, and from other types of cells which may be present in the sample of interest.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. "Specific binding member" as used herein means a member of a specific binding pair. That is, two different molecules where one of the molecules through chemical or physical means specifically binds to the second molecule. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to polypeptide of interest as in a sandwich assay, to the capture reagent as in a competitive assay, or to the ancillary specific binding member as in an indirect assay.

The various "signal-generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (red blood cells "fixed" by pyruvic aldehyde and formaldehyde, available from Abbott Laboratories, Abbott Park, Ill.) and others.

The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

The present invention provides polynucleotide sequences derived from human immunodeficiency viruses of interest and polypeptides encoded thereby. The polynucleotide(s) may be in the form of mRNA or DNA. Polynucleotides in the form of DNA, cDNA, genomic DNA, and synthetic DNA are within the scope of the present invention. The DNA may be double-stranded or single-stranded, and if single stranded may be the coding (sense) strand or non-coding (anti-sense) strand. The coding sequence which encodes the polypeptide may be identical to the coding sequence provided herein or may be a different coding sequence which coding sequence, as a result of the redundancy or degeneracy of the genetic code, encodes the same polypeptide as the DNA provided herein.

This polynucleotide may include only the coding sequence for the polypeptide, or the coding sequence for the polypeptide and additional coding sequence such as a leader or secretory sequence or a proprotein sequence, or the coding sequence for the polypeptide (and optionally additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence which is a naturally-occurring variant of the coding sequence provided herein.

In addition, the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the form of the polypeptide. The polynucleotides may also encode for a proprotein which is the protein plus additional 5' amino acid residues. A protein having a prosequence is a proprotein and may in some cases be an inactive form of the protein. Once the prosequence is cleaved an active protein remains. Thus, the polynucleotide of the present invention may encode for a protein, or for a protein having a prosequence or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein. See, for example, I. Wilson et al., Cell 37:767 (1984).

The present invention further relates to HIV-1 polypeptides which have the deduced amino acid sequence as provided herein, as well as fragments, analogs and derivatives of such polypeptides. The polypeptides of the present invention may be recombinant polypeptides, natural purified polypeptides or synthetic polypeptides. The fragment, derivative or analog of such a polypeptide may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence which is employed for purification of the polypeptide or a proprotein sequence. Such fragments, derivatives and analogs are within the scope of the present invention. The polypeptides and polynucleotides of the present invention are preferably provided in an isolated form, and preferably purified.

Thus, a polypeptide of the present invention may have an amino acid sequence that is identical to that of the naturally-occurring polypeptide or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine. In contrast, variations may include nonconservative changes, e.g., replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

The recombinant polypeptides of the present invention can be produced not only as demonstrated below, but also according to a number of alternative methods and using a variety of host cells and expression vectors. Host cells are genetically engineered (transduced or transformed or transfected) with the vectors of this invention which may be a cloning vector or an expression vector. The vector may be in the form of a plasmid, a viral particle, a phage, etc. The engineered host cells can be cultured in conventional nutrient media modified as appropriate for activating promoters, selecting transformants or amplifying HIV-derived genes. The culture conditions, such as temperature, pH and the like, are those previously used with the host cell selected for expression, and will be apparent to the ordinarily skilled artisan.

The polynucleotides of the present invention may be employed for producing a polypeptide by recombinant techniques. Thus, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include but are not limited to LTR or SV40 promoter, the *E. coli* lac or trp, the phage lambda P sub L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli, Salmonella typhimurium; Streptomyces* sp.; fungal cells, such as yeast; insect cells such as *Drosophila* and Sf9; animal cells such as chinese hamster ovary (CHO), COS or Bowes melanoma;

plant cells, etc. The selection of an appropriate host is deemed to be within the scope of those skilled in the art from the teachings provided herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retrovirus, and mouse metallothionein-I. Selection of the appropriate vector and promoter is well within the level of ordinary skill in the art.

The host cell used herein can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (L. Davis et al., "Basic Methods in Molecular Biology", 2nd edition, Appleton and Lang, Paramount Publishing, East Norwalk, Conn. [1994]).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeast, bacteria, or other cells under the control of appropriate promoters. Cell-free translation systems also can be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, (Cold Spring Harbor, N.Y., 1989), which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and the *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well-known to the ordinary artisan.

Various mammalian cell culture systems can also be employed to express recombinant protein. Examples of mammalian expression systems include the COS-7 lines of monkey kidney fibroblasts described by Gluzman, *Cell* 23:175 (1981), and other cell lines capable of expressing a compatible vector, such as the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, 5' flanking nontranscribed sequences, and selectable markers such as the neomycin phosphotransferase gene. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

The HIV-derived polypeptides are recovered and purified from recombinant cell cultures by known methods including ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1-5 mM) of calcium ion present during purification (Price et al., *J. Biol. Chem.* 244:917 [1969]). Protein refolding steps can be used, as necessary, in completing configuration of the protein. Finally, high performance liquid chromatography (HPLC) can be employed for final purification steps.

The polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue.

The present invention further includes modified versions of the recombinant polypeptide to preclude glycosylation while allowing expression of a reduced carbohydrate form of the protein in yeast, insect or mammalian expression systems. Known methods for inactivating gylcosylation sites include, but are not limited to, those presented in U.S. Pat. No. 5,071,972 and EP 276,846, which are incorporated herein by reference.

Other variants included in the present invention include those obtained by removal removal of sequences encoding cystein residues, thereby preventing formation of incorrect intramolecular disulfide bridges which decrease biological activity of the protein product. The constructs of the present invention also may be prepared by removal of the site of proteolytic processing, allowing expression in systems which contain a problematic protease, for example the KEX2 protease in yeast. Known methods for removing such protease sites include but are not limited to one method for removing KEX2 sites presented in EP212,914.

The present invention includes the above peptides in the form of oligomers, dimers, trimers and higher order oligomers. Oligomers may be formed by several means including but not limited to disulfide bonds between peptides, non-covalent interactions between peptides, and poly-ethyleneglycol linkages between peptides.

The fusion of the above peptides to peptide linkers or peptides that are capable of promoting oligomers is also encompassed in this invention. Such peptides include but are not limited to leucine zippers and antibody derived peptides, such as is described in Landschulz et al., *Science* 240:1759 (1988); Hollenbaugh and Aruffo, "Construction of Immunoglobin Fusion Proteins", in *Current Protocols in Immunology, Supplement* 4, pgs 10.19.1-10.19.11 (1992) John Wiley and sons, New York, N.Y.

The starting plasmids can be constructed from available plasmids in accord with published, known procedures. In addition, equivalent plasmids to those described are known in the art and will be apparent to the ordinarily skilled artisan.

Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transformation of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

It is also contemplated and within the scope of the present invention that the above recombinant antigens will be used in a variety of immunoassay formats, including but not limited to direct and indirect assays. The means for adapting the antigens to such various formats—as by conjugation to labels or macromolecules, or immobilization on suitable support surfaces—are well-understood and should be familiar to those skilled in the art.

For example, the polypeptides including their fragments or derivatives or analogs thereof of the present invention, or cells expressing them, can be used for the detection of antibodies to HIV (as well as an immunogen to produce antibodies). These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

Further, antibodies generated against a polypeptide corresponding to a sequence of the present invention can be obtained by direct injection of the polypeptide into an animal or by administering the polypeptide to an animal such as a mouse, rabbit, goat or human. A mouse, rabbit or goat is preferred. The antibody so obtained then will bind the polypeptide itself. In this manner, even a sequence encoding only a fragment of the polypeptide can be used to generate antibodies that bind the native polypeptide. Such antibodies can then be used to isolate the polypeptide from test samples such as tissue suspected of containing that polypeptide. For preparation of monoclonal antibodies, any technique which provides antibodies produced by continuous cell line cultures can be used. Examples include the hybridoma technique as described by Kohler and Milstein, *Nature* 256:495-497 (1975), the trioma technique, the human B-cell hybridoma technique as described by Kozbor et al, *Immun. Today* 4:72 (1983), and the EBV-hybridoma technique to produce human monoclonal antibodies as described by Cole et al., in *Monoclonal Antibodies and Cancer Therapy*, Alan R. Liss, Inc, New York, N.Y., pp. 77-96 (1985). Techniques described for the production of single chain antibodies can be adapted to produce single chain antibodies to immunogenic polypeptide products of this invention. See, for example, U.S. Pat. No. 4,946,778, which is incorporated herein by reference.

Various assay formats may utilize such antibodies, including "sandwich" immunoassays and probe assays. For example, the monoclonal antibodies or fragment as described above can be employed in various assay systems to determine the presence, if any, of HIV-derived polypeptide in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of an HIV-derived polypeptide antigen present in the test sample and captured on the solid phase, if any, is determined by detecting the measurable signal generated by the signal generating compound. The amount of HIV-derived polypeptide antigen present in the test sample is proportional to the signal generated.

Or, a polyclonal or monoclonal HIV-derived polypeptide antibody or fragment thereof, or a combination of these antibodies which is bound to a solid support, the test sample and an indicator reagent comprising a monoclonal or polyclonal antibody or fragments thereof, which specifically binds to HIV-derived polypeptide antigen, or a combination of these antibodies to which a signal generating compound is attached, are contacted to form a mixture. This mixture is incubated for a time and under conditions sufficient to form antibody/antigen/antibody complexes. The presence, if any, of HIV-derived polypeptide present in the test sample and captured on the solid phase is determined by detecting the measurable signal generated by the signal generating compound. The amount of HIV-derived polypeptide proteins present in the test sample is proportional to the signal generated.

In another assay format, one or a combination of at least two monoclonal antibodies can be employed as a competitive probe for the detection of antibodies to HIV-derived polypeptide protein. For example, HIV-derived polypeptide proteins such as the recombinant antigens disclosed herein, either alone or in combination, are coated on a solid phase. A test sample suspected of containing antibody to HIV-derived polypeptide antigen then is incubated with an indicator reagent comprising a signal generating compound and at least one monoclonal antibody for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, each of the monoclonal or polyclonal antibodies can be employed in the detection of HIV-derived polypeptide antigens in fixed tissue sections, as well as fixed cells by immunohistochemical analysis. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) may be used to track the histopathology of disease.

In addition, these monoclonal antibodies can be bound to matrices similar to CNBr-activated Sepharose and used for the affinity purification of specific HIV-derived polypeptide proteins from cell cultures or biological tissues such as to purify recombinant and native HIV-derived polypeptide antigens and proteins.

Monoclonal antibodies can also be used for the generation of chimeric antibodies for therapeutic use, or other similar applications.

The monoclonal antibodies or fragments thereof can be provided individually to detect HIV-derived polypeptide antigens. Combinations of the monoclonal antibodies (and fragments thereof) also may be used together as components in a mixture or "cocktail" of at least one HIV-derived polypeptide antibody with antibodies to other HIV-derived polypeptide regions, each having different binding specificities. Thus, this cocktail can include monoclonal antibodies which are directed to HIV-derived polypeptide proteins of HIV and other monoclonal antibodies to other antigenic determinants of the HIV-derived polypeptide genome.

The polyclonal antibody or fragment thereof which can be used in the assay formats should specifically bind to an HIV-derived polypeptide region or other HIV-derived polypeptide proteins used in the assay. The polyclonal antibody used preferably is of mammalian origin; human, goat, rabbit or sheep anti-HIV-derived polypeptide polyclonal antibody can be used. Most preferably, the polyclonal antibody is rabbit polyclonal anti-HIV-derived polypeptide antibody. The polyclonal antibodies used in the assays can be used either alone or as a cocktail of polyclonal antibodies. Since the cocktails used in the assay formats are comprised of either monoclonal antibodies or polyclonal antibodies having different HIV-derived polypeptide specificity, they would be useful for diagnosis, evaluation and prognosis of HIV-derived polypeptide condition, as well as for studying HIV-derived polypeptide protein differentiation and specificity.

It is contemplated and within the scope of the present invention that HIV-derived polypeptides may be detectable in assays by use of recombinant antigens as well as by use of synthetic peptides or purified peptides, which contain amino acid sequences of HIV-derived polypeptides. It also is within the scope of the present invention that different synthetic, recombinant or purified peptides identifying different epitopes of each such HIV-derived polypeptide can be used in combination in an assay to diagnose, evaluate, or prognosticate the HIV disease condition. In this case, these peptides can be coated onto one solid phase, or each separate peptide may be coated on separate solid phases, such as microparticles, and then combined to form a mixture of peptides which can be later used in assays. Furthermore, it is contemplated that multiple peptides which define epitopes from different polypeptides may be used in combination to make a diagnosis, evaluation, or prognosis of HIV disease. Peptides coated on solid phases or labeled with detectable labels are then allowed to compete with peptides from a patient sample for a limited amount of antibody. A reduction in binding of the synthetic, recombinant, or purified peptides to the antibody (or antibodies) is an indication of the presence of HIV-secreted polypeptides in the patient sample which in turn indicates the presence of HIV gene in the patient. Such variations of assay formats are known to those of ordinary skill in the art and are discussed herein below.

In another assay format, the presence of antigens and/or antibodies to HIV-derived polypeptides can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens may be utilized as well as monoclonal antibodies produced therefrom. Such assay systems are described in greater detail in EP Publication No. 0473065.

In yet other assay formats, the polypeptides disclosed herein may be utilized to detect the presence of antibodies specific for HIV-derived polypeptides in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of HIV-derived polypeptide antibody. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from the same source or, alternatively, a second source different from the first source. For example, a recombinant protein derived from a first source such as *E. coli* is used as a capture antigen on a solid phase, a test sample is added to the so-prepared solid phase, and a recombinant protein derived from a different source (i.e., non-*E. coli*) is utilized as a part of an indicator reagent. Likewise, combinations of a recombinant antigen on a solid phase and synthetic peptide in the indicator phase also are possible. Any assay format which utilizes an antigen specific for HIV-derived polypeptide from a first source as the capture antigen and an antigen specific for HIV-derived polypeptide from a second source are contemplated. Thus, various combinations of recombinant antigens, as well as the use of synthetic peptides, purified proteins, and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication 0326100 and EP publication No. 0406473), can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

The present invention will be better understood in connection with the following examples, which are meant to illustrate, but not to limit, the spirit and scope of the invention.

Example 1

Cloning Procedures

Oligonucleotides for gene construction and sequencing were synthesized at Abbott Laboratories, Synthetic Genetics (San Diego, Calif.) or Oligo Etc. (Wilsonville, Calif.). All polymerase chain reaction (PCR) reagents, including AmpliTaq DNA polymerase and UITma DNA polymerase, were purchased from Perkin-Elmer Corporation (Foster City, Calif.) and used according to the manufacturer's specifications unless otherwise indicated. PCR amplifications were performed on a GeneAmp 9600 thermal cycler (Perkin-Elmer). Unless indicated otherwise, restriction enzymes were purchased from New England BioLabs (Beverly, Mass.) and digests were performed as recommended by the manufacturer. DNA fragments used for cloning were isolated on agarose (Life Technologies, Gaithersburg, Md.) gels, unless otherwise indicated.

Desired fragments were excised and the DNA was extracted with a QIAEX II gel extraction kit or the QIAquick gel extraction kit (Qiagen Inc., Chatsworth, Calif.) as recommended by the manufacturer. DNA was resuspended in $H_2O$ or TE [1 mM ethylenediaminetetraacetic acid (EDTA; pH 8.0; BRL Life Technologies), 10 mM tris(hydroxymethyl) aminomethane-hydrochloride (Tris-HCl; pH 8.0; BRL Life Technologies)]. Ligations were performed using a Stratagene DNA ligation kit (Stratagene Cloning Systems, La Jolla, Calif.) as recommended by the manufacturer. Ligations were incubated at 16° C. overnight.

Bacterial transformations were performed using MAX EFFICIENCY DH5α competent cells (BRL Life Technologies) or Epicurian Coli XL1-Blue supercompetent cells (Stratagene Cloning Systems) following the manufacturer's protocols. Unless indicated otherwise, transformations and bacterial restreaks were plated on LB agar (Lennox) plates with 150 g/ml ampicillin (M1090; MicroDiagnostics, Lombard, Ill.) or on LB agar+ampicillin plates supplemented with glucose to a final concentration of 20 mM, as noted. All bacterial incubations (plates and overnight cultures) were conducted overnight (~16 hours) at 37° C.

Screening of transformants to identify desired clones was accomplished by sequencing of miniprep DNA and/or by colony PCR. Miniprep DNA was prepared with a Qiagen Tip 20 Plasmid Prep Kit or a Qiagen QIAwell 8 Plasmid Prep Kit following the manufacturer's specifications, unless otherwise indicated. For colony PCR screening, individual colonies were picked from transformation plates and transferred into a well in a sterile flat-bottom 96-well plate (Costar, Cambridge, Mass.) containing 100 μl sterile $H_2O$. One-third of the volume was transferred to a second plate and stored at 4° C. The original 96-well plate was microwaved for 5 minutes to disrupt the cells. 1 μl volume then was transferred to a PCR tube as template. 9 μl of a PCR master mix containing 1 μl 10×PCR buffer, 1 μl 2 mM dNTPs, 1 μl (10 pmol) sense primer, 1 μl (10 pmol) anti-sense primer, 0.08 μl AmpliTaq DNA polymerase (0.4 units), and 4.2 μl $H_2O$ was added to the PCR tube. Reactions were generally amplified for 20-25 cycles of 94° C. for 30 seconds, 50-60° C. (depending on primer annealing temperatures) for 30 seconds and 72° C. for 60 seconds. Primers were dependent on the insert and cycle conditions were modified based on primer annealing temperatures and the length of the expected product. After cycling, approximately ⅓ of the reaction volume was loaded on an agarose gel for analysis. Colonies containing desired clones were propagated from the transfer plate.

Unless otherwise indicated, DNA sequencing was performed on an automated ABI Model 373A Stretch Sequencer (Perkin Elmer). Sequencing reactions were set up with reagents from a FS TACS Dye Term Ready Reaction Kit (Perkin Elmer) and 250-500 ng plasmid DNA according to the manufacturer's specifications. Reactions were processed on Centri-Sep columns (Princeton Separations, Adelphia, N.J.) prior to loading on the Sequencer. Sequence data was analyzed using Sequencher 3.0 (Gene Codes Corporation, Ann Arbor, Mich.) and GeneWorks 2.45 (Oxford Molecular Group, Inc., Campbell, Calif.).

Example 2

Determination of the env Sequence of the HIV-1 Group O Isolate HAM112

Viral RNA was extracted from culture supernatants of human peripheral blood mononuclear cells infected with the HIV-1 Group O isolate designated HAM112 (H. Hampl et al., *Infection* 23:369-370 [1995]) using a QIAamp Blood Kit (Qiagen) and the manufacturer's recommended procedure. RNA was eluted in a 50 μl volume of nuclease-free water (5Prime-3Prime, Inc., Boulder, Colo.) and stored at −70° C. The strategy for obtaining the env region sequence involved cDNA synthesis and PCR (nested) amplification of four overlapping env gene fragments. The amplified products were sequenced directly on an automated ABI Model 373A Stretch Sequencer. Amplification reactions were carried out with GeneAmp RNA PCR and GeneAmp PCR Kits (Perkin Elmer) as outlined by the manufacturer. Oligonucleotide primer positions correspond to the HIV-1 ANT70 env sequence (G. Myers et al., eds., supra). The primers env10R [nucleotide (nt) 791-772; SEQ ID NO:62], env15R (nt 1592-1574; SEQ ID NO:63), env22R (nt 2321-2302; SEQ ID NO:64), env26R (nt 250-232 3' of env; SEQ ID NO:65) were used for cDNA synthesis of fragments 1-4, respectively. Reverse transcription reactions were incubated at 42° C. for 30 minutes then at 99° C. for 5 minutes. First-round PCR amplifications consisted of 30 cycles of 95° C. for 30 seconds, 52° C. for 30 seconds, and 72° C. for 1 minute using the primer combinations: env1F (nt 184-166 5' of env; SEQ ID NO:66) and env10R (SEQ ID NO:62), env7F (nt 564-586; SEQ ID NO:67) and env15R (SEQ ID NO:63), env12F (nt 1289-1308; SEQ ID NO:68) and env22R (SEQ ID NO:64), env19F (nt 2020-2040; SEQ ID NO:69) and env26R (SEQ ID NO:65) for fragments 1 through 4, respectively. For the second round of amplification (nested PCR), 5 μl of the respective first-round PCR reactions was used as template along with the primer combinations env2F (nt 37-15 5' of env; SEQ ID NO:70) and env9R (nt 740-721; SEQ ID NO:71), env8F (nt 631-650; SEQ ID NO:72) and enyl-4R (nt 1437-1416; SEQ ID NO:73), env13F (nt 1333-1354; SEQ ID NO:74) and env21R (nt 2282-2265; SEQ ID NO:75), env20F (nt 2122-2141; SEQ ID NO:76) and env25R (nt 111-94 3' of env; SEQ ID NO:77) for fragments 1 through 4, respectively. Second-round amplification conditions were identical to those used for the first round. Fragments were agarose gel-purified and extracted with a Qiagen QIAEX II Gel Extraction Kit. Fragments were sequenced directly with the primers used for nested PCR along with primers env4F (SEQ ID NO:78) and env5R (SEQ ID NO:79) for fragment 1; primers env10F (SEQ ID NO:80), env11F (SEQ ID NO:81), env11R (SEQ ID NO:82), env12F (SEQ ID NO:68), and AG1 (SEQ ID NO:87)

for fragment 2; primers env15F (SEQ ID NO:83) and env19R (SEQ ID NO:84) for fragment 3; primers env22F (SEQ ID NO:85) and env24R (SEQ ID NO:86) for fragment 4. The deduced amino acid sequence of env from the HIV-1 Group O isolate HAM112 is shown in SEQ ID NO:61.

Example 3

Construction of Synthetic HIV-1 Group O env gp120/gp41 Genes

Synthetic HIV-1 Group O env gp120/gp41 gene constructs were generated. The env gp120/gp41 sequences were based on the HIV-1 Group O isolate HAM112 (SEQ ID NO:61). Determination of the env sequence of HAM112 is outlined in Example 2, hereinabove. Oligonucleotides were designed that encode the C-terminal 45 amino acids of the env gp120 and 327 amino acids of env gp41 (nucleotide #1 is the first base of the first codon of gp120 in the synthetic gene). The synthetic gene has a 26 amino acid deletion (nucleotides 643 through 720), relative to the native HAM112 gp41, that encompasses a highly hydrophobic (H) region (transmembrane region) of gp41. Thus, the full-length synthetic gp41 gene constructed is 327 amino acids.

In the synthetic oligonucleotides, the native HIV-1 codons were altered to conform to *E. coli* codon bias in an effort to increase expression levels of the recombinant protein in *E. coli*. See, for example, M. Gouy and C. Gautier, *Nucleic Acids Research* 10:7055 (1982); H. Grosjean and W. Fiers, *Gene* 18:199 (1982); J. Watson et al. (eds.), *Molecular Biology of the Gene,* 4th Ed., Benjamin Kumming Publishing Co., pp. 440 (1987). The gene construction strategy involved synthesis of a series of overlapping oligonucleotides with complementary ends (Osyn-A through Osyn-L, depicted as A through L). When annealed, the ends served as primers for the extension of the complementary strand.

The fragments then were amplified by PCR. This process ("PCR knitting" of oligonucleotides) was reiterated to progressively enlarge the gene fragment. Oligonucleotide Osyn-5' was designed for cloning into the PL vector pKRR826. The expression vector, pKRR826, is a modified form of the lambda pL promoter vector pSDKR816, described in U.S. Ser. No. 08/314,570, incorporated herein by reference. pKRR826 is a high copy number derivative of pBR322 that contains the temperature sensitive cI repressor gene (Benard et al., *Gene* 5:59 [1979]). However, pKRR826 lacks the translational terminator rrnBt1 and has the lambda pL and lambda pR promoters in the reverse orientation, relative to pSDKR816. The polylinker region of pKRR826 contains Eco RI and Bam HI restriction enzyme sites but lacks an ATG start codon. Optimal expression is obtained when the 5' end of the gene insert (including an N-terminal methionine) is cloned into the EcoRI site. Osyn-5' was designed to contain an Eco RI restriction site for cloning and an ATG codon (methionine) to provide for proper translational initiation of the recombinant proteins. The anti-sense oligonucleotides Osyn-O3' (SEQ ID NO:15), Osyn-P3' (SEQ ID NO:16), and Osyn-M (M) (SEQ ID NO:14) each contain two sequential translational termination codons (TAA,TAG) and a Bam HI restriction site. When outside primers Osyn-5' (SEQ ID NO:11) and Osyn-M (M) (SEQ ID NO:14) were used, a full-length gp41 (327 amino acids) gene was synthesized (pGO-11PL; SEQ ID NO:52). Outside oligonucleotides Osyn-5' (SEQ ID NO:11) and Osyn-O3' (SEQ ID NO:15) resulted in a truncated gp41 product of 199 amino acids (pGO-9PL; SEQ ID NO:48). Alternatively, outside oligonucleotides Osyn-5' (SEQ ID NO:11) and Osyn-P3' (SEQ ID NO:16) resulted in a truncated gp41 product 169 amino acids in length (pGO-8PL; SEQ ID NO:58).

The synthetic genes also were expressed as CMP-KDO synthetase (CKS) fusion proteins. PCR-mediated transfer of the synthetic genes from pKRR826 into pJO200 (described in U.S. Ser. No. 572,822, and incorporated herein by reference) was accomplished with an alternative outside sense oligonucleotide PCR primer (5' end), Osyn-5'CKS (SEQ ID NO:25). Osyn-5' CKS contained an Eco RI restriction site and resulted in the in-frame fusion of the synthetic gene insert to CKS in the expression vector pJO200. The 3' outside primers (antisense) Osyn-M (SEQ ID NO:14), Osyn-O3' (SEQ ID NO:15) and Osyn-P3' (SEQ ID NO:16) were used in combination with Osyn-5'CKS (SEQ ID NO:25) to generate pGO-11CKS (SEQ ID NO:54), pGO-9CKS (SEQ ID NO:50), and pGO-8 CKS (SEQ ID NO:60), respectively. These steps are detailed hereinbelow.

A. PCR Knitting of Synthetic Oligonucleotides.

Three PCR reactions (100 µl volume) were set up as follows:

(1) Reaction 1B: AmpliTaq DNA polymerase (2.5 U) and 1× buffer, along with 40 µM of each dNTP (dATP, dCTP, dGTP, and dTTP), 25 pmol each of oligonucleotides Osyn-A (SEQ ID NO:3) and Osyn-D (SEQ ID NO:5), and 0.25 pmol each of oligonucleotides Osyn-B (SEQ ID NO:17) and Osyn-C (SEQ ID NO:4);

(2) Reaction 2A: UlTma DNA Polymerase (3 U) and 1× buffer along with 1.5 mM $MgCl_2$, 40 µM of each dNTP, 25 pmol each of oligonucleotides Osyn-E (SEQ ID NO:6) and Osyn-H (SEQ ID NO:9), and 0.25 pmol each of oligonucleotides Osyn-F (SEQ ID NO:7) and Osyn-G (SEQ ID NO:8); and (3) Reaction 3A: UlTma DNA Polymerase (3 U) and 1× buffer along with 1.5 mM $MgCl_2$, 40 µM of each dNTP, 25 pmol each of oligonucleotides Osyn-I (SEQ ID NO:10) and Osyn-L (SEQ ID NO:13), and 0.25 pmol each of oligonucleotides Osyn-J (SEQ ID NO:18) and Osyn-K (SEQ ID NO:12).

Amplifications consisted of 20 cycles of 97° C. for 30 seconds, 52° C. for 30 seconds and 72° C. for 60 seconds. Reactions were then incubated at 72° C. for 7 minutes and held at 4° C. PCR-derived products 1B, 2A and 3B were gel isolated on a 1% agarose gel.

B. PCR Knitting of PCR Products From Reaction 1B and Reaction 2A.

A PCR reaction was set up with UlTma DNA Polymerase (3 U) and 1× buffer along with 1.5 mM $MgCl_2$, 40 µM of each dNTP, 24.4 pmol of oligonucleotide Osyn-5' (SEQ ID NO:11), 25 pmol of oligonucleotide Osyn-P3' (SEQ ID NO:16), and ~10 ng each of gel-isolated 1B and 2A products from Example 3, Section 1A, hereinabove. Cycling conditions were the same as in Example 3, Section 1A. A second round of amplification was used to generate more of the desired product. This was performed by making an UlTma mix as described hereinabove (100 µl reaction volume) with 49 pmol Osyn-5' (SEQ ID NO:11), 50 pmol Osyn-P3' (SEQ ID NO:16) and 5 µl of the PCR product from the first round as template. These reactions were incubated at 94° C. for 90 seconds, and then cycled as above (Section 3A). The Osyn-5'/Osyn-P3' PCR product was gel-isolated as described hereinabove.

C. Cloning of the Osyn-5'-Osyn-P3' PCR Product.

The Osyn-5'-Osyn-P3' PCR product was digested with the restriction endonucleases Eco RI+Bam HI and ligated into the vector pKRR826 (described hereinabove) that had been digested with Eco RI+Bam HI and gel-isolated. The ligation product was used to transform DH5α competent cells. The desired clone was identified by colony PCR using oligonucleotides pKRREcoRI Forward (SEQ ID NO:38) and pKRRBamHI Reverse (SEQ ID NO:39). Miniprep DNA was prepared from an overnight culture of pGO-8 candidate clone A2 and the Osyn-5'-Osyn-P3' plasmid insert was sequenced with the oligonucleotide primers pKRREcoRI Forward (SEQ ID NO:38), pKRRBamHI Reverse (SEQ ID NO:39), 41sy-1 (SEQ ID NO:44), and 41sy-2 (SEQ ID NO:41).

D. Modification of pGO-8 Candidate Clone A2.

A 100 μl volume PCR reaction was set up with UlTma DNA Polymerase (3 U) and 1× buffer, along with 1.5 mM MgCl$_2$, 40 μM of each dNTP, 50 pmol of oligonucleotides Osyn-5'-repair (SEQ ID NO:24), 50 pmol Osyn-P3' (SEQ ID NO:16), and ~1 ng of pGO-8 candidate clone A2 miniprep DNA as template (obtained from the reactions set forth hereinabove). The reaction was incubated at 94° C. for 90 seconds, and then amplified with 20 cycles of 94° C. for 30 seconds, 50° C. for 30 seconds and 72° C. for 60 seconds. The Osyn-5'-repair/Osyn-P3' PCR product then was gel isolated and digested with Eco RI+Bam HI. The digested product was ligated into Eco RI+Bam HI digested pKRR826 vector. The ligation product was used to transform DH5α competent cells. The desired clone was identified by colony PCR using oligonucleotides pKRREcoRI Forward (SEQ ID NO:38) and pKRRBamHI Reverse (SEQ ID NO:39). An overnight culture of pGO-8 candidate clone 6 was set up and a miniprep DNA was prepared. The Osyn-5'repair/Osyn-P3' plasmid insert was sequenced with the oligonucleotide primers pKRREcoRI Forward (SEQ ID NO:38), pKRRBamHI Reverse (SEQ ID NO:39), 41sy-1 (SEQ ID NO:44), and 41sy-2 (SEQ ID NO:41). Based on the sequencing results, pGO-8 candidate clone #6 was designated pGO-8PL/DHSα. SEQ ID NO:57 presents the nucleotide sequence of the coding region. SEQ ID NO:58 presents the amino acid sequence of the pGO-8PL recombinant protein. The pGO-8PL recombinant protein consists of a N-terminal methionine, 45 amino acids region of env gp120 (HIV-1 Group O, HAM112 isolate), and 169 amino acids of env gp41 (HIV-1 Group 0, HAM112 isolate).

E. Construction of pGO-8CKS/XL1.

pGO-8CKS/XL1(SEQ ID NO:59) presents the nucleotide sequence of the coding region) encodes the recombinant protein pGO-8CKS. SEQ ID NO:60 is the amino acid sequence of pGO-8CKS. This protein consists of 246 amino acids of CKS/polylinker, 45 amino acids of env gp120 (HIV-1 Group O, HAM112 isolate), and 169 amino acids of env gp41 (HIV-1 Group O, HAM112 isolate). The construction of pGO-8CKS/XL1 was accomplished as follows.

A PCR reaction (100 μl volume) was set up with UlTma DNA Polymerase (3 U) and 1× buffer along with 1.5 mM $MgCl_2$, 40 μM of each dNTP, 50 pmol of Osyn-5'CKS (SEQ ID NO:25), 50 pmol Osyn-P3' (SEQ ID NO:16), and 1 ng pGO-8PL clone #6 miniprep DNA. The reaction was incubated at 94° C. for 90 seconds then amplified with 25 cycles of 94° C. for 30 seconds; 55° C. for 30 seconds; 72° C. for 90 seconds. Then, the Osyn-5'CKS/Osyn-P3' PCR product was gel isolated. EcoR I+Bam HI digested the Osyn-5'CKS/Osyn-P3' PCR product and the vector pJO200. The digested pJO200 vector was gel isolated and ligated to digested Osyn-5'CKS/Osyn-P3' PCR product. XL1-Blue supercompetent cells were transformed with the ligation and plated on LB+ampicillin plates supplemented with 20 mM glucose. Colonies were restreaked for isolation on the same type of plates. An overnight culture of clone pGO-8CKS/XL1 was grown in LB broth+100 μg/ml carbenicillin (Sigma Chemical Co.)+20 mM glucose (Sigma Chemical Co.). Frozen stocks (0.5 ml overnight culture+0.5 ml glycerol) were made and DNA was prepared for sequence analysis. The following oligonucleotides were used as sequencing primers: CKS-1 (SEQ ID NO:30), CKS-2 (SEQ ID NO:31), CKS-3 (SEQ ID NO:32), CKS-4 (SEQ ID NO:33), 43461 (SEQ ID NO:2), 43285 (SEQ ID NO:1), 41sy-1B (SEQ ID NO:29), 41sy-2B (SEQ ID NO:34), CKS176.1 (SEQ ID NO:19), and CKS3583 (SEQ ID NO:20).

F. Construction of pGO-9PL/DH5α.

The construct pGO-9PL/DH5α encodes the recombinant protein pGO-9PL. SEQ ID NO:47 is the nucleotide sequence of the coding region of pGO-9PL/DH5α and SEQ ID NO: 48 is the amino acid sequence of the pGO-9PL recombinant protein. This protein consists of an N-terminal methionine, 45 amino acids of env gp120 (HIV-1 Group O, HAM112 isolate), and 199 amino acids of env gp41 (HIV-1 Group O, HAM112 isolate). Construction of pGO-9PL/DH5α was accomplished as follows.

Step 1: A 100 μl PCR reaction was set up with UlTma DNA Polymerase (3 U) and 1× buffer, along with 1.5 mM $MgCl_2$, 40 μM of each dNTP, 50 pmol of Osyn-5' (SEQ ID NO:11), 50 pmol of Osyn-H (SEQ ID NO:9), and ~2 ng of pGO-8 candidate clone 6 miniprep DNA (obtained from Example 3, Section D hereinabove) as template. The reaction was incubated at 94° C. for 120 seconds, and then amplified with 8 cycles of 94° C. for 30 seconds, 55° C. for 30 seconds and 72° C. for 60 seconds.

Step 2: A 100 μl PCR reaction was set up with UlTma DNA Polymerase (3 U) and 1× buffer along with 1.5 mM $MgCl_2$, 40 μM of each dNTP, 50 pmol of Osyn-5' (SEQ ID NO:11), 50 pmol Osyn-O3' (SEQ ID NO:15), and 10 μl of the PCR reaction from step 1 as template. The reaction was incubated at 94° C. for 120 seconds then amplified with 18 cycles of 94° C. for 30 seconds, 55° C. for 30 seconds, 72° C. for 60 seconds, followed by incubation at 72° C. for 5 minutes.

The Osyn-5'/Osyn-O3' PCR product (2A/2B) then was gel-isolated and digested with Eco RI+Bam HI. The digested product was ligated into Eco RI+Bam HI digested pKRR826 vector. The ligation product next was used to transform DH5α competent cells. An overnight culture of pGO-9PL candidate clone 3 was set up and a miniprep DNA was prepared. The Osyn-5'/Osyn-O3' plasmid insert was sequenced with the following oligonucleotides as primers: pKRREcoR1 Forward (SEQ ID NO:38), pKRRBamHI Reverse (SEQ ID NO:39), 41sy-1C (SEQ ID NO:40), 41sy-2 (SEQ ID NO:41), 41sy-3 (SEQ ID NO:42) and 41sy-4 (SEQ ID NO:23). pGO-9PL clone #3 then was restreaked for isolation. An isolated colony was picked, an overnight culture of it was grown, and a frozen stock (0.5 ml glycerol+0.5 ml overnight culture) was made. The stock was stored at −80° C. The sequence was confirmed using the primers indicated hereinabove, and this clone was designated as pGO-9PL/DH5α (SEQ ID NO:47 presents the nucleotide sequence of the coding region, and SEQ ID NO:48 presents the amino acid sequence of coding region). pGO-9PL/DH5α was restreaked, an overnight culture was grown, and a miniprep DNA was prepared (this prep was designated as H5).

G. Construction of pGO-9CKS/XL1

The construct pGO-9CKS/XL1 encodes the recombinant protein pGO-9CKS. SEQ ID NO:50 is the amino sequence of the pGO-9CKS recombinant protein. This protein consists of 246 amino acids of CKS and polylinker followed by 45 amino acids of env gp120 (HIV-1 Group O, HAM112 isolate), and 199 amino acids of env gp41 (HIV-1 Group O, HAM112 isolate). The construction of pGO-9CKS/XL1 was accomplished as follows.

Two PCR reactions (100 μl volume) were set up with UlTma DNA Polymerase (3 U) and 1× buffer, along with 1.5 mM MgCl$_2$, 40 μM of each dNTP, 50 pmol of Osyn-5'CKS (SEQ ID NO:25), 50 pmol Osyn-O3' (SEQ ID NO:15) and 1 ng pGO-9PL candidate clone 3 miniprep DNA (obtained from Example 3, Section F, hereinabove). Each reaction was incubated at 94° C. for 120 seconds, then amplified with 24 cycles of 94° C. for 30 seconds, 55° C. for 30 seconds, 72° C. for 120 seconds, followed by incubation at 72° C. for 5 minutes. The Osyn-5'CKS/Osyn-O3' PCR product then was gel isolated. The Osyn-5'CKS/Osyn-O3' PCR product and the vector pJO200 was digested with EcoR I+Bam HI. The digested pJO200 vector was gel isolated and ligated to the digested Osyn-5'CKS/Osyn-O3' PCR product. XL1-Blue supercompetent cells were transformed with the ligation and plated on LB+ampicillin plates supplemented with 20 mM glucose. Colonies were restreaked for isolation on the same type of plates. An overnight culture of clone pGO-9CKS candidate clone 4 was grown in LB broth+100 mg/ml carbenicillin (Sigma Chemical Co.)+20 mM glucose (Sigma Chemical Co.). Made frozen stocks (0.5 ml overnight culture+0.5 ml glycerol) and prepared DNA for sequence analysis. The following oligonucleotides were used as sequencing primers: CKS-1 (SEQ ID NO:30), CKS-2 (SEQ ID NO:31), CKS-3 (SEQ ID NO:32), CKS-4 (SEQ ID NO:33), 43461 (SEQ ID NO:2), 43285 (SEQ ID NO:1), 41sy-1B (SEQ ID NO:29), 41sy-2B (SEQ ID NO:34), 41sy-3B (SEQ ID NO:35), CKS176.1 (SEQ ID NO:19), CKS3583 (SEQ ID NO:20), and pTB-S8 (SEQ ID NO:28). Clone pGO-9CKS candidate clone 4 was designated as pGO-9CKS/XL1(SEQ ID NO:49 presents the nucleotide sequence of coding region, and SEQ ID NO:50 presents the amino acid sequence of coding region).

H. Construction of Osyn I-M Fragment.

The Osyn-O-M fragment was constructed as follows. A 100 μl PCR reaction was set up using AmpliTaq DNA Polymerase (2.5 U), 1× buffer, 50 μM of each dNTP, 50 pmol I-PCR (SEQ ID NO:26), 50 pmol Osyn-M (SEQ ID NO:14) and 10 ng of gel-isolated PCR fragment 3A (Example 3, section A, hereinabove). The reaction was incubated at 95° C. for 105 seconds, and then it was amplified with 15 cycles of 95° C. for 30 seconds, 55° C. for 30 seconds, 72° C. for 60 seconds, and then it was held at 72° C. for 7 minutes. The product, designated as Osyn I-M, was gel-isolated and cloned into the PCR II vector (TA Cloning Kit; Invitrogen, San Diego, Calif.) following the manufacturer's recommended procedure. The resulting ligation product was used to transform DH5α competent cells. Plasmid miniprep DNA was generated from an overnight culture of clone IM-6, and the gene insert was sequenced with oligonucleotides 56759 (SEQUENCE ID NO: 45) and 55848 (SEQ ID NO:46).

I. Synthesis and Knitting of PCR Fragments I/6R and IM-6F.

These procedures were performed as follows.

Step 1: The following PCR reactions (100 μl volume) were set up: (a) I/6R with AmpliTaq DNA Polymerase (2.5 U), 1× buffer, 50 μM of each dNTP, 50 pmol I-PCR (SEQ ID NO:26), 50 pmol IM-6R (SEQ ID NO:22) and 281 ng of clone IM-6 (obtained from Example 3, Section H) as template; (b) 6F/M with AmpliTaq DNA Polymerase (2.5 U), 1× buffer, 50 μM of each dNTP, 50 pmol IM-6F (SEQ ID NO:21), 50 pmol M-PCR (SEQ ID NO:27) and 281 ng of clone IM-6 (obtained from Example 3, Section H) as template.

The reactions were incubated at 95° C. for 105 seconds, and then amplified with 20 cycles of 94° C. for 15 seconds, 60° C. for 30 seconds, 72° C. for 60 seconds, then incubated at 72° C. for 7 minutes. The PCR products I/6R and 6F/M next were gel isolated following the procedures as described hereinabove.

Step 2: A PCR reaction (100 μl volume) was set up with UlTma DNA Polymerase (3 U) and 1× buffer along with 1.5 mM MgCl$_2$, 40 μM of each dNTP, 50 pmol of I-PCR (SEQ ID NO:26), 50 pmol M-PCR (SEQ ID NO:27), ~50 ng I/6R, and ~20 ng 6F/M. The reaction was incubated at 95° C. for 105 seconds, and then it was amplified with 20 cycles of 94° C. for 15 seconds, 55° C. for 30 seconds, 72° C. for 60 seconds, followed by incubation at 72° C. for 7 minutes. The PCR product was processed on a Centri-sep column (Princeton Separations) following the manufacturer's instructions.

J. Construction of pGO-11PL/DH5α.

The construct pGO-11PL/DH5α encodes the recombinant protein pGO-11PL. SEQ ID NO:52 is the amino acid sequence of the pGO-11PL recombinant protein. This protein consists of an N-terminal methionine, 45 amino acids of env gp120 (HIV-1 Group O, HAM112 isolate), and 327 amino acids of env gp41 (HIV-1 Group O, HAM112 isolate). pGO-11PL/DH5α was constructed as follows.

The final PCR product from Example 3, Section I and pGO-9PL vector (miniprep H5 from Example 3, section F) were digested sequentially with Age I and Bam HI. The digested pGO-9PL was then treated with calf intestinal alkaline phosphatase (BRL Life Technologies) for 15 minutes at 37° C., phenol/chloroform extracted, and precipitated with NaOAc and EtOH. The vector (pGO-9PL) was subsequently gel-isolated. The digested pGO-9PL and the digested PCR product were ligated, and the ligation product was used to transform DH5α competent cells. Colonies were restreaked for isolation. Clone pGO11-4 then was identified and restreaked for isolation. An overnight culture of pGO11-4 was prepared in order to generate frozen stocks and perform miniprep DNA for sequencing. Clone pGO11-4 was sequenced with the following oligonucleotide primers: pKRREcoR1 Forward (SEQ ID NO:38), pKRRBamHI Reverse (SEQ ID NO:39), 41sy-1C (SEQ ID NO:40), 41sy-2 (SEQ ID NO:41), 41sy-3 (SEQUENCE ID NO: 42), 41sy-4 (SEQ ID NO:23), 41sy-5B (SEQ ID NO:43), 41sy-5C (SEQ ID NO:36) and 41sy-6B (SEQ ID NO:37). Based on the sequencing results, this clone was designated as pGO-11PL/DH5α (SEQ ID NO:51 presents the nucleotide sequence of the coding region, and SEQ ID NO:52 presents the amino acid sequence of coding region).

K. Construction of pGO-11CKS/XL1.

The construct pGO-11CKS/XL1 encodes the recombinant protein pGO-11CKS. SEQ ID NO:54 is the amino sequence of the pGO-11CKS recombinant protein. This protein consists of 246 amino acids of CKS and polylinker followed by 45 amino acids of env gp120 (HIV-1 Group O, HAM112 isolate), and 327 amino acids of env gp41 (HIV-1 Group O, HAM112 isolate). pGO-11CKS/XL1 was constructed as follows.

A PCR reaction (100 μl volume) was set up with UITma DNA Polymerase (3 U) and 1× buffer along with 1.5 mM $MgCl_2$, 40 μM of each dNTP, 50 pmol of Osyn-5'CKS (SEQ ID NO:25), 50 pmol Osyn-M (SEQ ID NO:14), and 1 ng pG011-4 (obtained from Example 3, Section J) as template. The reaction was incubated at 94° C. for 105 seconds, and then amplified with 20 cycles of 94° C. for 30 seconds, 55° C. for 30 seconds, 72° C. for 120 seconds, followed by incubation at 72° C. for 7 minutes. The Osyn-5'CKS/Osyn-M PCR product was gel isolated. Next, the Osyn-5'CKS/Osyn-M PCR product and the vector pJO200 were EcoR I+Bam HI digested. The digested pJO200 vector was gel isolated. Overnight (16° C.) ligations were set up with the digested PCR product. XL1-Blue supercompetent cells were transformed with the ligation and plated on LB+ampicillin plates supplemented with 20 mM glucose. Colonies were restreaked for isolation on the same plates. An overnight culture (LB medium+100 µg/ml carbenicillin+20 mM glucose) of clone pGO-11CKS clone candidate 2 then was set up. Frozen stocks (0.5 ml 80% glycerol+0.5 ml overnight culture) were made as well as miniprep DNA for sequencing. The following oligonucleotides were used as primers for sequence analysis: CKS-1 (SEQ ID NO:30), CKS-2 (SEQ ID NO:31), CKS-3 (SEQ ID NO:32), CKS-4 (SEQ ID NO:33), 43461 (SEQ ID NO:2), 43285 (SEQ ID NO:1), 41sy-1B (SEQ ID NO:29), 41sy-2B (SEQ ID NO:34), 41sy-3B (SEQ ID NO:35), 41sy-4 (SEQ ID NO:23), 41sy-5C (SEQ ID NO:36), 41sy-6B (SEQ ID NO:37), CKS176.1 (SEQ ID NO:19), CKS3583 (SEQ ID NO:20), and pTB-S8 (SEQ ID NO:28). pGO-11 CKS clone #2 was designated as pGO-11CKS/XL1. SEQ ID NO:53 presents the nucleotide sequence of the coding region of pGO-11CKS/XL1, and SEQ ID NO:54 presents the amino acid sequence of the coding region of pGO-11CKS/XL1.

Example 4

Construction of pHIV210/XL1-Blue

SEQ ID NO:55 is the amino acid sequence of the pHIV-210 recombinant protein. This protein consists of 247 amino acids of CKS/linker sequences, 60 amino acids from env gp120 (#432-491; HIV-2 isolate D194.10), and 159 amino acids of env gp36 (#492-650; HIV-2 isolate D194.10). The construction of pHIV210/XL1-Blue was accomplished as follows.

The genomic DNA of HIV-2 isolate D194.10 [H. Kuhnel et al., *Nucleic Acids Research* 18: 6142 (1990)] was cloned into the EMBL3 lambda cloning vector. See H. Kuhnel et al., *Proc. Nat'l. Acad. Sci. USA* 86: 2383-2387 (1989), and H. Kuhnel et al., *Nucleic Acids Research* 18: 6142 (1990), incorporated herein by reference. The lambda clone containing D194.10 (lambda A10) was obtained from Diagen Corporation (Düsseldorf, Germany). A PCR reaction (100 µl volume) was set up using AmpliTaq DNA polymerase (3.75 units), 200 µM each dATP, dCTP, dGTP, and dTTP, 0.5 µg primer 3634 (SEQ ID NO:88; annealing to positions 7437-7455 on the HIV-2 isolate D194.10 (EMBL accession #X52223), 0.5 µg primer 3636 (SEQ ID NO:89, annealing to positions 8095-8077), 1×PCR buffer, and 5 µl of the lambda A10 DNA diluted 1:50. The reaction was incubated 5 minutes at 94° C. then amplified with 35 cycles of 94° C. for 1 minute, 45° C. for 1 minute, 72° C. for 2 minutes; followed by an incubation at 72° C. for 5 minutes. The PCR reaction was extracted with phenol/chloroform (Boehringer Mannheim Corporation, Indianapolis, Ind.) and the DNA was ethanol (AAPER Alcohol & Chemical Company, Shelbyville, Ky.) precipitated. The DNA was digested with EcoRI+Bam HI and gel purified on an 1.5% agarose gel (SeaKem GTG agarose, FMC Corporation, Rockland, Me.). The purified product was ligated into EcoRI+Bam HI digested pJO200 vector using 800 units of T4 DNA ligase (New England BioLabs). XL1-Blue supercompetent cells (Stratagene) were transformed with 2 µl of the ligation as outlined by the manufacturer and plated on LB plates supplemented with ampicillin (Sigma Chemical Company). Overnight cultures were established by inoculating single colonies into Superbroth II media (GIBCO BRL, Grand Island, N.Y.) supplemented with 50 µg/ml ampicillin (Sigma) and 20 mM glucose (Sigma). Frozen stocks were established by adding 0.3 ml of 80% glycerol to 0.7 ml of overnight. After mixing stocks were stored at −70° C. Miniprep DNA was prepared from the overnight cultures using the alkaline lysis method followed by PEG precipitation. Sequence reactions were performed with a 7-deaza-dGTP Reagent Kit with Sequenase Version 2.0 (United States Biochemical Corporation, Cleveland, Ohio) as outlined by the manufacturer. Reactions were run on 6% acrylamide gels (GIBCO BRL Gel-Mix 6) using the IBI gel apparatus as recommended by the manufacturer. Based on sequencing results, pHIV-210 clone #7 was designated as pHIV-210. The amino acid sequence of the pHIV-210 coding region is presented as SEQ ID NO:55.

Example 5

Growth and Induction of *E. coli* Strains with HIV-1 Group O Recombinant gp41 Antigen Construct Overnight seed cultures of pGO-9CKS/XL1 and pGO-11CKS/XL1 were prepared in 500 ml sterile Excell Terrific Broth (available from Sigma Chemical Corp., St. Louis Mo.) supplemented with 100 µg/ml sodium ampicillin, and placed in a shaking orbital incubator at 32° C. or 37° C. One hundred milliliter (100 µl) inocula from seed cultures were transferred to flasks containing 1 liter sterile Excell Terrific Broth supplemented with 100 µg/ml sodium ampicillin. Cultures were incubated at 37° C. until the culture(s) reached mid-logarithmic growth and then induced with 1 mM ITPG (isopropylthiogalactoside) for 3 hours at 37° C. (In the case of PL vector constructs, cultures were incubated at 32° C. until the culture (s) reached mid-logarithmic growth and then induced for 3 hours by shifting the temperature of the culture(s) to 42° C.) After the induction period, cells were pelleted by centrifugation and harvested following standard procedures. Pelleted cells were stored at −70° C. until further processed.

Example 6

Isolation and Solubilization of HIV-1 Group O Recombinant gp41 Antigen Produced as Insoluble Inclusion Bodies in *E. coli*

Frozen cells obtained from Example 5 were resuspended by homogenization in cold lysis buffer comprising 50 mM Tris pH 8, 10 mM Na EDTA, 150 mM NaCl, 8% (w/v) sucrose, 5% Triton X-100® (v/v), 1 mM PMSF and 1 mM pepstatin A. Lysozyme was added to the homogenates at a concentration of 1.3 mg per gram of cells processed, and the resultant mixture was incubated for 30 minutes on ice to lyse the cells. Inclusion bodies were separated from soluble proteins by centrifugation. These pelleted inclusion bodies were washed and pelleted sequentially in (1) Lysis Buffer; (2) 10 mM Na EDTA pH 8, 30% (w/v) sucrose; and (3) water. The washed inclusion bodies were resuspended in 50 mM Tris pH 8, 10 mM Na EDTA, 150 mM NaCl and 3 M urea, and incubated on ice for 1 hour. The inclusion bodies then were separated from the solubilized proteins by centrifugation. The pelleted inclusion bodies were fully solubilized in 7 M guanidine-HCl, 50 mM Tris pH 8, 0.1% (v/v) beta-mercaptoethanol (BME) overnight at 4° C. The solubilized recombinant antigens were clarified by centrifugation, passed through a 0.2 μm filter and stored at ≦−20° C. until purified by chromatography.

Example 7

Purification of Recombinant HIV-1 Group O gp41 Antigen by Chromatography

Solubilized HIV-1 Group O recombinant gp41 antigens obtained from Example 6 were purified by a two-step method, as follows. Guanidine-HCl extracts of insoluble antigens were purified by size exclusion chromatography on a Sephacryl S-300 column equilibrated with 50 mM Tris pH 8, 8 M Urea and 0.1% BME (v/v). SDS-polyacrylamide electrophoresis was used to analyze fractions. Fractions containing the recombinant gp41 antigen were pooled and then concentrated by ultrafiltration. The recombinant antigen concentrate was treated with 4% SDS (w/v) and 5% BME (w/v) at room temperature for 3 hours. SDS treated antigen was further purified by size exclusion chromatography on a Sephacryl S-300 column equilibrated with 25 mM Tris pH 8, 0.15 M NaCl, 0.1% v/v BME, 0.1% SDS (w/v). SDS-polyacrylamide electrophoresis was used to analyze the fractions. Fractions containing purified recombinant antigen were pooled, passed through a 0.2 μm filter and stored at −70° C.

Example 8

Preparation of HIV-1 Group M Antigen

Cells containing the plasmid pTB319 were grown and induced as described in Example 5. Cells were lysed and inclusion bodies were processed essentially as described in Example 5 of U.S. Pat. No. 5,124,255, incorporated herein by reference. The pellet material was subsequently solubilized in SDS, Phosphate, pH 6.8 and then subjected to chromatography on an S-300 column.

Example 9

Preparation of HIV-2 Antigen pHIV-210/XL1-Blue cells (Example 4, hereinabove) were grown and induced as described in Example 5. Cells were lysed with a buffer containing phosphate, $MgCl_2$, Na EDTA, Triton X-100® pH 7.4 supplemented with Benzonase, Lysozyme, and PMSF. Inclusion bodies were separated from soluble proteins by centrifugation. The pellet was washed sequentially with: distilled $H_2O$; Triton X-100®, deoxycholate, NaCl, Phosphate pH 7.0; 50 mM Phosphate, pH 7.0; urea, SDS in phosphate, pH 7.0+BME. Proteins were solubilized in SDS, phosphate, pH 7.0 and BME then subjected to chromatography on an S300 column.

Example 10

One-Step Immunochromatographic Assay for Simultaneous Detection and Differentiation of HIV-1 Group M, HIV-1 Group O and HIV-2

A. Reagent Preparation

1. A selenium (Se) colloid suspension was prepared substantially as follows: $SeO_2$ was dissolved in water to a concentration of 0.0625 gm/ml. Ascorbate then was dissolved in water to a concentration of 0.32 gm/ml and heated in a 70° C. water bath for 24 hours. The ascorbate solution then was diluted to 0.0065 gm/ml in water. The $SeO_2$ solution was quickly added to the diluted ascorbate solution and incubated at 42° C. Incubation was ended after a minimum of 42 hours when the absorbance maximum exceeded 30 at a wavelength between 542 nm and 588 nm. The colloid suspension was cooled to 2-8° C., then stored. Selenium colloid suspension is available from Abbott Laboratories, Abbott Park, Ill. (Code 25001).

2. Selenium colloid/antibody conjugates were prepared as follows. The selenium colloid suspension was concentrated to an absorbance of 25 (OD 500-570) in distilled water. Then, 1M MOPS was added to a final concentration of 10 mM pH 7.2. Goat antibodies specific for human IgG Fc region (or other species of antibody specific for human IgG Fc region) were diluted to a concentration of 0.75 mg/ml with 50 mM Phosphate buffer, and the resultant antibody preparation then was added with mixing to the selenium colloid suspension prepared as described hereinabove, to a final antibody concentration of 75 μg/ml. Stirring was continued for 40 minutes. Then, 1% (by weight) bovine serum albumin (BSA) was added to the solution, and the selenium colloid/antibody conjugate solution was stirred for an additional 15 minutes and centrifuged at 5000×g for 90 minutes. Following this, 90% of the supernatant was removed, and the pellet was resuspended with the remaining supernatant. Immediately prior to coating this selenium-IgG conjugate to a glass fiber pad, it was diluted 1:10 with conjugate diluent (1% [by weight] casein, 0.1% [weight] Triton X-405®, and 50 mM Tris, pH 8.2).

3. Procedural control reagent was prepared as a mixture of HIV-1 (group M), HIV-1 (group O), and HIV-2 positive sera, and is utilized on a separate strip device as a positive control of the assay.

4. Negative control reagent used was normal human utilized on a separate test device as a negative control of the assay.

B. Application Pad Preparation.

The application pad material comprises resin bonded glass fiber paper (Lydall). Approximately 0.1 ml of the prepared conjugate (described in preceding paragraph 2) is applied to the application pad.

C. Chromatographic Material Preparation.

All reagents are applied to a nitrocellulose membrane by charge and deflect reagent jetting. The nitrocellulose is supported by a MYLAR® membrane that is coated with a pressure sensitive adhesive.

The test sample capture reagents were prepared by (a) diluting the specific antigen prepared as described hereinabove to a concentration of 0.5 mg/ml in jetting diluent (100 mM Tris, pH 7.6 with 1% sucrose (by weight), 0.9% NaCl and 5 μg/ml fluorescein) for HIV-1 group O capture reagent (pGO-9/CKS, SEQ ID NO:50), (b) for HIV-1 group M, subgroup B capture reagent (pTB319, SEQ ID NO:56), and (c) for HIV-2 capture reagent (pHIV-210, SEQ ID NO:55). 0.098 μl of a first capture reagent (reagent HIV-1 group M subgroup B; SEQ ID NO:56) was applied to the strip at the designated capture location and constituted one patient capture site. Likewise, 0.098 μl of a second capture reagent (reagent HIV-1 group O; SEQ ID NO:50) was applied to the strip at the designated capture location and constituted one patient capture site, and 0.098 μl of a third capture reagent (reagent HIV-2; SEQ ID NO:55) was applied to the strip at the designated capture location and constituted one patient capture site.

D. Rapid Assay for the Presence of Antibodies to HIV.

A rapid assay for the presence of antibodies to HIV in test samples serum, whole blood, saliva, and urine samples was performed as follows. In a 1.5 ml Eppendorf tube, 5 μl of serum and 600 μl of sample elution buffer (SEB) (containing 50 mM Tris, 1% BSA (w/v), 0.4% Triton X-405® (v/v), 1.5% Casein (w/v), 3% Bovine IgG (w/v), 4% *E. coli* lysate (v/v), [pH 8.2]) was mixed. Four drops of this mixture was applied to the sample well of the STAR housing. Next, 1 μl of serum or whole blood was added to 100 μl of SEB in a well of a microtiter plate, and the nitrocellulose strip was added in the well. Following this, 1 μl of serum or whole blood was spotted in the test device of the invention's sample well directly and 4 drops of SEB was added. When testing saliva, 50 or 75 μl of saliva was added to 50 μl or 25 μl of SEB, respectively, in a well of a microtiter plate, and the nitrocellulose test strip then was added to the well. When testing urine, 50 μl of urine was added to 50 μl of SEB in a well of a microtiter plate, and the nitrocellulose test strip was added in the well. Alternatively, 100 μl of urine was used in the well of a microtiter plate, and the nitrocellulose test strip was added, without using SEB.

The IgG in the sample was bound by the selenium-goat anti-human IgG colloid in the conjugate pad, and the complexes were chromatographed along the length of the nitrocellulose membrane test strips on which the three recombinant antigens pGO-9 CKS SEQ ID NO:50), pTB319 (HIV-1 group M (subgroup B), SEQ ID NO:56) and pHIV210 (HIV-2, SEQ ID NO:55) previously were applied at a concentration of 1 mg/ml using a biodot machine, which provided positive displacement dispensing using precise drop sizes. The test device then was incubated at room temperature for two minutes, and the results were read visually.

E. Spiked Whole Blood Assay.

In a 1.5 ml Eppendorf tube, the equivalent of 1 μl blood from either confirmed positive HIV-1 group O, HIV-1 group M or HIV-2, or confirmed negative for HIV-1 group O, HIV-1 group M or HIV-2 whole blood test sample was added to 5 μl of a confirmed negative HIV-1 group O, HIV-1 group M or HIV-2 serum along with 100 μl of SEB, and mixed. This mixture was applied to the sample well of the test device of the invention.

The IgG in the sample was bound by the selenium-goat anti-human IgG colloid in the conjugate pad, and the complexes were chromatographed along the length of the nitrocellulose membrane test strips on which the three recombinant antigens pGO-9 CKS SEQ ID NO:50), pTB319 (HIV-1 group M (subgroup B), SEQ ID NO:56) and pHIV210 (HIV-2, SEQ ID NO:55) previously were applied at a concentration of 1 mg/ml using a biodot machine, which provided positive displacement dispensing using precise drop sizes. The test device then was incubated at room temperature for two minutes, and the results were read visually.

F. Results.

If antibody to antigen 1 was present in the test sample, a visible reaction was indicated in the capture zone area of antigen 1 and in the assay completion zone, and not in the zones of antigen 2 or antigen 3. If antibody to antigen 2 was present in the test sample, a visible reaction was indicated in the capture zone area of antigen 2 and in the assay completion zone, and not in the zones of antigen 1 or antigen 3. If antibody to antigen 3 was present in the test sample, a visible reaction was indicated in the capture zone area of antigen 3 and in the assay completion zone, and not in the zones of antigen 1 or antigen 2. Also, a negative control should be non-reactive (show no visible reaction) in the zones of antigen 1, antigen 2 and antigen 3, but should be reactive in the assay completion zone. A positive control (known reactive antibody to antigen 1, 2 and/or 3) should be reactive in the zone of the appropriate antigen to which it specifically binds in an antigen/antibody reaction. A result was considered invalid when a positive reaction occurred in one of the antigen capture zones but not in the assay completion zone, and the test was repeated.

(i) Assaying for Antibodies in Blood, Urine and Saliva. The blood, urine, and saliva of three patients (identified by patient numbers 0109, 4068, and 4475) were tested on nitrocellulose solid phase devices of the invention as described herein and following the assay protocol as set forth hereinabove. Each blood and urine test sample of each patient 0109, 4068 and 4475 was reactive with antigen 1 (pTB319; SEQ ID NO:56). The saliva test sample of patients 4068 and 4475 also were reactive with antigen 1, while patient 0109's saliva test sample was non-reactive in the test device of the invention. The saliva test sample of patient 0109 was later retested by a standard EIA and confirmed non-reactive for antibodies to HIV-1 gp41, indicating that the results obtained for the saliva test sample of patient 0109 were valid.

(ii) Assaying Negative Samples for HIV Antibodies. Two negative sera and two negative whole blood test samples, each spiked with the same two negative sera, were tested. Samples contained no antibodies specific for the relevant antigens and the test samples were negative after assay on the test (i.e. no reactivity, as indicated by no visible bar signifying a reaction in either position O, M or 2). Test sample was present in each test device, as indicated by a positive reaction bar in the test sample reactivity zone.

(iii) Assaying for HIV-1 Group M Antibody. Five HIV-1 Group M sera and five whole blood samples spiked with the HIV-1 Group M positive sera were tested using ten devices. HIV-1 Group M samples were seen to contain antibodies specific for HIV-1 Group M antigen (pTB319) as shown by development of a reaction line at the HIV-1 Group M antigen zone, and visible reaction lines could be seen in the assay completion zone of nine out of 10 test devices. Although a band was present in one particular test device in the capture zone for HIV-1 group M antibody, test sample did not reach the assay completion zone and, thus, the assay needed to be repeated for this particular sample. No cross-reactivity was observed with the capture reagents for HIV group O and HIV-2.

(iv) Assaying for HIV-1 Group O Antibodies. Two confirmed positive HIV-1 Group O sera and two whole blood test samples spiked with HIV-1 Group O sera were tested using an additional four devices. The HIV-1 Group O samples were found to contain antibodies specific for HIV-1 Group O antigen as indicated by a positive bar result in the HIV-1 Group antigen capture zone area, with reaction lines visible in the assay completion zone of each device. No cross-reaction with HIV-1 group M or HIV-2 capture antigens (no visible bar) was observed.

(v) Assaying for HIV-2 Antibodies. Ten further test devices were used to test five HIV-2 confirmed positive sera and whole blood spiked with the 5 HIV-2 sera. The HIV-2 samples were found to contain antibodies specific for HIV-2 antigen (pHIV210) as shown by reaction bars at the HIV-2 antigen zone. No reaction was observed between these test samples and the HIV-1 Group O or HIV-1 Group M antigens; visible reaction lines were seen in the assay completion zone of each device.

(vi) Assaying HIV-1 Group M, HIV-1 Group O, HIV-2 and Negative Samples. Four final devices were used to test an HIV-1 Group M-positive test sample, an HIV-1 Group O-positive test sample, an HIV-2-positive test sample and a negative control sample. The negative test serum did not react with any antigen in the antigen capture zone; the HIV-1 Group M-positive test sample was reactive only with the HIV-1 Group M antigen; the HIV-1 Group O-positive test sample was reactive only with the HIV-1 Group O antigen; and the HIV-2-positive test sample was reactive only with the HIV-2 antigen. Visible reaction lines were seen in the assay completion zone of each device.

The five HIV-1 group M and the two HIV-1 group O test samples used were confirmed seropositive samples which had been previously tested using a commercially-available enzyme immunoassay (Abbott #3A77) and had been PCR amplified, sequenced and subtyped based on phylogenetic analysis. The five HIV-2 samples used were seropositive using the same EIA and were confirmed as HIV-2-positive samples using an HIV-2 Western blot test (Sanofi).

Example 11

Construction of Synthetic HIV-1 Group M and HIV-1 Group O Hybrid Genes

A. Modification of pTB319

The plasmid pTB319 (U.S. Pat. No. 5,124,255, incorporated herein by reference) encodes a truncated gp41 recombinant protein due to a one base deletion within the synthetic HIV-1 Group M gp41 gene resulting in a frame-shift. In order to facilitate the generation of HIV-1 Group M and Group O hybrid gene constructs, site-specific mutagenesis was used to eliminate the frame-shift within the gp41 coding region in pTB319. This was accomplished by sequentially digesting the plasmid pTB319 with the restriction endonucleases Rsr II and Bst XI. The synthetic oligonucleotides pTB319+A (SEQ ID NO:98) and pTB319+T (SEQ ID NO:99) were annealed and ligated into the Rsr II and Bst XI digested pTB319. The ligation product was used to transform supercompetent XL1-Blue cells and the cells were plated on LB agar plates supplemented with 150 µg/ml ampicillin. Colony PCR was used to identify correctly modified clones using the primer combinations pTB-S4 (SEQ ID NO:100)/pTB-S7 (SEQ ID NO:101) and pTB-S4 (SEQUENCE ID NO:100)/63168 (SEQ ID NO:121). Overnight cultures were established for candidate clones in LB broth supplemented with 3 mM glucose and 200 µg/ml ampicillin for preparation of miniprep DNA. The entire coding region was sequenced using the oligonucleotide primers: 43461 (SEQ ID NO:2), 43285 (SEQ ID NO:1), CKS-1 (SEQ ID NO:30), CKS-3 (SEQ ID NO:32), pTB-S1 (SEQ ID NO:102), pTB-S2 (SEQ ID NO:103), pTB-S3 (SEQ ID NO:104), pTB-S4 (SEQ ID NO:100), pTB-S5 (SEQ ID NO:105), pTB-S6 (SEQ ID NO:106), pTB-S7 (SEQ ID NO:101), and pTB-S8 (SEQ ID NO:28). Based on sequencing results, clone pTB319+A-#31 (pGMcks-1) has the desired coding region sequence. This clone was subsequently designated as pGM-1CKS/XL1 (SEQ ID NO:107 presents the nucleotide sequence of the coding region). SEQ ID NO:108 is the amino acid sequence of the pGM-1CKS recombinant protein.

B. Construction of pGO-12CKS/XL1

The construct pGO-12CKS/XL1 encodes the recombinant protein pGO-12CKS, the amino acid sequence of which is shown in SEQ ID NO:91. This protein consists of 250 amino acids of CKS/polylinker fused to 42 amino acids of env gp120 (HIV-1 Group M, HXB2R isolate), 200 amino acids of env gp41 (HIV-1 Group M, HXB2R isolate), 45 amino acids of env gp120 (HIV-1 Group O, HAM112 isolate), and 199 amino acids of env gp41 (HIV-1 Group O, HAM112 isolate). pGO-12CKS/XL1 was constructed as follows:

A PCR reaction (100 μl volume) was set up with UlTma DNA Polymerase (3 U) and 1× buffer along with 1.5 mM $MgCl_2$, 40 μM of each dNTP, 50 pmol of pTB/O-5' (SEQ ID NO:109), 50 pmol pGO-9/Kpn (SEQ ID NO:110), and 1 ng pGO-9PL DNA (miniprep H5; obtained from Example 3, Section F above) as template. The reaction was incubated at 94° C. for 105 seconds then amplified with 22 cycles of 94° C. for 30 seconds, 55° C. for 30 seconds, and 72° C. for 75 seconds, followed by incubation at 72° C. for 5 minutes. The pTB/O-5'/pGO-9/Kpn PCR product was isolated on gel. The pTB/O-5'/pGO-9/Kpn PCR product and pGM-1CKS plasmid (described in Section A hereinabove) were digested sequentially with Asp 718 (Boehringer Mannheim Biochemicals) and Bst XI. The digested vector was then treated with calf intestinal alkaline phosphatase (Boehringer Mannheim Biochemicals), extracted with phenol/chloroform, and precipitated with ethanol. The digested PCR product was purified on a Centri-Sep column (Princeton Separations). Digested PCR product was ligated into the digested and phosphatased pGM-1CKS vector overnight at 16° C. XL1-Blue supercompetent cells were transformed with the ligation product and plated on LB+ampicillin plates supplemented with 20 mM glucose. Colonies were restreaked for isolation on the same type of plates. An overnight culture (LB medium+100 μg/ml carbenicillin+20 mM glucose) of clone pGO-12CKS clone #1 was set up. Frozen stocks (0.5 ml 80% glycerol+0.5 ml overnight culture) were made and miniprep DNA was prepared for sequencing. The following oligonucleotides were used as primers for sequence analysis: CKS-1 (SEQ ID NO:30), CKS-2 (SEQ ID NO:31), CKS-3 (SEQ ID NO:32), CKS-4 (SEQ ID NO:33), CKS 176.1 (SEQ ID NO:19), 3962 (SEQ ID NO:111), 3965 (SEQ ID NO:113), pTB-S2 (SEQ ID NO:103), pTB-S3 (SEQ ID NO:104), pTB-S4 (SEQ ID NO:100), pTB-S5 (SEQ ID NO:105), sy120-S1 (SEQ ID NO:112), 41sy-1B (SEQ ID NO:29), 41sy-2B (SEQ ID NO:34), 41sy-4 (SEQ ID NO:23), pTB-S8 (SEQ ID NO:28). Based on the results of the sequence analysis, pGO-12CKS candidate clone #1 was designated as pGO-12CKS/XL1. (SEQ ID NO:90 presents the nucleotide sequence of the coding region, and SEQ ID NO:91 presents the encoded amino acid sequence.)

C. Construction of pGO-13CKS/XL1

The construct pGO-13CKS/XL1 encodes the recombinant protein pGO-13CKS, the amino acid sequence of which is shown in SEQ ID NO:93. This protein consists of 250 amino acids of CKS/polylinker fused to 42 amino acids of env gp120 (HIV-1 Group M, HXB2R isolate), 200 amino acids of env gp41 (HIV-1 Group M, HXB2R isolate), 45 amino acids of env gp120 (HIV-1 Group O, HAM112 isolate), and 169 amino acids of env gp41 (HIV-1 Group O, HAM112 isolate). pGO-13CKS/XL1 was constructed as follows:

A PCR reaction (100 μl volume) was set up with UlTma DNA Polymerase (3 U) and 1× buffer along with 1.5 mM $MgCl_2$, 40 μM of each dNTP, 50 pmol of pTB/O-5' (SEQ ID NO:109), 50 pmol pGO-8/Kpn (SEQ ID NO:114), and 1 ng pGO-9PL DNA (miniprep H5; obtained from Example 3, Section F hereinabove) as template. The reaction was incubated at 94° C. for 105 seconds then amplified with 22 cycles of 94° C. for 30 seconds, 55° C. for 30 seconds, and 72° C. for 75 seconds, followed by incubation at 72° C. for 5 minutes. The pTB/O-5'/pGO-8/Kpn PCR product was isolated on gel. The pTB/O-5'/pGO-8/Kpn PCR product and pGM-1CKS plasmid (described in Section A above) were digested sequentially with Asp 718 (Boehringer Mannheim Biochemicals) and Bst XI. The digested vector was then treated with calf intestinal alkaline phosphatase (Boehringer Mannheim Biochemicals), extracted with phenol/chloroform, and precipitated with ethanol. The digested PCR product was purified on a Centri-Sep column (Princeton Separations). Digested PCR product was ligated into the digested and phosphatased pGM-1CKS vector overnight at 16° C. XL1-Blue supercompetent cells were transformed with the ligation product and plated on LB+ampicillin plates supplemented with 20 mM glucose. Colonies were restreaked for isolation on the same type of plates. An overnight culture (LB medium+100 µg/ml carbenicillin+20 mM glucose) of clone pGO-13CKS clone #1 was set up. Frozen stocks (0.5 ml 80% glycerol+0.5 ml overnight culture) were made and miniprep DNA was prepared for sequencing. The following oligonucleotides were used as primers for sequence analysis: CKS-1 (SEQ ID NO:30), CKS-2 (SEQ ID NO:31), CKS-3 (SEQ ID NO:32), CKS-4 (SEQ ID NO:33), 43461 (SEQ ID NO:2), 43285 (SEQ ID NO:1), pTB-S1 (SEQ ID NO:102), pTB-S2 (SEQ ID NO:103), pTB-S3 (SEQ ID NO:104), pTB-S4 (SEQ ID NO:100), pTB-S5 (SEQ ID NO:105), sy120-S1 (SEQ ID NO:112), 41sy-1B (SEQ ID NO:29), 41sy-2B (SEQ ID NO:34), 41sy-4 (SEQ ID NO:23), pTB-S8 (SEQ ID NO:28). Based on the results of the sequence analysis, pGO-13CKS candidate clone #1 was designated as pGO-13CKS/XL1. (SEQ ID NO:92 presents the nucleotide sequence of the coding region, and SEQ ID NO:93 presents the encoded amino acid sequence.)

D. Construction of pGO-14PL/DH5α

The construct pGO-14PL/DH5α encodes the recombinant protein pGO-14PL, the amino acid sequence of which is shown in SEQ ID NO:95. This protein consists of an N-terminal methionine followed by 45 amino acids of env gp120 (HIV-1 Group O, HAM 12 isolate), 200 amino acids of env gp41 (HIV-1 Group O, HAM112 isolate) fused to 42 amino acids of env gp120 (HIV-1 Group M, HXB2R isolate), and 200 amino acids of env gp41 (HIV-1 Group M, HXB2R isolate). pGO-14PL/DH5α was constructed as follows:

A PCR reaction (100 µl volume) was set up with UlTma DNA Polymerase (3 U) and 1× buffer along with 1.5 mM MgCl₂, 40 µM of each dNTP, 50 pmol of pTB/Age5' (SEQ ID NO:115), 50 pmol pGO/B-3' (SEQ ID NO:116), and 1 ng pGM-1CKS DNA (miniprep of pTB319+A-#31; obtained from Section A above) as template. The reaction was incubated at 95° C. for 30 seconds then amplified with 22 cycles of 94° C. for 30 seconds, 55° C. for 30 seconds, and 72° C. for 60 seconds, followed by incubation at 72° C. for 5 minutes. The pTB/Age5'/pGO/B-3' PCR product was isolated on gel. The pTB/Age5'/pGO/B-3' PCR product and pGO-9PL plasmid (obtained from Example 3, Section F hereinabove) were digested sequentially with Age I and Bam HI. The digested vector was then treated with calf intestinal alkaline phosphatase (Boehringer Mannheim Biochemicals), extracted with phenol/chloroform, and precipitated with ethanol. The digested PCR product was purified on a Centri-Sep column (Princeton Separations). Digested PCR product was ligated into the digested and phosphatased pGM-1CKS vector overnight at 16° C. DH5α competent cells were transformed with the ligation product and plated on LB+ampicillin (150 µg/ml) plates. Colonies were analyzed for the presence of the proper insert by colony PCR using the vector primers pKRR EcoR1 forward (SEQ ID NO:38) and pKRR BamH1 reverse (SEQ ID NO:39). Colonies containing candidate clones were restreaked for isolation on the same type of plates. Overnight cultures (LB medium+100 µg/ml carbenicillin) were set up to generate frozen stocks and miniprep DNA. Frozen stocks (0.5 ml 80% glycerol+0.5 ml overnight culture) were made and miniprep DNA was prepared for sequencing. The following oligonucleotides were used as primers for sequence analysis: pTB-S1 (SEQ ID NO:102), pTB-S2 (SEQ ID NO:103), pTB-S3 (SEQ ID NO:104), pTB-S4 (SEQ ID NO:100), pTB-S5 (SEQ ID NO:105), 41sy-1C (SEQ ID NO:40), 41sy-2 (SEQ ID NO:41), 41sy-3 (SEQ ID NO:42), 41sy-4 (SEQ ID NO:23), pKRREcoR1 forward (SEQ ID NO:38), pKRR BamH1 reverse (SEQ ID NO:39). Based on the results of the sequence analysis, pGO-14PL candidate clone #11 was designated as pGO-14PL/DH5α. (SEQ ID NO:94 presents the nucleotide sequence of the coding region, and SEQ ID NO:95 presents the encoded amino acid sequence.)

Example 12

Construction of a HIV-1 Group O env gp120/gp41 Synthetic Gene with a Second Copy of the gp41 Immunodominant Region (IDR) Fused to the C-Terminus A. Construction of pGO-15CKS/XL1

The construct pGO-15CKS/XL1 encodes the recombinant protein pGO-15CKS, the amino acid sequence of which is shown in SEQ ID NO:97. This protein consists of 246 amino acids of CKS/polylinker fused to 45 amino acids of env gp120 (HIV-1 Group O, HAM112 isolate), 199 amino acids of env gp41 (HIV-1 Group O, HAM112 isolate), followed by a 4 amino acid linker (Gly, Gly, Gly, Ser) and 32 amino acids encompassing the IDR region of env gp41 (HIV-1 Group O, HAM112 isolate). pGO-15CKS/XL1 was constructed as follows:

The plasmid pGO-11CKS propagated in XL1-Blue cells (obtained from Example 3, Section K) was digested sequentially with Age I and Bam HI, extracted with phenol/chloroform, and precipitated with ethanol. The synthetic oligonucleotides synIDR#2-A (SEQ ID NO:117) and synIDR#2-B (SEQ ID NO:118) were kinased with polynucleotide kinase (Boehringer Mannheim Biochemicals) following the manufacturer's recommended procedure. The kinased oligonucleotides were annealed and the duplex ligated to the digested (Age I+Bam HI) pGO-11CKS vector. Supercompetent XL1-Blue cells were transformed with the ligation product, and the cells were plated on LB plates supplemented with 150 µg/ml ampicillin and incubated overnight. Colony PCR (primers 41sy-1B SEQ ID NO:29 and pTB-S8 SEQ ID NO:28) was used to identify candidate clones. Colonies were restreaked for isolation on LB plates supplemented with 150 µg/ml ampicillin. Overnight cultures of the candidate clones were established in 2×LB broth (Life Technologies, Inc.) supplemented with 100 mg/ml carbenicillin and 20 mM glucose (Sigma Chemical Co.). Miniprep DNA was prepared from the overnight cultures using a Promega 373 DNA isolation kit (Promega Corporation, Madison, Wis.) following the manufacturer's recommended procedure. The overnight cultures were also used to establish frozen stocks. Cells were pelleted and resuspended in 2×LB broth with 20% glycerol (J. T. Baker, Phillipsburg, N.J.) and frozen at −70° C. The following oligonucleotide primers were used for sequence analysis: CKS-1 (SEQ ID NO:30), CKS-3 (SEQ ID NO:32), 43285 (SEQ ID NO:1), 43461 (SEQ ID NO:2), 41sy-1B (SEQ ID NO:29), 41sy-2B (SEQ ID NO:34), 41sy-3B (SEQ ID NO:35), 41sy-4 (SEQ ID NO:23), and CKS3583 (SEQ ID NO:20). Based on sequencing results, candidate clone pGO-15CKS-48 was designated as pGO-15CKS/XL1. (SEQ ID NO:96 presents the nucleotide sequence of the coding region, and SEQ ID NO:97 presents the encoded amino acid sequence.)

B. Construction of pGO-15PL/DH5α.

The construct pGO-15PL/DH5α encodes the recombinant protein pGO-15PL, the amino acid sequence of which is shown in SEQ ID NO:120. This protein consists of an N-terminal methionine followed by 45 amino acids of env gp120 (HIV-1 Group O, HAM112 isolate), 199 amino acids of env gp41 (HIV-1 Group O, HAM112 isolate), a 4 amino acid linker (Gly, Gly, Gly, Ser) and 32 amino acids encompassing the IDR region of env gp41 (HIV-1 Group O, HAM112 isolate). pGO-15PL/DH5 was constructed as follows:

A PCR reaction (100 μl volume) was set up with AmpliTaq DNA Polymerase (2.5 U) and 1× buffer along with 40 μM of each dNTP, 50 pmol of 41sy-3B (SEQ ID NO:35), 50 pmol pTB-S8 (SEQ ID NO:28), and 1 ng pGO-15CKS DNA (miniprep of candidate clone pGO-15CKS-48; obtained from Section A above) as template. The reaction was incubated at 95° C. for 30 seconds, then amplified with 35 cycles of 94° C. for 20 seconds, 50° C. for 30 seconds, and 72° C. for 60 seconds, followed by incubation at 72° C. for 7 minutes. The amplified product was purified using a QIAquick PCR Purification Kit (Qiagen). The purified 41sy-3B/pTB-S8 amplification product was digested sequentially with Age I and Bam HI, then ligated to pGO-9PL (Age I+Bam HI digested/phosphatased vector prep from Example 3, Section J above). Competent DH5α cells were transformed using the ligation product and plated on LB plates supplemented with 150 μg/ml ampicillin. Candidate clones were identified by colony PCR with the primers 41sy-3 (SEQ ID NO:42) and pKRR BamHI reverse (SEQ ID NO:39), followed by digestion of the PCR product with Age I. Candidate clone #4 was restreaked for isolation. A culture of clone #4 was established in 2×LB broth (Life Technologies) supplemented with 100 μg/ml carbenicillin (Sigma Chemical Co.) and incubated at 34° C. overnight. Miniprep DNA was prepared from part of the overnight culture using a Promega 373 DNA Isolation Kit (Promega Corp.) as outlined by the manufacturer. Frozen stocks were established by pelleting the remaining overnight culture and resuspending the cells in Terrific Broth with 20% glycerol (J. T. Baker Co.) and freezing at −70° C. The following oligonucleotide primers were used for sequence analysis: pKRR EcoRI forward (SEQ ID NO:38), pKRR BamHI reverse (SEQ ID NO:39), 41sy-1C (SEQ ID NO:40), 41sy-2 (SEQ ID NO:41), 41sy-3 (SEQ ID NO:42), 41sy-3B (SEQ ID NO:35) and 41sy-4 (SEQ ID NO:23). Based on sequencing results, candidate pGO-15PL clone #4 was designated as pGO-15PL/DH5α. (SEQ ID NO:119 presents the nucleotide sequence of the coding region, and SEQ ID NO:120 presents the encoded amino acid sequence.)

Example 13

Preparation and Purification of HIV-1 Group O Recombinant gp41 Antigens pGO-8 PL, pGO-9 PL, pGO-12CKS, pGO-14 PL and pGO-15CKS The above antigens were prepared by growing and inducing *E. coli* strains containing the respective HIV-1 Group O recombinant gp41 antigen constructs as described in Example 5. The resulting frozen cells were resuspended by homogenization in cold lysis buffer comprising 50 mM Tris pH 8, 10 mM Na EDTA, 150 mM NaCl, 8% (w/v) sucrose, 5% Triton X-100® (v/v), 1 mM PMSF and 1 μM pepstatin A. Lysozyme was added to the homogenates at a concentration of 1.3 mg per gram of cells processed, and incubated for 30 minutes on ice to lyse the cells. Inclusion bodies were separated from soluble proteins by centrifugation. These pelleted inclusion bodies were washed and pelleted sequentially in 1) Lysis Buffer; 2) 10 mM Na EDTA pH 8, 30% (w/v) sucrose; and 3) water. The washed inclusion bodies were resuspended in 50 mM Tris pH 8, 10 mM Na EDTA, 150 mM NaCl and 3 M urea, and incubated on ice for 1 hour. The inclusion bodies then were separated from the solubilized proteins by centrifugation. The pelleted inclusion bodies were fully solubilized in 7 M guanidine-HCl, 50 mM Tris pH 8, 0.1% (v/v) beta-mercaptoethanol (BME) overnight at 4° C. The solubilized recombinant antigen(s) were clarified by centrifugation, passed through a 0.2 μm filter. The solubilized gp41 antigen(s) were precipitated from the 7 M Guanidine-HCl solution by dilution (1:7) with water to a final concentration of 1 M Guanidine-HCl. After incubation at 4° C. for 30 minutes, the precipitated proteins were centrifuged and resolubilized in 50 mM Tris pH 8, 9 M Urea, 0.1% BME (v/v) overnight at 4° C.

Solubilized HIV-1 Group O recombinant gp41 antigens were next purified as follows: The recombinant antigens were first purified by anion and/or cation exchange chromatography using Q-Sepharose (Pharmacia) or S-Sepharose (Pharmacia) columns. The solubilized gp41 antigen solutions were loaded onto either a Q-Sepharose or S-Sepharose column that had been previously equilibrated with 50 mM Tris pH 8, 8M Urea, 0.1% BME (v/v). The gp41 antigens either (1) passed though the column directly and were collected in the void volume or (2) were bound to the column matrix. If adsorbed, the gp41 antigens were eluted from the columns by a 0-1M NaCl gradient. SDS-polyacrylamide gel electrophoresis was used to analyze fractions from the Q-Sepharose or S-Sepharose columns. Fractions containing the recombinant gp41 antigens were pooled and then concentrated by ultrafiltration. The recombinant antigen concentrates were treated with 4% SDS (w/v) and 5% BME (w/v) at room temperature for three hours. SDS treated antigens were further purified by size exclusion chromatography on a Sephacryl S-300 (Pharmacia) column equilibrated with 25 mM Tris pH 8, 0.15 M NaCl, 0.1% v/v BME, 0.1% SDS (w/v). SDS-polyacrylamide gel electrophoresis was used to analyze the fractions from the S-300 column. Fractions containing purified recombinant antigens were pooled, passed through a 0.2 μm filter and stored at −70° C.

Example 14

Test of Recombinant Antigen Reactivity with HIV-1 Group M and Group O Samples A. Bead Coating In order to examine the reactivity of recombinant HIV-1 antigens, purified recombinants were coated on quarter inch polystyrene beads. These antigen coated beads were used in a series of capture assays to access reactivity to both HIV-1 Group M and Group O samples.

Recombinant antigens were coated on quarter inch beads at 0.5 μg/ml in PBS. The following recombinant antigens were coated: pTB319 (Group M), pGO-9/CKS, pGO-11/PL, pGO-12/CKS, pGO-14/PL and pGO-15/CKS (all Group O).

The procedure for coating the recombinant antigens on the beads is as follows: For each antigen, 35.5 gm. (~250) of beads, (Abbott Laboratories code 93-2556, lot 6840M100), were washed in 15% N-propanol in water for 30 minutes at 40° C. All incubations and washes were done in small brown glass jars on a shaker platform. The N-propanol solution was aspirated off, 58.25 ml of antigen solution was added, and the beads were incubated for two hours at 40° C. The antigen solution was aspirated off, and 60 ml of a 0.1% Triton X-100 solution in PBS was added for 30 minutes at 40° C. The beads were then washed with 60 ml of PBS two times and incubated with 60 ml of 2% BSA in PBS for 30 minutes at 40° C. The BSA was aspirated and the beads were washed again in PBS. The beads were then incubated with 60 ml 0.5% sucrose in PBS for 15 minutes at room temperature. After 15 minutes, the sucrose was aspirated and the beads were allowed to air dry. Coated beads were stored in polypropylene bottles with a desiccant at 4° C.

B. Assays

Recombinant antigen coated beads were tested for reactivity against a variety of samples using the Abbott Laboratories 3A11 kit (first generation, indirect assay format). Samples were diluted and added to wells in polystyrene trays. Beads were added and the trays were incubated at 40° C. for 1 hour. The trays were washed with water in an Abbott Laboratories QUICKWASH device. Next the kit conjugate, an anti-human IgG-Horseradish Peroxidase, was added and the trays were again incubated at 40° C. for one hour. The trays were again washed and 300 μl of substrate solution, (1.28 mg/ml o-Phenylenediamine-HCl in Citrate-Phosphate buffer containing 0.02% Hydrogen Peroxide), was added to each well for 30 minutes at room temperature. 1 ml of 1N sulfuric acid was added to stop the reaction, and the trays were read in an Abbott QUANTUM spectrophotometer.

The samples used for this study were Normal human plasma, (Abbott Laboratories code 99800, lot 17535M400), used as a negative control; HIVPL-31 (Group M positive sera), and the following Group O positive sera: 14283, 189404, 193Ha, 14791, 267Ha and ESP-1. All samples except the Normal human plasma control were run at three dilutions; 1:1,000, 1:10,000 and 1:100,000 in the kit specimen diluent. Each dilution of each sample was run in duplicate against each of the six beads, and the results of each dilution were averaged and plotted for each bead.

C. Results

The results of the above tests demonstrate the improvements in sensitivity and selectivity available by use of the recombinant antigens of the present invention. The bead coated with the HIV-1 Group M recombinant antigen (pTB319) detected the Group M serum sample, but failed to detect all but one of the Group O samples. The beads coated with only HIV-1 Group O recombinant antigens (pGO-9/CKS, pGO-11/PL, and PGO-15/CKS) detected the Group O serum samples, but showed lower sensitivity in detection of the HIV-1 Group M sample. Beads that were coated with hybrid Group M and Group O recombinant antigens (pGO-12/CKS, and pGO-14/PL) were able to detect both HIV-1 Group M- and Group O-positive samples. Lastly, pGO-15/CKS, which has an additional sequence representing the Group O immunodominant region of gp41 linked by recombinant means to the carboxy end of the protein, showed greater reactivity to low-titer Group O samples.

Example 15

Examination of Assay Sensitivity for HIV-1 Group O-Infected Samples Using Group O Recombinant Antigens pGO-9CKS and pGO-11CKS A. Assays In order to evaluate the performance in immunoassays of antigen constructs of the present invention, recombinant antigens pGO-9CKS and pGO-11CKS were incorporated into four HIV-1/HIV-2 immunoassays containing HIV-1 Group M (subtype B) reagents. The constructs were tested using one bead assay (Assay 1) and 3 automated microparticle-based assays (Assays 2-4). In all cases, the reactivity of HIV-1 Group O-infected specimens was assessed with (format 2) and without (format 1) incorporation of the HIV-1 group 0 recombinants. The coated beads/microparticles were reacted with multiple dilutions of the following HIV-1 Group O-positive human sera: ESP1, 189404, 193Ha, 341 Ha, 2156 and ABB 9/96.

For Assay 1, purified pGO-11CKS was incorporated into a commercially-available bead-based assay by coating the antigen construct onto quarter-inch polystyrene beads. The coated beads were reacted with a range of dilutions of HIV-1 Group O-positive human sera, washed, and then reacted with purified pGO-9CKS conjugated to horseradish peroxidase. After washing/separation of bound from unbound pGO-9CKS conjugate, substrate was added and the assay was completed as indicated in Example 14.

For Assay 2, purified pGO-11CKS was incorporated into a second commercially-available assay by coating the antigen construct onto microparticles. The coated microparticles were reacted with the same range of dilutions of HIV-1 Group O-positive human sera utilized in Assay 1. The microparticles were then washed and subsequently reacted with biotinylated pGO-9CKS. After further washing, the microparticles were reacted with a polyclonal anti-biotin antibody conjugated to alkaline phosphatase. The assay signal was developed by addition of the substrate methylumbelliferyl phosphate.

For Assay 3, purified pGO-11CKS was incorporated into a third commercially-available assay by coating the antigen construct on microparticles. The coated microparticles were again reacted with the same range of dilutions of HIV-1 Group O-positive human sera utilized in Assay 1. Next, the microparticles were washed and then reacted with biotinylated pGO-9CKS. After washing, the microparticles were reacted with an anti-biotin antibody conjugated to acridinium as the signal-generating compound.

For Assay 4, purified pGO-11CKS was incorporated into a developmental assay by coating the antigen construct onto magnetic microparticles. As in Assay 1, the coated microparticles were reacted with a range of dilutions of HIV-1 Group O-positive human sera, washed, and subsequently reacted with pGO-9CKS conjugated to acridinium.

B. Results

The results of the above tests are presented as signal/cutoff (S/CO) ratios. Format 1 refers to the conventional assay without the antigen constructs of the present invention, while Format 2 refers to the assay supplemented with the HIV-1 group O constructs.

From these data, it can be seen that the addition of the HIV-1 Group O recombinants resulted in a significant enhancement of assay sensitivity for the HIV-1 Group O-infected sera at all of the dilutions tested. For example, in the case of Assay 1 and sample 193Ha a S/CO ratio of 7.14 was obtained at a 1:10 dilution using Format 1, while a similar S/CO (7.22) was obtained at a 160-fold greater dilution (1:1600) using Format 2. This trend was maintained across all of the tested assay platforms. The utility of the group O recombinants was particularly evident for sample 2156, which tested negative (S/CO<1) in all 4 assays prior to the addition of the group O recombinants. With the addition of the HIV-1 Group O constructs, however, this sample 2156 tested positive in all four assays at a 1:400 dilution. In Assay 1, 2156 was still positive at a dilution of 1:5000. Addition of the recombinant reagents pGO-9CKS and pGO-11CKS was thus seen to provide a substantially better sensitivity for HIV-1 Group O-infected sera when using the above direct-format immunoassays.

SEQUENCE LISTING

<160> NUMBER OF SEQ ID NOS: 121

<210> SEQ ID NO 1
<211> LENGTH: 19
<212> TYPE: DNA
<213> ORGANISM: Human Immunodeficiency Virus
<220> FEATURE:
<223> OTHER INFORMATION: Sequencing Primer 43285

<400> SEQUENCE: 1
gagatcttca ggggtatcc                                                   19

<210> SEQ ID NO 2
<211> LENGTH: 20
<212> TYPE: DNA
<213> ORGANISM: Human Immunodeficiency Virus
<220> FEATURE:
<223> OTHER INFORMATION: Sequencing Primer 43461

<400> SEQUENCE: 2
ggatcatcgg ttcatcaccc                                                  20

<210> SEQ ID NO 3
<211> LENGTH: 114
<212> TYPE: DNA
<213> ORGANISM: Human Immunodeficiency Virus
<220> FEATURE:
<223> OTHER INFORMATION: Synthetic oligonucleotide (Osyn-A) for PCR

<400> SEQUENCE: 3
catgatcggt ggtgacatga aagacatctg gcgtaacgaa ctgttcaaat acaaagttgt      60
tcgtgttaaa ccgttctctg ttgctccgac cccgatcgct cgtccggtta tcgg           114

<210> SEQ ID NO 4
<211> LENGTH: 111
<212> TYPE: DNA
<213> ORGANISM: Human Immunodeficiency Virus
<220> FEATURE:
<223> OTHER INFORMATION: Synthetic oligonucleotide (Osyn-C) for PCR

<400> SEQUENCE: 4
gcaggttcca ctatgggtgc tgcagctacc gctctgaccg tacagaccca ctctgttatc 60
aaaggtatcg tacagcagca cgacaacctg ctgcgtgcaa tccaggcaca g 111

<210> SEQ ID NO 5
<211> LENGTH: 110
<212> TYPE: DNA
<213> ORGANISM: Human Immunodeficiency Virus
<220> FEATURE:
<223> OTHER INFORMATION: Synthetic oligonucleotide (Osyn-D) for PCR

<400> SEQUENCE: 5
agctgctggt tctggatcag ggtttccagt gccagcagac gagcacgcag ctgacggata 60
ccccatacag acagacgcag cagttcctgc tgtgcctgga ttgcacgcag 110

<210> SEQ ID NO 6
<211> LENGTH: 111
<212> TYPE: DNA
<213> ORGANISM: Human Immunodeficiency Virus
<220> FEATURE:
<223> OTHER INFORMATION: Synthetic oligonucleotide (Osyn-E) for PCR

<400> SEQUENCE: 6

-continued

```
ctgatccaga accagcagct gctgaacctg tggggctgca aaggtcgtct gatctgctac        60
acctccgtta aatggaacga aacctggcgt aacaccacca acatcaacca g                111

<210> SEQ ID NO 7
<211> LENGTH: 117
<212> TYPE: DNA
<213> ORGANISM: Human Immunodeficiency Virus
<220> FEATURE:
<223> OTHER INFORMATION: Synthetic oligonucleotide (Osyn-F) for PCR

<400> SEQUENCE: 7
ctgaacctga gctttctgga tttcttcgta gatggtggaa gaaacgttgt cgatctgctg        60
gtcccattcc tgccaggtca ggttacccca gatctggttg atgttggtgg tgttacg         117

<210> SEQ ID NO 8
<211> LENGTH: 101
<212> TYPE: DNA
<213> ORGANISM: Human Immunodeficiency Virus
<220> FEATURE:
<223> OTHER INFORMATION: Synthetic oligonucleotide (Osyn-G) for PCR

<400> SEQUENCE: 8
tccagaaagc tcaggttcag caggaacaga acgaaaaaaa actgctggaa ctggacgaat        60
gggcttctct gtggaactgg ctggacatca ccaaatggct g                          101

<210> SEQ ID NO 9
<211> LENGTH: 114
<212> TYPE: DNA
<213> ORGANISM: Human Immunodeficiency Virus
<220> FEATURE:
<223> OTHER INFORMATION: Synthetic oligonucleotide (Osyn-H) for PCR

<400> SEQUENCE: 9
accttcaccg gtacgacccg gagtttcagc ttcagactgc tgacgggtcg ggatctgcag        60
ggacagcggc tggtagccct gacggatgtt acgcagccat ttggtgatgt ccag            114

<210> SEQ ID NO 10
<211> LENGTH: 107
<212> TYPE: DNA
<213> ORGANISM: Human Immunodeficiency Virus
<220> FEATURE:
<223> OTHER INFORMATION: Synthetic oligonucleotide (Osyn-I) for PCR

<400> SEQUENCE: 10
cgggtcgtac cggtgaaggt ggtggtgacg aaggccgtcc gcgtctgatc ccgtctccgc        60
agggtttcct gccgctgctg tacaccgacc tgcgtaccat catcctg                    107

<210> SEQ ID NO 11
<211> LENGTH: 31
<212> TYPE: DNA
<213> ORGANISM: Human Immunodeficiency Virus
<220> FEATURE:
<223> OTHER INFORMATION: HIV-1 Group O PCR Primer Osyn-5' (outside)

<400> SEQUENCE: 11
ctacaagaat tccatgatcg gtggtgacat g                                      31

<210> SEQ ID NO 12
<211> LENGTH: 109
<212> TYPE: DNA
<213> ORGANISM: Human Immunodeficiency Virus
<220> FEATURE:
```

<223> OTHER INFORMATION: Synthetic oligonucleotide (Osyn-K) for PCR

<400> SEQUENCE: 12

```
gtctgtggat tctgggtcag aaaatcatcg acgcttgccg tatctgcgct gctgttatcc      60
actactggct gcaggaactg cagaaatccg ctacctccct gatcgacac                 109
```

<210> SEQ ID NO 13
<211> LENGTH: 114
<212> TYPE: DNA
<213> ORGANISM: Human Immunodeficiency Virus
<220> FEATURE:
<223> OTHER INFORMATION: Synthetic oligonucleotide (Osyn-L) for PCR

<400> SEQUENCE: 13

```
gcgaacacga cgcgggatgt tcaggatacc acgacccaga cgctggatac cacggatgat      60
gtcgtcagtc cagttagcaa ctgcaacagc gaaggtgtcg atcagggagg tagc           114
```

<210> SEQ ID NO 14
<211> LENGTH: 60
<212> TYPE: DNA
<213> ORGANISM: Human Immunodeficiency Virus
<220> FEATURE:
<223> OTHER INFORMATION: HIV-1 Group O PCR Primer Osyn-M (antisense)

<400> SEQUENCE: 14

```
atagtaggat cctattacag cagagagcgt tcgaagccct ggcgaacacg acgcgggatg      60
```

<210> SEQ ID NO 15
<211> LENGTH: 43
<212> TYPE: DNA
<213> ORGANISM: Human Immunodeficiency Virus
<220> FEATURE:
<223> OTHER INFORMATION: HIV-1 Group O PCR Primer Osyn-O3' (antisense)

<400> SEQUENCE: 15

```
atagtaggat cctattattc accggtacga cccggagttt cag                        43
```

<210> SEQ ID NO 16
<211> LENGTH: 38
<212> TYPE: DNA
<213> ORGANISM: Human Immunodeficiency Virus
<220> FEATURE:
<223> OTHER INFORMATION: HIV-1 Group O PCR Primer Osyn-P3' (antisense)

<400> SEQUENCE: 16

```
atagtaggat cctattacag ccatttggtg atgtccag                              38
```

<210> SEQ ID NO 17
<211> LENGTH: 106
<212> TYPE: DNA
<213> ORGANISM: Human Immunodeficiency Virus
<220> FEATURE:
<223> OTHER INFORMATION: Synthetic oligonucleotide (Osyn-B) for PCR

<400> SEQUENCE: 17

```
gcacccatag tggaacctgc tgcagacaga acgcccagga acagcatacc cagacctaca      60
gcacgttttt cacggtgggt gccagtaccg ataaccggac gagcga                   106
```

<210> SEQ ID NO 18
<211> LENGTH: 108
<212> TYPE: DNA
<213> ORGANISM: Human Immunodeficiency Virus
<220> FEATURE:
<223> OTHER INFORMATION: Synthetic oligonucleotide (Osyn-J) for PCR

```
<400> SEQUENCE: 18
ctgacccaga atccacagac ccagacgcag gtgagagata acagtctgag taccagagat       60
caggttagac agcaggtggt aggaccacag gatgatggta cgcaggtc                   108

<210> SEQ ID NO 19
<211> LENGTH: 26
<212> TYPE: DNA
<213> ORGANISM: Human Immunodeficiency Virus
<220> FEATURE:
<223> OTHER INFORMATION: Sequencing Primer CKS 176.1

<400> SEQUENCE: 19
gcagcttcgt gttctgtggt acggcg                                            26

<210> SEQ ID NO 20
<211> LENGTH: 19
<212> TYPE: DNA
<213> ORGANISM: Human Immunodeficiency Virus
<220> FEATURE:
<223> OTHER INFORMATION: Sequencing Primer CKS3583

<400> SEQUENCE: 20
cgtaacggta cgacactcc                                                    19

<210> SEQ ID NO 21
<211> LENGTH: 26
<212> TYPE: DNA
<213> ORGANISM: Human Immunodeficiency Virus
<220> FEATURE:
<223> OTHER INFORMATION: PCR Primer IM-6F (Forward)

<400> SEQUENCE: 21
ccgctacctc cctgatcgac accttc                                            26

<210> SEQ ID NO 22
<211> LENGTH: 26
<212> TYPE: DNA
<213> ORGANISM: Human Immunodeficiency Virus
<220> FEATURE:
<223> OTHER INFORMATION: PCR Primer IM-6R (Reverse)

<400> SEQUENCE: 22
gaaggtgtcg atcagggagg tagcgg                                            26

<210> SEQ ID NO 23
<211> LENGTH: 19
<212> TYPE: DNA
<213> ORGANISM: Human Immunodeficiency Virus
<220> FEATURE:
<223> OTHER INFORMATION: PCR Primer 41sy-4

<400> SEQUENCE: 23
gatgtccagc cagttccac                                                    19

<210> SEQ ID NO 24
<211> LENGTH: 64
<212> TYPE: DNA
<213> ORGANISM: Human Immunodeficiency Virus
<220> FEATURE:
<223> OTHER INFORMATION: Synthetic oligonucleotide (Osyn-5' repair) for
      PCR

<400> SEQUENCE: 24
ctacaagaat tccatgatcg gtggtgacat gaaagacatc tggcgtaacg aactgttcaa       60
```

<210> SEQ ID NO 25
<211> LENGTH: 34
<212> TYPE: DNA
<213> ORGANISM: Human Immunodeficiency Virus
<220> FEATURE:
<223> OTHER INFORMATION: PCR Primer Osyn-5'CKS

<400> SEQUENCE: 25
ctacaagaat tctatcggtg gtgacatgaa agac                          34

<210> SEQ ID NO 26
<211> LENGTH: 20
<212> TYPE: DNA
<213> ORGANISM: Human Immunodeficiency Virus
<220> FEATURE:
<223> OTHER INFORMATION: PCR Primer I-PCR

<400> SEQUENCE: 26
cgggtcgtac cggtgaaggt                                          20

<210> SEQ ID NO 27
<211> LENGTH: 23
<212> TYPE: DNA
<213> ORGANISM: Human Immunodeficiency Virus
<220> FEATURE:
<223> OTHER INFORMATION: PCR Primer M-PCR

<400> SEQUENCE: 27
atagtaggat cctattacag cag                                      23

<210> SEQ ID NO 28
<211> LENGTH: 19
<212> TYPE: DNA
<213> ORGANISM: Human Immunodeficiency Virus
<220> FEATURE:
<223> OTHER INFORMATION: Sequencing Primer pTB-S8

<400> SEQUENCE: 28
gccggaagcg agaagaatc                                           19

<210> SEQ ID NO 29
<211> LENGTH: 19
<212> TYPE: DNA
<213> ORGANISM: Human Immunodeficiency Virus
<220> FEATURE:
<223> OTHER INFORMATION: Sequencing Primer 41sy-1B

<400> SEQUENCE: 29
tatcgtacag cagcaggac                                           19

<210> SEQ ID NO 30
<211> LENGTH: 21
<212> TYPE: DNA
<213> ORGANISM: Human Immunodeficiency Virus
<220> FEATURE:
<223> OTHER INFORMATION: Sequencing Primer CKS-1

<400> SEQUENCE: 30
cccattaatg tgagttagct c                                        21

<210> SEQ ID NO 31
<211> LENGTH: 20
<212> TYPE: DNA

```
<213> ORGANISM: Human Immunodeficiency Virus
<220> FEATURE:
<223> OTHER INFORMATION: Sequencing Primer CKS-2

<400> SEQUENCE: 31
cctgacgaat gattgtcgca                                              20

<210> SEQ ID NO 32
<211> LENGTH: 19
<212> TYPE: DNA
<213> ORGANISM: Human Immunodeficiency Virus
<220> FEATURE:
<223> OTHER INFORMATION: Sequencing Primer CKS-3

<400> SEQUENCE: 32
attcagcgac gacacggtg                                               19

<210> SEQ ID NO 33
<211> LENGTH: 18
<212> TYPE: DNA
<213> ORGANISM: Human Immunodeficiency Virus
<220> FEATURE:
<223> OTHER INFORMATION: Sequencing Primer CKS-4

<400> SEQUENCE: 33
gtatccacac ctgtgcca                                                18

<210> SEQ ID NO 34
<211> LENGTH: 19
<212> TYPE: DNA
<213> ORGANISM: Human Immunodeficiency Virus
<220> FEATURE:
<223> OTHER INFORMATION: Sequencing Primer 41sy-2B

<400> SEQUENCE: 34
agagtgggtc tgtacggtc                                               19

<210> SEQ ID NO 35
<211> LENGTH: 20
<212> TYPE: DNA
<213> ORGANISM: Human Immunodeficiency Virus
<220> FEATURE:
<223> OTHER INFORMATION: Sequencing Primer 41sy-3B

<400> SEQUENCE: 35
aatgggcttc tctgtggaac                                              20

<210> SEQ ID NO 36
<211> LENGTH: 20
<212> TYPE: DNA
<213> ORGANISM: Human Immunodeficiency Virus
<220> FEATURE:
<223> OTHER INFORMATION: Sequencing Primer 41sy-5C

<400> SEQUENCE: 36
ctgtctaacc tgatctctgg                                              20

<210> SEQ ID NO 37
<211> LENGTH: 20
<212> TYPE: DNA
<213> ORGANISM: Human Immunodeficiency Virus
<220> FEATURE:
<223> OTHER INFORMATION: Sequencing Primer 41sy-6B

<400> SEQUENCE: 37
acgcaggtga gagataacag                                              20
```

<210> SEQ ID NO 38
<211> LENGTH: 22
<212> TYPE: DNA
<213> ORGANISM: Human Immunodeficiency Virus
<220> FEATURE:
<223> OTHER INFORMATION: PCR Primer pKRREcoR1 (Forward)

<400> SEQUENCE: 38
gtgatacgaa acgaagcatt gg                                    22

<210> SEQ ID NO 39
<211> LENGTH: 21
<212> TYPE: DNA
<213> ORGANISM: Human Immunodeficiency Virus
<220> FEATURE:
<223> OTHER INFORMATION: PCR Primer pKRRBamHI (Reverse)

<400> SEQUENCE: 39
gcgatatagg cgccagcaac c                                     21

<210> SEQ ID NO 40
<211> LENGTH: 21
<212> TYPE: DNA
<213> ORGANISM: Human Immunodeficiency Virus
<220> FEATURE:
<223> OTHER INFORMATION: PCR Primer 41sy-1C

<400> SEQUENCE: 40
ctctgttatc aaaggtatcg t                                     21

<210> SEQ ID NO 41
<211> LENGTH: 18
<212> TYPE: DNA
<213> ORGANISM: Human Immunodeficiency Virus
<220> FEATURE:
<223> OTHER INFORMATION: PCR Primer 41sy-2

<400> SEQUENCE: 41
agcagacgag cacgcagc                                         18

<210> SEQ ID NO 42
<211> LENGTH: 18
<212> TYPE: DNA
<213> ORGANISM: Human Immunodeficiency Virus
<220> FEATURE:
<223> OTHER INFORMATION: PCR Primer 41sy-3

<400> SEQUENCE: 42
ttcagcagga acagaacg                                         18

<210> SEQ ID NO 43
<211> LENGTH: 18
<212> TYPE: DNA
<213> ORGANISM: Human Immunodeficiency Virus
<220> FEATURE:
<223> OTHER INFORMATION: PCR Primer 41sy-5B

<400> SEQUENCE: 43
tccgcgtctg atcccgtc                                         18

<210> SEQ ID NO 44
<211> LENGTH: 17
<212> TYPE: DNA
<213> ORGANISM: Human Immunodeficiency Virus
<220> FEATURE:

<223> OTHER INFORMATION: PCR Primer 41sy-1

<400> SEQUENCE: 44
ccaggcacag caggaac                                                        17

<210> SEQ ID NO 45
<211> LENGTH: 20
<212> TYPE: DNA
<213> ORGANISM: Human Immunodeficiency Virus
<220> FEATURE:
<223> OTHER INFORMATION: Sequencing Primer 56759

<400> SEQUENCE: 45
acactataga atactcaagc                                                     20

<210> SEQ ID NO 46
<211> LENGTH: 20
<212> TYPE: DNA
<213> ORGANISM: Human Immunodeficiency Virus
<220> FEATURE:
<223> OTHER INFORMATION: Sequencing Primer 55848

<400> SEQUENCE: 46
taatacgact cactataggg                                                     20

<210> SEQ ID NO 47
<211> LENGTH: 741
<212> TYPE: DNA
<213> ORGANISM: Human Immunodeficiency Virus
<220> FEATURE:
<223> OTHER INFORMATION: Nucleotide sequence of the coding region of
      pGO-9PL

<400> SEQUENCE: 47
atgatcggtg gtgacatgaa agacatctgg cgtaacgaac tgttcaaata caaagttgtt         60
cgtgttaaac cgttctctgt tgctccgacc ccgatcgctc gtccggttat cggtactggc        120
acccaccgtg aaaaacgtgc tgtaggtctg gtatgctgt tcctgggcgt tctgtctgca         180
gcaggttcca ctatgggtgc tgcagctacc gctctgaccg tacagaccca ctctgttatc        240
aaaggtatcg tacagcagca ggacaacctg ctgcgtgcaa tccaggcaca gcaggaactg        300
ctgcgtctgt ctgtatgggg tatccgtcag ctgcgtgctc gtctgctggc actggaaacc        360
ctgatccaga accagcagct gctgaacctg tggggctgca aggtcgtct gatctgctac         420
acctccgtta atggaacga aacctggcgt aacaccacca acatcaacca gatctggggt        480
aacctgacct ggcaggaatg ggaccagcag atcgacaacg tttcttccac catctacgaa        540
gaaatccaga agctcaggt tcagcaggaa cagaacgaaa aaaaactgct ggaactggac        600
gaatgggctt ctctgtggaa ctggctggac atcaccaaat ggctgcgtaa catccgtcag        660
ggctaccagc cgctgtccct gcagatcccg acccgtcagc agtctgaagc tgaaactccg        720
ggtcgtaccg tgaataata g                                                  741

<210> SEQ ID NO 48
<211> LENGTH: 245
<212> TYPE: PRT
<213> ORGANISM: Human Immunodeficiency Virus
<220> FEATURE:
<223> OTHER INFORMATION: Encodes recombinant protein pGO-9PL

<400> SEQUENCE: 48

Met Ile Gly Gly Asp Met Lys Asp Ile Trp Arg Asn Glu Leu Phe Lys
1               5                   10                  15

Tyr Lys Val Val Arg Val Lys Pro Phe Ser Val Ala Pro Thr Pro Ile
            20                  25                  30

Ala Arg Pro Val Ile Gly Thr Gly Thr His Arg Glu Lys Arg Ala Val
        35                  40                  45

Gly Leu Gly Met Leu Phe Leu Gly Val Leu Ser Ala Ala Gly Ser Thr
    50                  55                  60

Met Gly Ala Ala Ala Thr Ala Leu Thr Val Gln Thr His Ser Val Ile
65                  70                  75                  80

Lys Gly Ile Val Gln Gln Gln Asp Asn Leu Leu Arg Ala Ile Gln Ala
                85                  90                  95

Gln Gln Glu Leu Leu Arg Leu Ser Val Trp Gly Ile Arg Gln Leu Arg
            100                 105                 110

Ala Arg Leu Leu Ala Leu Glu Thr Leu Ile Gln Asn Gln Gln Leu Leu
        115                 120                 125

Asn Leu Trp Gly Cys Lys Gly Arg Leu Ile Cys Tyr Thr Ser Val Lys
    130                 135                 140

Trp Asn Glu Thr Trp Arg Asn Thr Thr Asn Ile Asn Gln Ile Trp Gly
145                 150                 155                 160

Asn Leu Thr Trp Gln Glu Trp Asp Gln Gln Ile Asp Asn Val Ser Ser
                165                 170                 175

Thr Ile Tyr Glu Glu Ile Gln Lys Ala Gln Val Gln Gln Glu Gln Asn
            180                 185                 190

Glu Lys Lys Leu Leu Glu Leu Asp Glu Trp Ala Ser Leu Trp Asn Trp
        195                 200                 205

Leu Asp Ile Thr Lys Trp Leu Arg Asn Ile Arg Gln Gly Tyr Gln Pro
    210                 215                 220

Leu Ser Leu Gln Ile Pro Thr Arg Gln Gln Ser Glu Ala Glu Thr Pro
225                 230                 235                 240

Gly Arg Thr Gly Glu
            245

<210> SEQ ID NO 49
<211> LENGTH: 1476
<212> TYPE: DNA
<213> ORGANISM: Human Immunodeficiency Virus
<220> FEATURE:
<223> OTHER INFORMATION: Nucleotide sequence of the coding region of
      pGO-9CKS

<400> SEQUENCE: 49
atgagttttg tggtcattat tcccgcgcgc tacgcgtcga cgcgtctgcc cggtaaacca      60
ttggttgata ttaacggcaa acccatgatt gttcatgttc ttaacgcgcg cgtgaatca     120 ggtgccgagc gcatcatcgt ggcaaccgat catgaggatg ttgcccgcgc cgttgaagcc    180
gctggcggtg aagtatgtat gacgcgcgcc gatcatcagt caggaacaga acgtctggcg    240
gaagttgtcg aaaaatgcgc attcagcgac gacacggtga tcgttaatgt gcagggtgat    300
gaaccgatga tccctgcgac aatcattcgt caggttgctg ataacctcgc tcagcgtcag    360
gtgggtatga cgactctggc ggtgccaatc cacaatgcgg aagaagcgtt taacccgaat    420
gcggtgaaag tggttctcga cgctgaaggg tatgcactgt acttctctcg cgccaccatt    480
ccttgggatc gtgatcgttt tgcagaaggc cttgaaaccg ttggcgataa cttcctgcgt    540
catcttggta tttatggcta ccgtgcaggc tttatccgtc gttacgtcaa ctggcagcca    600
agtccgttag aacacatcga aatgttagag cagcttcgtg ttctgtggta cggcgaaaaa    660

```
atccatgttg ctgttgctca ggaagttcct ggcacaggtg tggataccccc tgaagatctc      720 gacccgtcga cgaattctat cggtggtgac atgaaagaca tctggcgtaa cgaactgttc      780
aaatacaaag ttgttcgtgt taaaccgttc tctgttgctc cgaccccgat cgctcgtccg      840
gttatcggta ctggcaccca ccgtgaaaaa cgtgctgtag gtctgggtat gctgttcctg      900
ggcgttctgt ctgcagcagg ttccactatg ggtgctgcag ctaccgctct gaccgtacag      960
acccactctg ttatcaaagg tatcgtacag cagcaggaca acctgctgcg tgcaatccag     1020
gcacagcagg aactgctgcg tctgtctgta tggggtatcc gtcagctgcg tgctcgtctg     1080
ctggcactgg aaaccctgat ccagaaccag cagctgctga acctgtgggg ctgcaaaggt     1140
cgtctgatct gctacacctc cgttaaatgg aacgaaacct ggcgtaacac caccaacatc     1200
aaccagatct ggggtaacct gacctggcag gaatgggacc agcagatcga caacgtttct     1260
tccaccatct acgaagaaat ccagaaagct caggttcagc aggaacagaa cgaaaaaaaa     1320
ctgctggaac tggacgaatg gcttctctg tggaactggc tggacatcac caatggctg      1380 cgtaacatcc gtcagggcta ccagccgctg tccctgcaga tcccgacccg tcagcagtct     1440
gaagctgaaa ctccgggtcg taccggtgaa taatag                               1476
```

<210> SEQ ID NO 50
<211> LENGTH: 490
<212> TYPE: PRT
<213> ORGANISM: Human Immunodeficiency Virus
<220> FEATURE:
<223> OTHER INFORMATION: Encodes recombinant protein pGO-9CKS

<400> SEQUENCE: 50

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220
```

```
Val Ala Gln Glu Val Pro Gly Thr Gly Val Asp Thr Pro Glu Asp Leu
225                 230                 235                 240

Asp Pro Ser Thr Asn Ser Ile Gly Gly Asp Met Lys Asp Ile Trp Arg
            245                 250                 255

Asn Glu Leu Phe Lys Tyr Lys Val Val Arg Val Lys Pro Phe Ser Val
        260                 265                 270

Ala Pro Thr Pro Ile Ala Arg Pro Val Ile Gly Thr Gly Thr His Arg
    275                 280                 285

Glu Lys Arg Ala Val Gly Leu Gly Met Leu Phe Leu Gly Val Leu Ser
290                 295                 300

Ala Ala Gly Ser Thr Met Gly Ala Ala Thr Ala Leu Thr Val Gln
305                 310                 315                 320

Thr His Ser Val Ile Lys Gly Ile Val Gln Gln Asp Asn Leu Leu
            325                 330                 335

Arg Ala Ile Gln Ala Gln Gln Glu Leu Leu Arg Leu Ser Val Trp Gly
        340                 345                 350

Ile Arg Gln Leu Arg Ala Arg Leu Leu Ala Leu Glu Thr Leu Ile Gln
    355                 360                 365

Asn Gln Gln Leu Leu Asn Leu Trp Gly Cys Lys Gly Arg Leu Ile Cys
370                 375                 380

Tyr Thr Ser Val Lys Trp Asn Glu Thr Trp Arg Asn Thr Thr Asn Ile
385                 390                 395                 400

Asn Gln Ile Trp Gly Asn Leu Thr Trp Gln Glu Trp Asp Gln Ile
            405                 410                 415

Asp Asn Val Ser Ser Thr Ile Tyr Glu Glu Ile Gln Lys Ala Gln Val
        420                 425                 430

Gln Gln Glu Gln Asn Glu Lys Lys Leu Leu Glu Leu Asp Glu Trp Ala
    435                 440                 445

Ser Leu Trp Asn Trp Leu Asp Ile Thr Lys Trp Leu Arg Asn Ile Arg
450                 455                 460

Gln Gly Tyr Gln Pro Leu Ser Leu Gln Ile Pro Thr Arg Gln Gln Ser
465                 470                 475                 480

Glu Ala Glu Thr Pro Gly Arg Thr Gly Glu
            485                 490

<210> SEQ ID NO 51
<211> LENGTH: 1125
<212> TYPE: DNA
<213> ORGANISM: Human Immunodeficiency Virus
<220> FEATURE:
<223> OTHER INFORMATION: Nucleotide sequence of the coding region of
      pGO-11PL

<400> SEQUENCE: 51
atgatcggtg gtgacatgaa agacatctgg cgtaacgaac tgttcaaata caaagttgtt      60
cgtgttaaac cgttctctgt tgctccgacc ccgatcgctc gtccggttat cggtactggc    120
acccaccgtg aaaaacgtgc tgtaggtctg ggtatgctgt tcctgggcgt tctgtctgca    180
gcaggttcca ctatgggtgc tgcagctacc gctctgaccg tacagaccca ctctgttatc    240
aaaggtatcg tacagcagca ggacaacctg ctgcgtgcaa tccaggcaca gcaggaactg    300
ctgcgtctgt ctgtatgggg tatccgtcag ctgcgtgctc gtctgctggc actggaaacc    360
ctgatccaga accagcagct gctgaacctg tggggctgca aggtcgtct gatctgctac    420 acctccgtta aatggaacga aacctggcgt aacaccacca catcaacca gatctgggt     480
```

-continued

```
aacctgacct ggcaggaatg ggaccagcag atcgacaacg tttcttccac catctacgaa    540
gaaatccaga aagctcaggt tcagcaggaa cagaacgaaa aaaaactgct ggaactggac    600
gaatgggctt ctctgtggaa ctggctggac atcaccaaat ggctgcgtaa catccgtcag    660
ggctaccagc cgctgtccct gcagatcccg acccgtcagc agtctgaagc tgaaactccg    720
ggtcgtaccg gtgaaggtgg tggtgacgaa ggccgtccgc gtctgatccc gtctccgcag    780
ggtttcctgc cgctgctgta caccgacctg cgtaccatca tcctgtggtc ctaccacctg    840
ctgtctaacc tgatctctgg tactcagact gttatctctc acctgcgtct gggtctgtgg    900
attctgggtc agaaaatcat cgacgcttgc cgtatctgcg ctgctgttat ccactactgg    960
ctgcaggaac tgcagaaatc cgctacctcc ctgatcgaca ccttcgctgt tgcagttgct   1020
aactggactg acgacatcat cctgggtatc cagcgtctgg gtcgtggtat cctgaacatc   1080
ccgcgtcgtg ttcgccaggg cttcgaacgc tctctgctgt aatag                  1125
```

<210> SEQ ID NO 52
<211> LENGTH: 373
<212> TYPE: PRT
<213> ORGANISM: Human Immunodeficiency Virus
<220> FEATURE:
<223> OTHER INFORMATION: Encodes recombinant protein pGO-11PL

<400> SEQUENCE: 52

```
Met Ile Gly Gly Asp Met Lys Asp Ile Trp Arg Asn Glu Leu Phe Lys
  1               5                  10                  15

Tyr Lys Val Val Arg Val Lys Pro Phe Ser Val Ala Pro Thr Pro Ile
             20                  25                  30

Ala Arg Pro Val Ile Gly Thr Gly Thr His Arg Glu Lys Arg Ala Val
         35                  40                  45

Gly Leu Gly Met Leu Phe Leu Gly Val Leu Ser Ala Ala Gly Ser Thr
     50                  55                  60

Met Gly Ala Ala Ala Thr Ala Leu Thr Val Gln Thr His Ser Val Ile
 65                  70                  75                  80

Lys Gly Ile Val Gln Gln Gln Asp Asn Leu Leu Arg Ala Ile Gln Ala
                 85                  90                  95

Gln Gln Glu Leu Leu Arg Leu Ser Val Trp Gly Ile Arg Gln Leu Arg
            100                 105                 110

Ala Arg Leu Leu Ala Leu Glu Thr Leu Ile Gln Asn Gln Gln Leu Leu
        115                 120                 125

Asn Leu Trp Gly Cys Lys Gly Arg Leu Ile Cys Tyr Thr Ser Val Lys
    130                 135                 140

Trp Asn Glu Thr Trp Arg Asn Thr Thr Asn Ile Asn Gln Ile Trp Gly
145                 150                 155                 160

Asn Leu Thr Trp Gln Glu Trp Asp Gln Gln Ile Asp Asn Val Ser Ser
                165                 170                 175

Thr Ile Tyr Glu Glu Ile Gln Lys Ala Gln Val Gln Gln Glu Gln Asn
            180                 185                 190

Glu Lys Lys Leu Leu Glu Leu Asp Glu Trp Ala Ser Leu Trp Asn Trp
        195                 200                 205

Leu Asp Ile Thr Lys Trp Leu Arg Asn Ile Arg Gln Gly Tyr Gln Pro
    210                 215                 220

Leu Ser Leu Gln Ile Pro Thr Arg Gln Gln Ser Glu Ala Glu Thr Pro
225                 230                 235                 240

Gly Arg Thr Gly Glu Gly Gly Gly Asp Glu Gly Arg Pro Arg Leu Ile
                245                 250                 255
```

```
Pro Ser Pro Gln Gly Phe Leu Pro Leu Leu Tyr Thr Asp Leu Arg Thr
        260                 265                 270

Ile Ile Leu Trp Ser Tyr His Leu Leu Ser Asn Leu Ile Ser Gly Thr
            275                 280                 285

Gln Thr Val Ile Ser His Leu Arg Leu Gly Leu Trp Ile Leu Gly Gln
        290                 295                 300

Lys Ile Ile Asp Ala Cys Arg Ile Cys Ala Ala Val Ile His Tyr Trp
305                 310                 315                 320

Leu Gln Glu Leu Gln Lys Ser Ala Thr Ser Leu Ile Asp Thr Phe Ala
                325                 330                 335

Val Ala Val Ala Asn Trp Thr Asp Asp Ile Ile Leu Gly Ile Gln Arg
            340                 345                 350

Leu Gly Arg Gly Ile Leu Asn Ile Pro Arg Arg Val Arg Gln Gly Phe
        355                 360                 365

Glu Arg Ser Leu Leu
    370

<210> SEQ ID NO 53
<211> LENGTH: 1860
<212> TYPE: DNA
<213> ORGANISM: Human Immunodeficiency Virus
<220> FEATURE:
<223> OTHER INFORMATION: Nucleotide sequence of the coding region of
      pGO-11CKS

<400> SEQUENCE: 53
atgagttttg tggtcattat tcccgcgcgc tacgcgtcga cgcgtctgcc cggtaaacca      60
ttggttgata ttaacggcaa acccatgatt gttcatgttc ttaacgcgc gcgtgaatca     120 ggtgccgagc gcatcatcgt ggcaaccgat catgaggatg ttgcccgcgc cgttgaagcc     180
gctggcggtg aagtatgtat gacgcgcgcc gatcatcagt caggaacaga acgtctggcg     240
gaagttgtcg aaaaatgcgc attcagcgac gacacggtga tcgttaatgt gcagggtgat     300
gaaccgatga tccctgcgac aatcattcgt caggttgctg ataacctcgc tcagcgtcag     360
gtgggtatga cgactctggc ggtgccaatc cacaatgcgg aagaagcgtt taacccgaat     420
gcggtgaaag tggttctcga cgctgaaggg tatgcactgt acttctctcg cgccaccatt     480
ccttgggatc gtgatcgttt tgcagaaggc cttgaaaccg ttggcgataa cttcctgcgt     540
catcttggta tttatggcta ccgtgcaggc tttatccgtc gttacgtcaa ctggcagcca     600
agtccgttag aacacatcga aatgttagag cagcttcgtg ttctgtggta cggcgaaaaa     660
atccatgttg ctgttgctca ggaagttcct ggcacaggtg tggatacccc tgaagatctc     720
gacccgtcga cgaattctat cggtggtgac atgaaagaca tctggcgtaa cgaactgttc     780
aaatacaaag ttgttcgtgt taaaccgttc tctgttgctc cgaccccgat cgctcgtccg     840
gttatcggta ctggcaccca ccgtgaaaaa cgtgctgtag gtctgggtat gctgttcctg     900
ggcgttctgt ctgcagcagg ttccactatg ggtgctgcag ctaccgctct gaccgtacag     960
acccactctg ttatcaaagg tatcgtacag cagcaggaca acctgctgcg tgcaatccag    1020
gcacagcagg aactgctgcg tctgtctgta tggggtatcc gtcagctgcg tgctcgtctg    1080
ctggcactgg aaaccctgat ccagaaccag cagctgctga acctgtgggg ctgcaaaggt    1140
cgtctgatct gctacacctc cgttaaatgg aacgaaacct ggcgtaacac caccaacatc    1200
aaccagatct ggggtaacct gacctggcag gaatgggacc agcagatcga caacgttttct    1260 tccaccatct acgaagaaat ccagaaagct caggttcagc aggaacagaa cgaaaaaaaa    1320
```

-continued

```
ctgctggaac tggacgaatg ggcttctctg tggaactggc tggacatcac caaatggctg    1380
cgtaacatcc gtcagggcta ccagccgctg tccctgcaga tcccgacccg tcagcagtct    1440
gaagctgaaa ctccgggtcg taccggtgaa ggtggtggtg acgaaggccg tccgcgtctg    1500
atcccgtctc cgcagggttt cctgccgctg ctgtacaccg acctgcgtac catcatcctg    1560
tggtcctacc acctgctgtc taacctgatc tctggtactc agactgttat ctctcacctg    1620
cgtctgggtc tgtggattct gggtcagaaa atcatcgacg cttgccgtat ctgcgctgct    1680
gttatccact actggctgca ggaactgcag aaatccgcta cctccctgat cgacaccttc    1740
gctgttgcag ttgctaactg gactgacgac atcatcctgg gtatccagcg tctgggtcgt    1800
ggtatcctga acatcccgcg tcgtgttcgc cagggcttcg aacgctctct gctgtaatag    1860
```

<210> SEQ ID NO 54
<211> LENGTH: 618
<212> TYPE: PRT
<213> ORGANISM: Human Immunodeficiency Virus
<220> FEATURE:
<223> OTHER INFORMATION: Encodes recombinant protein pGO-11CKS

<400> SEQUENCE: 54

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
     50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Ile Gly Gly Asp Met Lys Asp Ile Trp Arg
                245                 250                 255

Asn Glu Leu Phe Lys Tyr Lys Val Val Arg Val Lys Pro Phe Ser Val
            260                 265                 270
```

```
Ala Pro Thr Pro Ile Ala Arg Pro Val Ile Gly Thr Gly Thr His Arg
        275                 280                 285

Glu Lys Arg Ala Val Gly Leu Gly Met Leu Phe Leu Gly Val Leu Ser
    290                 295                 300

Ala Ala Gly Ser Thr Met Gly Ala Ala Thr Ala Leu Thr Val Gln
305                 310                 315                 320

Thr His Ser Val Ile Lys Gly Ile Val Gln Gln Asp Asn Leu Leu
                325                 330                 335

Arg Ala Ile Gln Ala Gln Gln Glu Leu Leu Arg Leu Ser Val Trp Gly
            340                 345                 350

Ile Arg Gln Leu Arg Ala Arg Leu Leu Ala Leu Glu Thr Leu Ile Gln
        355                 360                 365

Asn Gln Gln Leu Leu Asn Leu Trp Gly Cys Lys Gly Arg Leu Ile Cys
    370                 375                 380

Tyr Thr Ser Val Lys Trp Asn Glu Thr Trp Arg Asn Thr Thr Asn Ile
385                 390                 395                 400

Asn Gln Ile Trp Gly Asn Leu Thr Trp Gln Glu Trp Asp Gln Ile
                405                 410                 415

Asp Asn Val Ser Ser Thr Ile Tyr Glu Glu Ile Gln Lys Ala Gln Val
            420                 425                 430

Gln Gln Glu Gln Asn Glu Lys Lys Leu Leu Glu Leu Asp Glu Trp Ala
        435                 440                 445

Ser Leu Trp Asn Trp Leu Asp Ile Thr Lys Trp Leu Arg Asn Ile Arg
    450                 455                 460

Gln Gly Tyr Gln Pro Leu Ser Leu Gln Ile Pro Thr Arg Gln Gln Ser
465                 470                 475                 480

Glu Ala Glu Thr Pro Gly Arg Thr Gly Glu Gly Gly Gly Asp Glu Gly
                485                 490                 495

Arg Pro Arg Leu Ile Pro Ser Pro Gln Gly Phe Leu Pro Leu Leu Tyr
            500                 505                 510

Thr Asp Leu Arg Thr Ile Ile Leu Trp Ser Tyr His Leu Leu Ser Asn
        515                 520                 525

Leu Ile Ser Gly Thr Gln Thr Val Ile Ser His Leu Arg Leu Gly Leu
    530                 535                 540

Trp Ile Leu Gly Gln Lys Ile Ile Asp Ala Cys Arg Ile Cys Ala Ala
545                 550                 555                 560

Val Ile His Tyr Trp Leu Gln Glu Leu Gln Lys Ser Ala Thr Ser Leu
                565                 570                 575

Ile Asp Thr Phe Ala Val Ala Val Ala Asn Trp Thr Asp Asp Ile Ile
            580                 585                 590

Leu Gly Ile Gln Arg Leu Gly Arg Gly Ile Leu Asn Ile Pro Arg Arg
        595                 600                 605

Val Arg Gln Gly Phe Glu Arg Ser Leu Leu
    610                 615

<210> SEQ ID NO 55
<211> LENGTH: 466
<212> TYPE: PRT
<213> ORGANISM: Human Immunodeficiency Virus
<220> FEATURE:
<223> OTHER INFORMATION: HIV-2 recombinant peptide (pHIV-210)

<400> SEQUENCE: 55

Met Ser Phe Val Val Ile Ile Pro Ala Arg Tyr Ala Ser Thr Arg Leu
1               5                   10                  15
```

-continued

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
            50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
            115                 120                 125

Pro Ile His Asn Ala Glu Glu Ala Phe Asn Pro Asn Ala Val Lys Val
            130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
            165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
            195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Met Glu Gly Glu Leu Thr Cys Asn Ser Thr
            245                 250                 255

Val Thr Ser Ile Ile Ala Asn Ile Asp Ser Asp Gly Asn Gln Thr Asn
            260                 265                 270

Ile Thr Phe Ser Ala Glu Val Ala Glu Leu Tyr Arg Leu Glu Leu Gly
    275                 280                 285

Asp Tyr Lys Leu Ile Glu Val Thr Pro Ile Gly Phe Ala Pro Thr Lys
    290                 295                 300

Glu Lys Arg Tyr Ser Ser Ala Pro Val Arg Asn Lys Arg Gly Val Phe
305                 310                 315                 320

Val Leu Gly Phe Leu Gly Phe Leu Ala Thr Ala Gly Ser Ala Met Gly
            325                 330                 335

Ala Ala Ser Leu Thr Leu Ser Ala Gln Ser Arg Thr Leu Leu Ala Gly
            340                 345                 350

Ile Val Gln Gln Gln Gln Leu Leu Asp Val Val Lys Arg Gln Gln
    355                 360                 365

Glu Met Leu Arg Leu Thr Val Trp Gly Thr Lys Asn Leu Gln Ala Arg
    370                 375                 380

Val Thr Ala Ile Glu Lys Tyr Leu Lys Asp Gln Ala Gln Leu Asn Ser
385                 390                 395                 400

Trp Gly Cys Ala Phe Arg Gln Val Cys His Thr Thr Val Pro Trp Val
            405                 410                 415

Asn Asp Ser Leu Thr Pro Asp Trp Asn Asn Met Thr Trp Gln Glu Trp
            420                 425                 430

```
Glu Lys Arg Val His Tyr Leu Glu Ala Asn Ile Ser Gln Ser Leu Glu
        435                 440                 445

Gln Ala Gln Ile Gln Gln Glu Lys Asn Met Tyr Glu Leu Gln Lys Leu
        450                 455                 460

Asn Ser
465

<210> SEQ ID NO 56
<211> LENGTH: 491
<212> TYPE: PRT
<213> ORGANISM: Human Immunodeficiency Virus
<220> FEATURE:
<223> OTHER INFORMATION: HIV-1 Group M recombinant peptide (pTB319)

<400> SEQUENCE: 56

Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
            20                  25                  30

Val Leu Glu Arg Ala Arg Glu Ser Gly Ala Glu Arg Ile Ile Val Ala
        35                  40                  45

Thr Asp His Glu Asp Val Ala Arg Ala Val Glu Ala Ala Gly Gly Glu
    50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Pro
225                 230                 235                 240

Ser Thr Ala Leu Met Lys Ile Pro Gly Asp Pro Gly Gly Gly Asp Met
                245                 250                 255

Arg Asp Asn Trp Arg Ser Glu Leu Tyr Lys Tyr Lys Val Val Lys Ile
            260                 265                 270

Glu Pro Leu Gly Val Ala Pro Thr Lys Ala Lys Arg Arg Val Val Gln
        275                 280                 285

Arg Glu Lys Arg Ala Val Gly Ile Gly Ala Leu Phe Leu Gly Phe Leu
    290                 295                 300

Gly Ala Ala Gly Ser Thr Met Gly Ala Ala Ser Met Thr Leu Thr Val
305                 310                 315                 320
```

```
Gln Ala Arg Gln Leu Leu Ser Gly Ile Val Gln Gln Asn Asn Leu
                325                 330                 335

Leu Arg Ala Ile Glu Ala Gln Gln His Leu Leu Gln Leu Thr Val Trp
                340                 345                 350

Gly Ile Lys Gln Leu Gln Ala Arg Ile Leu Ala Val Glu Arg Tyr Leu
                355                 360                 365

Lys Asp Gln Gln Leu Leu Gly Ile Trp Gly Cys Ser Gly Lys Leu Ile
            370                 375                 380

Cys Thr Thr Ala Val Pro Trp Asn Ala Ser Trp Ser Asn Lys Ser Leu
385                 390                 395                 400

Glu Gln Ile Trp Asn Asn Met Thr Trp Met Glu Trp Asp Arg Glu Ile
                405                 410                 415

Asn Asn Tyr Thr Ser Leu Ile His Ser Leu Ile Glu Glu Ser Gln Asn
                420                 425                 430

Gln Gln Glu Lys Asn Glu Gln Glu Leu Leu Glu Leu Asp Lys Trp Val
            435                 440                 445

Asn Arg Val Arg Gln Gly Tyr Ser Pro Leu Ser Phe Gln Thr His Leu
        450                 455                 460

Pro Ile Pro Arg Gly Pro Asp Arg Pro Glu Gly Ile Glu Lys Lys Ala
465                 470                 475                 480

Ala Asn Val Thr Val Thr Val Pro Phe Val Trp
                485                 490

<210> SEQ ID NO 57
<211> LENGTH: 651
<212> TYPE: DNA
<213> ORGANISM: Human Immunodeficiency Virus
<220> FEATURE:
<223> OTHER INFORMATION: Nucleotide sequence of the coding region of
      pGO-8PL

<400> SEQUENCE: 57
atgatcggtg gtgacatgaa agacatctgg cgtaacgaac tgttcaaata caaagttgtt      60
cgtgttaaac cgttctctgt tgctccgacc ccgatcgctc gtccggttat cggtactggc     120
acccaccgtg aaaaacgtgc tgtaggtctg ggtatgctgt tcctgggcgt tctgtctgca     180
gcaggttcca ctatgggtgc tgcagctacc gctctgaccg tacagaccca ctctgttatc     240
aaaggtatcg tacagcagca ggacaacctg ctgcgtgcaa tccaggcaca gcaggaactg     300
ctgcgtctgt ctgtatgggg tatccgtcag ctgcgtgctc gtctgctggc actggaaacc     360
ctgatccaga accagcagct gctgaacctg tggggctgca aggtcgtctc gatctgctac     420
acctccgtta atggaacgaa acctggcgta acaccacca acatcaacca gatctggggt     480
aacctgacct ggcaggaatg ggaccagcag atcgacaacg tttcttccac catctacgaa     540
gaaatccaga agctcaggt tcagcaggaa cagaacgaaa aaaaactgct ggaactggac     600
gaatgggctt ctctgtggaa ctggctggac atcaccaaat ggctgtaata g              651

<210> SEQ ID NO 58
<211> LENGTH: 215
<212> TYPE: PRT
<213> ORGANISM: Human Immunodeficiency Virus
<220> FEATURE:
<223> OTHER INFORMATION: Encodes recombinant protein pGO-8PL

<400> SEQUENCE: 58

Met Ile Gly Gly Asp Met Lys Asp Ile Trp Arg Asn Glu Leu Phe Lys
  1               5                  10                  15
```

```
Tyr Lys Val Val Arg Val Lys Pro Phe Ser Val Ala Pro Thr Pro Ile
         20                  25                  30

Ala Arg Pro Val Ile Gly Thr Gly Thr His Arg Glu Lys Arg Ala Val
         35                  40                  45

Gly Leu Gly Met Leu Phe Leu Gly Val Leu Ser Ala Ala Gly Ser Thr
 50                  55                  60

Met Gly Ala Ala Ala Thr Ala Leu Thr Val Gln Thr His Ser Val Ile
 65                  70                  75                  80

Lys Gly Ile Val Gln Gln Gln Asp Asn Leu Leu Arg Ala Ile Gln Ala
             85                  90                  95

Gln Gln Glu Leu Leu Arg Leu Ser Val Trp Gly Ile Arg Gln Leu Arg
         100                 105                 110

Ala Arg Leu Leu Ala Leu Glu Thr Leu Ile Gln Asn Gln Gln Leu Leu
         115                 120                 125

Asn Leu Trp Gly Cys Lys Gly Arg Leu Ile Cys Tyr Thr Ser Val Lys
130                 135                 140

Trp Asn Glu Thr Trp Arg Asn Thr Thr Asn Ile Asn Gln Ile Trp Gly
145                 150                 155                 160

Asn Leu Thr Trp Gln Glu Trp Asp Gln Gln Ile Asp Asn Val Ser Ser
                165                 170                 175

Thr Ile Tyr Glu Glu Ile Gln Lys Ala Gln Val Gln Gln Glu Gln Asn
            180                 185                 190

Glu Lys Lys Leu Leu Glu Leu Asp Glu Trp Ala Ser Leu Trp Asn Trp
            195                 200                 205

Leu Asp Ile Thr Lys Trp Leu
            210                 215

<210> SEQ ID NO 59
<211> LENGTH: 1386
<212> TYPE: DNA
<213> ORGANISM: Human Immunodeficiency Virus
<220> FEATURE:
<223> OTHER INFORMATION: Nucleotide sequence of the coding region of
      pGO-8CKS

<400> SEQUENCE: 59
atgagttttg tggtcattat tcccgcgcgc tacgcgtcga cgcgtctgcc cggtaaacca      60
ttggttgata ttaacggcaa acccatgatt gttcatgttc ttgaacgcgc gcgtgaatca     120
ggtgccgagc gcatcatcgt ggcaaccgat catgaggatg ttgcccgcgc cgttgaagcc     180
gctggcggtg aagtatgtat gacgcgcgcc gatcatcagt caggaacaga acgtctggcg     240
gaagttgtcg aaaaatgcgc attcagcgac gacacggtga tcgttaatgt gcagggtgat     300
gaaccgatga tccctgcgac aatcattcgt caggttgctg ataacctcgc tcagcgtcag     360
gtgggtatga cgactctggc ggtgccaatc cacaatgcgg aagaagcgtt taacccgaat     420
gcggtgaaag tggttctcga cgctgaaggg tatgcactgt acttctctcg cgccaccatt     480
ccttgggatc gtgatcgttt tgcagaaggc cttgaaaccg ttggcgataa cttcctgcgt     540
catcttggta tttatggcta ccgtgcaggc tttatccgtc gttacgtcaa ctggcagcca     600
agtccgttag aacacatcga atgttagag cagcttcgtg ttctgtggta cggcgaaaaa     660
atccatgttg ctgttgctca ggaagttcct ggcacaggtg tggatacccc tgaagatctc     720
gacccgtcga cgaattctat cggtggtgac atgaaagaca tctggcgtaa cgaactgttc     780
aaatacaaag ttgttcgtgt taaaccgttc tctgttgctc cgaccccgat cgctcgtccg     840
gttatcggta ctggcaccca ccgtgaaaaa cgtgctgtag gtctgggtat gctgttcctg     900
```

-continued

```
ggcgttctgt ctgcagcagg ttccactatg ggtgctgcag ctaccgctct gaccgtacag        960
acccactctg ttatcaaagg tatcgtacag cagcaggaca acctgctgcg tgcaatccag       1020
gcacagcagg aactgctgcg tctgtctgta tggggtatcc gtcagctgcg tgctcgtctg       1080
ctggcactgg aaaccctgat ccagaaccag cagctgctga acctgtgggg ctgcaaaggt       1140
cgtctgatct gctacacctc cgttaaatgg aacgaaacct ggcgtaacac caccaacatc       1200
aaccagatct ggggtaacct gacctggcag gaatgggacc agcagatcga caacgtttct       1260
tccaccatct acgaagaaat ccagaaagct caggttcagc aggaacagaa cgaaaaaaaa       1320
ctgctggaac tggacgaatg ggcttctctg tggaactggc tggacatcac caaatggctg       1380
taatag                                                                  1386
```

<210> SEQ ID NO 60
<211> LENGTH: 460
<212> TYPE: PRT
<213> ORGANISM: Human Immunodeficiency Virus
<220> FEATURE:
<223> OTHER INFORMATION: Encodes recombinant protein pGO-8CKS

<400> SEQUENCE: 60

```
Met Ser Phe Val Val Ile Ile Pro Ala Arg Tyr Ala Ser Thr Arg Leu
  1               5                  10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
     50                  55                  60

Val Cys Met Thr Arg Ala Asp His Gln Ser Gly Thr Glu Arg Leu Ala
 65                  70                  75                  80

Glu Val Glu Lys Cys Ala Phe Ser Asp Asp Thr Val Ile Val Asn Val
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Thr Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Leu
225                 230                 235                 240

Asp Pro Ser Thr Asn Ser Ile Gly Gly Asp Met Lys Asp Ile Trp Arg
                245                 250                 255

Asn Glu Leu Phe Lys Tyr Lys Val Val Arg Val Lys Pro Phe Ser Val
            260                 265                 270
```

```
Ala Pro Thr Pro Ile Ala Arg Pro Val Ile Gly Thr Gly Thr His Arg
        275                 280                 285

Glu Lys Arg Ala Val Gly Leu Gly Met Leu Phe Leu Gly Val Leu Ser
        290                 295                 300

Ala Ala Gly Ser Thr Met Gly Ala Ala Ala Thr Ala Leu Thr Val Gln
305                 310                 315                 320

Thr His Ser Val Ile Lys Gly Ile Val Gln Gln Gln Asp Asn Leu Leu
                325                 330                 335

Arg Ala Ile Gln Ala Gln Gln Glu Leu Leu Arg Leu Ser Val Trp Gly
        340                 345                 350

Ile Arg Gln Leu Arg Ala Arg Leu Leu Ala Leu Glu Thr Leu Ile Gln
        355                 360                 365

Asn Gln Gln Leu Leu Asn Leu Trp Gly Cys Lys Gly Arg Leu Ile Cys
        370                 375                 380

Tyr Thr Ser Val Lys Trp Asn Glu Thr Trp Arg Asn Thr Thr Asn Ile
385                 390                 395                 400

Asn Gln Ile Trp Gly Asn Leu Thr Trp Gln Glu Trp Asp Gln Gln Ile
                405                 410                 415

Asp Asn Val Ser Ser Thr Ile Tyr Glu Glu Ile Gln Lys Ala Gln Val
                420                 425                 430

Gln Gln Glu Gln Asn Glu Lys Lys Leu Leu Glu Leu Asp Glu Trp Ala
        435                 440                 445

Ser Leu Trp Asn Trp Leu Asp Ile Thr Lys Trp Leu
        450                 455                 460

<210> SEQ ID NO 61
<211> LENGTH: 873
<212> TYPE: PRT
<213> ORGANISM: Human Immunodeficiency Virus
<220> FEATURE:
<223> OTHER INFORMATION: HIV-1 Group O isolate HAM112

<400> SEQUENCE: 61

Met Ile Val Thr Met Arg Ala Met Gly Lys Arg Asn Arg Lys Leu Gly
1               5                   10                  15

Ile Leu Tyr Ile Val Met Ala Leu Ile Ile Pro Cys Leu Ser Ser Ser
                20                  25                  30

Gln Leu Tyr Ala Thr Val Tyr Ala Gly Val Pro Val Trp Glu Asp Ala
        35                  40                  45

Ala Pro Val Leu Phe Cys Ala Ser Asp Ala Asn Leu Thr Ser Thr Glu
    50                  55                  60

Lys His Asn Val Trp Ala Ser Gln Ala Cys Val Pro Thr Asp Pro Thr
65                  70                  75                  80

Pro His Glu Tyr Leu Leu Thr Asn Val Thr Asp Asn Phe Asn Ile Trp
                85                  90                  95

Glu Asn Tyr Met Val Glu Gln Met Gln Glu Asp Ile Ile Ser Leu Trp
                100                 105                 110

Asp Gln Ser Leu Lys Pro Cys Ile Gln Met Thr Phe Met Cys Ile Gln
        115                 120                 125

Met Asn Cys Thr Asp Ile Lys Asn Asn Thr Ser Gly Thr Glu Asn
        130                 135                 140

Arg Thr Ser Ser Ser Glu Asn Pro Met Lys Thr Cys Glu Phe Asn Ile
145                 150                 155                 160

Thr Thr Val Leu Lys Asp Lys Lys Glu Lys Lys Gln Ala Leu Phe Tyr
                165                 170                 175
```

```
Val Ser Asp Leu Thr Lys Leu Ala Asp Asn Asn Thr Thr Asn Thr Met
            180                 185                 190

Tyr Thr Leu Ile Asn Cys Asn Ser Thr Thr Ile Lys Gln Ala Cys Pro
            195                 200                 205

Lys Val Ser Phe Glu Pro Ile Pro Ile Tyr Tyr Cys Ala Pro Ala Gly
210                 215                 220

Tyr Ala Ile Phe Lys Cys Asn Ser Ala Glu Phe Asn Gly Thr Gly Lys
225                 230                 235                 240

Cys Ser Asn Ile Ser Val Val Thr Cys Thr His Gly Ile Lys Pro Thr
                245                 250                 255

Val Ser Thr Gln Leu Ile Leu Asn Gly Thr Leu Ser Lys Glu Lys Ile
            260                 265                 270

Arg Ile Met Gly Lys Asn Ile Ser Asp Ser Gly Lys Asn Ile Ile Val
            275                 280                 285

Thr Leu Ser Ser Asp Ile Glu Ile Thr Cys Val Arg Pro Gly Asn Asn
            290                 295                 300

Gln Thr Val Gln Glu Met Lys Ile Gly Pro Met Ala Trp Tyr Ser Met
305                 310                 315                 320

Ala Leu Gly Thr Gly Ser Asn Arg Ser Arg Val Ala Tyr Cys Gln Tyr
                325                 330                 335

Asn Thr Thr Glu Trp Glu Lys Ala Leu Lys Asn Thr Ala Glu Arg Tyr
            340                 345                 350

Leu Glu Leu Ile Asn Asn Thr Glu Gly Asn Thr Thr Met Ile Phe Asn
            355                 360                 365

Arg Ser Gln Asp Gly Ser Asp Val Glu Val Thr His Leu His Phe Asn
            370                 375                 380

Cys His Gly Glu Phe Phe Tyr Cys Asn Thr Ser Glu Met Phe Asn Tyr
385                 390                 395                 400

Thr Phe Leu Cys Asn Gly Thr Asn Cys Asn Asn Thr Gln Ser Ile Asn
                405                 410                 415

Ser Ala Asn Gly Met Ile Pro Cys Lys Leu Lys Gln Val Val Arg Ser
            420                 425                 430

Trp Met Arg Gly Gly Ser Gly Leu Tyr Ala Pro Pro Ile Pro Gly Asn
            435                 440                 445

Leu Thr Cys Ile Ser His Ile Thr Gly Met Ile Leu Gln Met Asp Ala
            450                 455                 460

Pro Trp Asn Lys Thr Glu Asn Thr Phe Arg Pro Ile Gly Gly Asp Met
465                 470                 475                 480

Lys Asp Ile Trp Arg Asn Glu Leu Phe Lys Tyr Lys Val Val Arg Val
                485                 490                 495

Lys Pro Phe Ser Val Ala Pro Thr Pro Ile Ala Arg Pro Val Ile Gly
            500                 505                 510

Thr Gly Thr His Arg Glu Lys Arg Ala Val Gly Leu Gly Met Leu Phe
            515                 520                 525

Leu Gly Val Leu Ser Ala Ala Gly Ser Thr Met Gly Ala Ala Ala Thr
            530                 535                 540

Ala Leu Thr Val Gln Thr His Ser Val Ile Lys Gly Ile Val Gln Gln
545                 550                 555                 560

Gln Asp Asn Leu Leu Arg Ala Ile Gln Ala Gln Gln Glu Leu Leu Arg
                565                 570                 575

Leu Ser Val Trp Gly Ile Arg Gln Leu Arg Ala Arg Leu Leu Ala Leu
            580                 585                 590
```

```
Glu Thr Leu Ile Gln Asn Gln Gln Leu Leu Asn Leu Trp Gly Cys Lys
            595                 600                 605

Gly Arg Leu Ile Cys Tyr Thr Ser Val Lys Trp Asn Glu Thr Trp Arg
            610                 615                 620

Asn Thr Thr Asn Ile Asn Gln Ile Trp Gly Asn Leu Thr Trp Gln Glu
625                 630                 635                 640

Trp Asp Gln Gln Ile Asp Asn Val Ser Ser Thr Ile Tyr Glu Glu Ile
                645                 650                 655

Gln Lys Ala Gln Val Gln Gln Glu Gln Asn Glu Lys Lys Leu Leu Glu
            660                 665                 670

Leu Asp Glu Trp Ala Ser Leu Trp Asn Trp Leu Asp Ile Thr Lys Trp
            675                 680                 685

Leu Trp Tyr Ile Lys Ile Ala Ile Ile Ile Val Gly Ala Leu Ile Gly
            690                 695                 700

Val Arg Ile Val Met Ile Val Leu Asn Leu Val Arg Asn Ile Arg Gln
705                 710                 715                 720

Gly Tyr Gln Pro Leu Ser Leu Gln Ile Pro Thr Arg Gln Gln Ser Glu
                725                 730                 735

Ala Glu Thr Pro Gly Arg Thr Gly Glu Gly Gly Gly Asp Glu Gly Arg
            740                 745                 750

Pro Arg Leu Ile Pro Ser Pro Gln Gly Phe Leu Pro Leu Leu Tyr Thr
            755                 760                 765

Asp Leu Arg Thr Ile Ile Leu Trp Ser Tyr His Leu Leu Ser Asn Leu
            770                 775                 780

Ile Ser Gly Thr Gln Thr Val Ile Ser His Leu Arg Leu Gly Leu Trp
785                 790                 795                 800

Ile Leu Gly Gln Lys Ile Ile Asp Ala Cys Arg Ile Cys Ala Ala Val
                805                 810                 815

Ile His Tyr Trp Leu Gln Glu Leu Gln Lys Ser Ala Thr Ser Leu Ile
            820                 825                 830

Asp Thr Phe Ala Val Ala Val Ala Asn Trp Thr Asp Asp Ile Ile Leu
            835                 840                 845

Gly Ile Gln Arg Leu Gly Arg Gly Ile Leu Asn Ile Pro Arg Arg Val
            850                 855                 860

Arg Gln Gly Phe Glu Arg Ser Leu Leu
865                 870

<210> SEQ ID NO 62
<211> LENGTH: 20
<212> TYPE: DNA
<213> ORGANISM: Human Immunodeficiency Virus
<220> FEATURE:
<223> OTHER INFORMATION: HIV-1 Group O (env10R) PCR reverse primer

<400> SEQUENCE: 62
yctytagaga gtgtcccatt                                               20

<210> SEQ ID NO 63
<211> LENGTH: 19
<212> TYPE: DNA
<213> ORGANISM: Human Immunodeficiency Virus
<220> FEATURE:
<223> OTHER INFORMATION: HIV-1 Group O (env15R) PCR reverse primer

<400> SEQUENCE: 63
gtgctwcctg ctgcactta                                                19
```

```
<210> SEQ ID NO 64
<211> LENGTH: 20
<212> TYPE: DNA
<213> ORGANISM: Human Immunodeficiency Virus
<220> FEATURE:
<223> OTHER INFORMATION: HIV-1 Group O (env22R) PCR reverse primer

<400> SEQUENCE: 64
aagttgctca agaggtggta                                               20

<210> SEQ ID NO 65
<211> LENGTH: 19
<212> TYPE: DNA
<213> ORGANISM: Human Immunodeficiency Virus
<220> FEATURE:
<223> OTHER INFORMATION: HIV-1 Group O (env26R) PCR reverse primer

<400> SEQUENCE: 65
ccttagaggc acttgaggt                                                19

<210> SEQ ID NO 66
<211> LENGTH: 19
<212> TYPE: DNA
<213> ORGANISM: Human Immunodeficiency Virus
<220> FEATURE:
<223> OTHER INFORMATION: HIV-1 Group O (env1F) PCR forward primer

<400> SEQUENCE: 66
ccaragcagt aagtaacgc                                                19

<210> SEQ ID NO 67
<211> LENGTH: 23
<212> TYPE: DNA
<213> ORGANISM: Human Immunodeficiency Virus
<220> FEATURE:
<223> OTHER INFORMATION: HIV-1 Group O (env7F) PCR forward primer

<400> SEQUENCE: 67
rttaaytaat tgtaactcca caa                                           23

<210> SEQ ID NO 68
<211> LENGTH: 20
<212> TYPE: DNA
<213> ORGANISM: Human Immunodeficiency Virus
<220> FEATURE:
<223> OTHER INFORMATION: HIV-1 Group O (env12F) PCR forward primer

<400> SEQUENCE: 68
gamtytatgc acctcccatc                                               20

<210> SEQ ID NO 69
<211> LENGTH: 21
<212> TYPE: DNA
<213> ORGANISM: Human Immunodeficiency Virus
<220> FEATURE:
<223> OTHER INFORMATION: HIV-1 Group O (env19F) PCR forward primer

<400> SEQUENCE: 69
gacataacta aatggttgtg g                                             21

<210> SEQ ID NO 70
<211> LENGTH: 23
<212> TYPE: DNA
<213> ORGANISM: Human Immunodeficiency Virus
<220> FEATURE:
<223> OTHER INFORMATION: HIV-1 Group O (env2F) PCR forward primer
```

```
<400> SEQUENCE: 70
atacttgara grttaagrag aat                                             23

<210> SEQ ID NO 71
<211> LENGTH: 20
<212> TYPE: DNA
<213> ORGANISM: Human Immunodeficiency Virus
<220> FEATURE:
<223> OTHER INFORMATION: HIV-1 Group O (env9R) PCR reverse primer

<400> SEQUENCE: 71
atgccatgtg tacaagtaac                                                 20

<210> SEQ ID NO 72
<211> LENGTH: 20
<212> TYPE: DNA
<213> ORGANISM: Human Immunodeficiency Virus
<220> FEATURE:
<223> OTHER INFORMATION: HIV-1 Group O (env8F) PCR forward primer

<400> SEQUENCE: 72
atacactatt gtgctccarc                                                 20

<210> SEQ ID NO 73
<211> LENGTH: 22
<212> TYPE: DNA
<213> ORGANISM: Human Immunodeficiency Virus
<220> FEATURE:
<223> OTHER INFORMATION: HIV-1 Group O (env14R) PCR reverse primer

<400> SEQUENCE: 73
agttctccat atatctttca tr                                              22

<210> SEQ ID NO 74
<211> LENGTH: 22
<212> TYPE: DNA
<213> ORGANISM: Human Immunodeficiency Virus
<220> FEATURE:
<223> OTHER INFORMATION: HIV-1 Group O (env13F) PCR forward primer

<400> SEQUENCE: 74
aacataactg gaatgatyct ac                                              22

<210> SEQ ID NO 75
<211> LENGTH: 18
<212> TYPE: DNA
<213> ORGANISM: Human Immunodeficiency Virus
<220> FEATURE:
<223> OTHER INFORMATION: HIV-1 Group O (env21R) PCR reverse primer

<400> SEQUENCE: 75
ctgagrtccg tgtacaac                                                   18

<210> SEQ ID NO 76
<211> LENGTH: 20
<212> TYPE: DNA
<213> ORGANISM: Human Immunodeficiency Virus
<220> FEATURE:
<223> OTHER INFORMATION: HIV-1 Group O (env20F) PCR forward primer

<400> SEQUENCE: 76
attaggcagg gatatcaacc                                                 20

<210> SEQ ID NO 77
<211> LENGTH: 18
```

```
<212> TYPE: DNA
<213> ORGANISM: Human Immunodeficiency Virus
<220> FEATURE:
<223> OTHER INFORMATION: HIV-1 Group O (env25R) PCR reverse primer

<400> SEQUENCE: 77
cctactccag gtgcrcat                                                 18

<210> SEQ ID NO 78
<211> LENGTH: 19
<212> TYPE: DNA
<213> ORGANISM: Human Immunodeficiency Virus
<220> FEATURE:
<223> OTHER INFORMATION: HIV-1 Group O (env4F) PCR forward primer

<400> SEQUENCE: 78
cawcacaagc ctgygttcc                                                19

<210> SEQ ID NO 79
<211> LENGTH: 20
<212> TYPE: DNA
<213> ORGANISM: Human Immunodeficiency Virus
<220> FEATURE:
<223> OTHER INFORMATION: HIV-1 Group O (env5R) PCR reverse primer

<400> SEQUENCE: 79
atgtcttcvt gcatttgktc                                               20

<210> SEQ ID NO 80
<211> LENGTH: 20
<212> TYPE: DNA
<213> ORGANISM: Human Immunodeficiency Virus
<220> FEATURE:
<223> OTHER INFORMATION: HIV-1 Group O (env10F) PCR forward primer

<400> SEQUENCE: 80
aatgggacac tctctaragr                                               20

<210> SEQ ID NO 81
<211> LENGTH: 22
<212> TYPE: DNA
<213> ORGANISM: Human Immunodeficiency Virus
<220> FEATURE:
<223> OTHER INFORMATION: HIV-1 Group O (env11F) PCR forward primer

<400> SEQUENCE: 81
ttaactgtca tggagaattc tt                                            22

<210> SEQ ID NO 82
<211> LENGTH: 22
<212> TYPE: DNA
<213> ORGANISM: Human Immunodeficiency Virus
<220> FEATURE:
<223> OTHER INFORMATION: HIV-1 Group O (env11R) PCR reverse primer

<400> SEQUENCE: 82
aagaattctc catgacagtt aa                                            22

<210> SEQ ID NO 83
<211> LENGTH: 19
<212> TYPE: DNA
<213> ORGANISM: Human Immunodeficiency Virus
<220> FEATURE:
<223> OTHER INFORMATION: HIV-1 Group O (env15F) PCR forward primer

<400> SEQUENCE: 83
```

```
taagtgcagc aggwagcac                                                 19
```

<210> SEQ ID NO 84
<211> LENGTH: 21
<212> TYPE: DNA
<213> ORGANISM: Human Immunodeficiency Virus
<220> FEATURE:
<223> OTHER INFORMATION: HIV-1 Group O (env19R) PCR reverse primer

<400> SEQUENCE: 84

```
ccacaaccat ttagttatgt c                                              21
```

<210> SEQ ID NO 85
<211> LENGTH: 20
<212> TYPE: DNA
<213> ORGANISM: Human Immunodeficiency Virus
<220> FEATURE:
<223> OTHER INFORMATION: HIV-1 Group O (env22F) PCR forward primer

<400> SEQUENCE: 85

```
taccacctct tgagcaactt                                                20
```

<210> SEQ ID NO 86
<211> LENGTH: 19
<212> TYPE: DNA
<213> ORGANISM: Human Immunodeficiency Virus
<220> FEATURE:
<223> OTHER INFORMATION: HIV-1 Group O (env24R) PCR reverse primer

<400> SEQUENCE: 86

```
cytgtctaat yctycttgg                                                 19
```

<210> SEQ ID NO 87
<211> LENGTH: 19
<212> TYPE: DNA
<213> ORGANISM: Human Immunodeficiency Virus
<220> FEATURE:
<223> OTHER INFORMATION: HIV-1 Group O PCR primer AG1

<400> SEQUENCE: 87

```
tggcctggta cagcatggg                                                 19
```

<210> SEQ ID NO 88
<211> LENGTH: 32
<212> TYPE: DNA
<213> ORGANISM: Human Immunodeficiency Virus
<220> FEATURE:
<223> OTHER INFORMATION: PCR Primer 3634

<400> SEQUENCE: 88

```
gtacgaattc catggaaggg gagttgacct gc                                  32
```

<210> SEQ ID NO 89
<211> LENGTH: 34
<212> TYPE: DNA
<213> ORGANISM: Human Immunodeficiency Virus
<220> FEATURE:
<223> OTHER INFORMATION: PCR Primer 3636

<400> SEQUENCE: 89

```
tattggatcc ttatcagcta tttagttttt gtag                                34
```

<210> SEQ ID NO 90
<211> LENGTH: 2214
<212> TYPE: DNA
<213> ORGANISM: Human Immunodeficiency Virus
<220> FEATURE:
<223> OTHER INFORMATION: Nucleotide sequence of the coding region of pGO-12CKS

<400> SEQUENCE: 90

```
atgagttttg tggtcattat tcccgcgcgc tacgcgtcga cgcgtctgcc cggtaaacca      60
ttggttgata ttaacggcaa acccatgatt gttcatgttc ttgaacgcgc gcgtgaatca     120
ggtgccgagc gcatcatcgt ggcaaccgat catgaggatg ttgcccgcgc cgttgaagcc     180
gctggcggtg aagtatgtat gacgcgcgcc gatcatcagt caggaacaga acgtctggcg     240
gaagttgtcg aaaaatgcgc attcagcgac gacacggtga tcgttaatgt gcagggtgat     300
gaaccgatga tccctgcgac aatcattcgt caggttgctg ataacctcgc tcagcgtcag     360
gtgggtatgg cgactctggc ggtgccaatc cacaatgcgg aagaagcgtt taacccgaat     420
gcggtgaaag tggttctcga cgctgaaggg tatgcactgt acttctctcg cgccaccatt     480
ccttgggatc gtgatcgttt tgcagaaggc cttgaaaccg ttggcgataa cttcctgcgt     540
catcttggta tttatggcta ccgtgcaggc tttatccgtc gttacgtcaa ctggcagcca     600
agtccgttag aacacatcga atgttagag cagcttcgtg ttctgtggta cggcgaaaaa     660
atccatgttg ctgttgctca ggaagttcct ggcacaggtg tggatacccc tgaagatccg     720
tcgacagccc ttatgaagat ccccggcgac ccgggtggtg gtgacatgcg tgacaactgg     780
cgttctgaac tgtacaaata caaagttgtt aaaatcgaac cgctgggtgt gctccgact      840
aaagctaaac gtcgtgttgt tcagcgtgaa aaacgcgccg ttggtatcgg tgcactgttc     900
ctgggtttcc tgggtgctgc tggttctacc atgggtgctg cttctatgac cctgactgtt     960
caggcccgtc agcttctgtc tggtatcgtt cagcagcaga caatctgct gcgtgctatc    1020
gaagctcagc agcatctgct gcaactgacc gtttggggta tcaaacagct tcaggctcgt    1080
atcctggctg ttgaacgtta cctgaaagac cagcagctgc tgggtatctg gggttgctct    1140
ggtaaactga tctgcactac tgctgttccg tggaacgctt cttggtctaa caaatctctg    1200
gaacagatct ggaacaacat gacttggatg gaatgggacc gtgaaatcaa caactacaca    1260
agcttgatcc actctctgat cgaagaaagc cagaaccagc aggaaaaaaa cgaacaggaa    1320
cttctagaac tggacaaatg ggttaaccgt gttcgtcagg ttactctcc gctgtctttc    1380
cagacccatc tgccgatccc gcgtggtccg gaccgtccgg aaggtatcga agaagaaggc    1440
ggcgaacgtg accgtgaccg ttccattcgt ctggtaatcg tggtgacat gaaagacatc    1500
tggcgtaacg aactgttcaa atacaaagtt gttcgtgtta aaccgttctc tgttgctccg    1560
accccgatcg ctcgtccggt tatcggtact ggcacccacc gtgaaaaacg tgctgtaggt    1620
ctgggtatgc tgttcctggg cgttctgtct gcagcaggtt ccactatggg tgctgcagct    1680
accgctctga ccgtacagac ccactctgtt atcaaaggta tcgtacagca gcaggacaac    1740
ctgctgcgtc aatccaggc acagcaggaa ctgctgcgtc tgtctgtatg gggtatccgt    1800
cagctgcgtg ctcgtctgct ggcactggaa accctgatcc agaaccagca gctgctgaac    1860
ctgtggggct gcaaaggtcg tctgatctgc tacacctccg ttaaatggaa cgaaacctgg    1920
cgtaacacca ccaacatcaa ccagatctgg ggtaacctga cctggcagga atgggaccag    1980
cagatcgaca acgtttcttc caccatctac gaagaaatcc agaaagctca ggttcagcag    2040
gaacagaacg aaaaaaaact gctggaactg gacgaatggg cttctctgtg gaactggctg    2100
gacatcacca atggctgcg taacatccgt cagggctacc agccgctgtc cctgcagatc    2160
ccgacccgtc agcagtctga agctgaaact ccgggtcgta ccggtgaata atag          2214
```

<210> SEQ ID NO 91
<211> LENGTH: 736
<212> TYPE: PRT
<213> ORGANISM: Human Immunodeficiency Virus
<220> FEATURE:
<223> OTHER INFORMATION: Encodes recombinant protein pGO-12CKS

<400> SEQUENCE: 91

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
                20                  25                  30

Val Leu Glu Arg Ala Arg Glu Ser Gly Ala Glu Arg Ile Ile Val Ala
            35                  40                  45

Thr Asp His Glu Asp Val Ala Arg Ala Val Glu Ala Ala Gly Gly Glu
        50                  55                  60

Val Cys Met Thr Arg Ala Asp His Gln Ser Gly Thr Glu Arg Leu Ala
65                  70                  75                  80

Glu Val Val Glu Lys Cys Ala Phe Ser Asp Asp Thr Val Ile Val Asn
                85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Pro
225                 230                 235                 240

Ser Thr Ala Leu Met Lys Ile Pro Gly Asp Pro Gly Gly Gly Asp Met
                245                 250                 255

Arg Asp Asn Trp Arg Ser Glu Leu Tyr Lys Tyr Lys Val Val Lys Ile
            260                 265                 270

Glu Pro Leu Gly Val Ala Pro Thr Lys Ala Lys Arg Arg Val Val Gln
        275                 280                 285

Arg Glu Lys Arg Ala Val Gly Ile Gly Ala Leu Phe Leu Gly Phe Leu
    290                 295                 300

Gly Ala Ala Gly Ser Thr Met Gly Ala Ala Ser Met Thr Leu Thr Val
305                 310                 315                 320

Gln Ala Arg Gln Leu Leu Ser Gly Ile Val Gln Gln Gln Asn Asn Leu
                325                 330                 335

Leu Arg Ala Ile Glu Ala Gln Gln His Leu Leu Gln Leu Thr Val Trp
            340                 345                 350

Gly Ile Lys Gln Leu Gln Ala Arg Ile Leu Ala Val Glu Arg Tyr Leu
        355                 360                 365
```

```
Lys Asp Gln Gln Leu Leu Gly Ile Trp Gly Cys Ser Gly Lys Leu Ile
    370                 375                 380
Cys Thr Thr Ala Val Pro Trp Asn Ala Ser Trp Ser Asn Lys Ser Leu
385                 390                 395                 400
Glu Gln Ile Trp Asn Asn Met Thr Trp Met Glu Trp Asp Arg Glu Ile
                405                 410                 415
Asn Asn Tyr Thr Ser Leu Ile His Ser Leu Ile Glu Glu Ser Gln Asn
            420                 425                 430
Gln Gln Glu Lys Asn Glu Gln Glu Leu Leu Glu Leu Asp Lys Trp Val
        435                 440                 445
Asn Arg Val Arg Gln Gly Tyr Ser Pro Leu Ser Phe Gln Thr His Leu
    450                 455                 460
Pro Ile Pro Arg Gly Pro Asp Arg Pro Glu Gly Ile Glu Glu Glu Gly
465                 470                 475                 480
Gly Glu Arg Asp Arg Asp Arg Ser Ile Arg Leu Val Ile Gly Gly Asp
                485                 490                 495
Met Lys Asp Ile Trp Arg Asn Glu Leu Phe Lys Tyr Lys Val Val Arg
            500                 505                 510
Val Lys Pro Phe Ser Val Ala Pro Thr Pro Ile Ala Arg Pro Val Ile
        515                 520                 525
Gly Thr Gly Thr His Arg Glu Lys Arg Ala Val Gly Leu Gly Met Leu
    530                 535                 540
Phe Leu Gly Val Leu Ser Ala Ala Gly Ser Thr Met Gly Ala Ala Ala
545                 550                 555                 560
Thr Ala Leu Thr Val Gln Thr His Ser Val Ile Lys Gly Ile Val Gln
                565                 570                 575
Gln Gln Asp Asn Leu Leu Arg Ala Ile Gln Ala Gln Gln Glu Leu Leu
            580                 585                 590
Arg Leu Ser Val Trp Gly Ile Arg Gln Leu Arg Ala Arg Leu Leu Ala
        595                 600                 605
Leu Glu Thr Leu Ile Gln Asn Gln Gln Leu Leu Asn Leu Trp Gly Cys
    610                 615                 620
Lys Gly Arg Leu Ile Cys Tyr Thr Ser Val Lys Trp Asn Glu Thr Trp
625                 630                 635                 640
Arg Asn Thr Thr Asn Ile Asn Gln Ile Trp Gly Asn Leu Thr Trp Gln
                645                 650                 655
Glu Trp Asp Gln Gln Ile Asp Asn Val Ser Ser Thr Ile Tyr Glu Glu
            660                 665                 670
Ile Gln Lys Ala Gln Val Gln Gln Glu Gln Asn Glu Lys Lys Leu Leu
        675                 680                 685
Glu Leu Asp Glu Trp Ala Ser Leu Trp Asn Trp Leu Asp Ile Thr Lys
    690                 695                 700
Trp Leu Arg Asn Ile Arg Gln Gly Tyr Gln Pro Leu Ser Leu Gln Ile
705                 710                 715                 720
Pro Thr Arg Gln Gln Ser Glu Ala Glu Thr Pro Gly Arg Thr Gly Glu
                725                 730                 735

<210> SEQ ID NO 92
<211> LENGTH: 2124
<212> TYPE: DNA
<213> ORGANISM: Human Immunodeficiency Virus
<220> FEATURE:
<223> OTHER INFORMATION: Nucleotide sequence of the coding regionof
      pGO-13CKS
```

```
<400> SEQUENCE: 92
atgagttttg tggtcattat tcccgcgcgc tacgcgtcga cgcgtctgcc cggtaaacca      60
ttggttgata ttaacggcaa acccatgatt gttcatgttc ttgaacgcgc gcgtgaatca     120
ggtgccgagc gcatcatcgt ggcaaccgat catgaggatg ttgcccgcgc cgttgaagcc     180
gctggcggtg aagtatgtat gacgcgcgcc gatcatcagt caggaacaga acgtctggcg     240
gaagttgtcg aaaaatgcgc attcagcgac gacacgtga tcgttaatgt gcagggtgat     300
gaaccgatga tccctgcgac aatcattcgt caggttgctg ataacctcgc tcagcgtcag     360
gtgggtatgg cgactctggc ggtgccaatc cacaatgcgg aagaagcgtt taacccgaat     420
gcggtgaaag tggttctcga cgctgaaggg tatgcactgt acttctctcg cgccaccatt     480
ccttgggatc gtgatcgttt tgcagaaggc cttgaaaccg ttggcgataa cttcctgcgt     540
catcttggta tttatggcta ccgtgcaggc tttatccgtc gttacgtcaa ctggcagcca     600
agtccgttag aacacatcga aatgttagag cagcttcgtg ttctgtggta cggcgaaaaa     660
atccatgttg ctgttgctca ggaagttcct ggcacaggtg tggataccccc tgaagatccg     720 tcgacagccc ttatgaagat ccccggcgac ccgggtggtg gtgacatgcg tgacaactgg     780
cgttctgaac tgtacaaata caagttgtt aaaatcgaac cgctgggtgt gctccgact      840 aaagctaaac gtcgtgttgt tcagcgtgaa aaacgcgccg ttggtatcgg tgcactgttc     900
ctgggtttcc tgggtgctgc tggttctacc atgggtgctg cttctatgac cctgactgtt     960
caggcccgtc agcttctgtc tggtatcgtt cagcagcaga acaatctgct gcgtgctatc    1020
gaagctcagc agcatctgct gcaactgacc gtttgggggta tcaaacagct tcaggctcgt    1080
atcctggctg ttgaacgtta cctgaaagac cagcagctgc tgggtatctg gggttgctct    1140
ggtaaactga tctgcactac tgctgttccg tggaacgctt cttggtctaa caaatctctg    1200
gaacagatct ggaacaacat gacttggatg aatgggacc gtgaaatcaa caactacaca    1260
agcttgatcc actctctgat cgaagaaagc cagaaccagc aggaaaaaaa cgaacaggaa    1320
cttctagaac tggacaaatg ggttaaccgt ttcgtcagg ttactctccc gctgtctttc    1380
cagacccatc tgccgatccc gcgtggtccg gaccgtccgg aaggtatcga agaagaaggc    1440
ggcgaacgtg accgtgaccg ttccattcgt ctggtaatcg gtggtgacat gaaagacatc    1500
tggcgtaacg aactgttcaa atacaaagtt gttcgtgtta aaccgttctc tgttgctccg    1560
accccgatcg ctcgtccggt tatcggtact ggcacccacc gtgaaaaacg tgctgtaggt    1620
ctgggtatgc tgttcctggg cgttctgtct gcagcaggtt ccactatggg tgctgcagct    1680
accgctctga ccgtacagac ccactctgtt atcaaaggta tcgtacagca gcaggacaac    1740
ctgctgcgtg caatccaggc acagcaggaa ctgctgcgtc tgtctgtatg gggtatccgt    1800
cagctgcgtg ctcgtctgct ggcactggaa accctgatcc agaaccagca gctgctgaac    1860
ctgtggggct gcaaaggtcg tctgatctgc tacacctccg ttaaatggaa cgaaacctgg    1920
cgtaacacca ccaacatcaa ccagatctgg ggtaacctga cctggcagga atgggaccag    1980
cagatcgaca acgtttcttc caccatctac gaagaaatcc agaaagctca ggttcagcag    2040
gaacagaacg aaaaaaaact gctggaactg gacgaatggg cttctctgtg gaactggctg    2100
gacatcacca aatggctgta atag                                           2124
```

<210> SEQ ID NO 93
<211> LENGTH: 706
<212> TYPE: PRT
<213> ORGANISM: Human Immunodeficiency Virus
<220> FEATURE:
<223> OTHER INFORMATION: Encodes recombinant protein pGO-13CKS

<400> SEQUENCE: 93

```
Met Ser Phe Val Val Ile Ile Pro Ala Arg Tyr Ala Ser Thr Arg Leu
  1               5                  10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
 50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
                 85                  90                  95

Val Gln Gly Asp Glu Pro Met Ile Pro Ala Thr Ile Ile Arg Gln Val
            100                 105                 110

Ala Asp Asn Leu Ala Gln Arg Gln Val Gly Met Ala Thr Leu Ala Val
        115                 120                 125

Pro Ile His Asn Ala Glu Glu Ala Phe Asn Pro Asn Ala Val Lys Val
    130                 135                 140

Val Leu Asp Ala Glu Gly Tyr Ala Leu Tyr Phe Ser Arg Ala Thr Ile
145                 150                 155                 160

Pro Trp Asp Arg Asp Arg Phe Ala Glu Gly Leu Glu Thr Val Gly Asp
                165                 170                 175

Asn Phe Leu Arg His Leu Gly Ile Tyr Gly Tyr Arg Ala Gly Phe Ile
            180                 185                 190

Arg Arg Tyr Val Asn Trp Gln Pro Ser Pro Leu Glu His Ile Glu Met
        195                 200                 205

Leu Glu Gln Leu Arg Val Leu Trp Tyr Gly Glu Lys Ile His Val Ala
    210                 215                 220

Val Ala Gln Glu Val Pro Gly Thr Gly Val Asp Thr Pro Glu Asp Pro
225                 230                 235                 240

Ser Thr Ala Leu Met Lys Ile Pro Gly Asp Pro Gly Gly Gly Asp Met
                245                 250                 255

Arg Asp Asn Trp Arg Ser Glu Leu Tyr Lys Tyr Lys Val Val Lys Ile
            260                 265                 270

Glu Pro Leu Gly Val Ala Pro Thr Lys Ala Lys Arg Arg Val Val Gln
        275                 280                 285

Arg Glu Lys Arg Ala Val Gly Ile Gly Ala Leu Phe Leu Gly Phe Leu
    290                 295                 300

Gly Ala Ala Gly Ser Thr Met Gly Ala Ala Ser Met Thr Leu Thr Val
305                 310                 315                 320

Gln Ala Arg Gln Leu Leu Ser Gly Ile Val Gln Gln Asn Asn Leu
                325                 330                 335

Leu Arg Ala Ile Glu Ala Gln Gln His Leu Leu Gln Leu Thr Val Trp
            340                 345                 350

Gly Ile Lys Gln Leu Gln Ala Arg Ile Leu Ala Val Glu Arg Tyr Leu
        355                 360                 365

Lys Asp Gln Gln Leu Leu Gly Ile Trp Gly Cys Ser Gly Lys Leu Ile
    370                 375                 380

Cys Thr Thr Ala Val Pro Trp Asn Ala Ser Trp Ser Asn Lys Ser Leu
385                 390                 395                 400
```

-continued

```
Glu Gln Ile Trp Asn Asn Met Thr Trp Met Glu Trp Asp Arg Glu Ile
                405                 410                 415

Asn Asn Tyr Thr Ser Leu Ile His Ser Leu Ile Glu Glu Ser Gln Asn
            420                 425                 430

Gln Gln Glu Lys Asn Glu Gln Glu Leu Leu Glu Leu Asp Lys Trp Val
        435                 440                 445

Asn Arg Val Arg Gln Gly Tyr Ser Pro Leu Ser Phe Gln Thr His Leu
    450                 455                 460

Pro Ile Pro Arg Gly Pro Asp Arg Pro Glu Gly Ile Glu Glu Glu Gly
465                 470                 475                 480

Gly Glu Arg Asp Arg Asp Arg Ser Ile Arg Leu Val Ile Gly Gly Asp
                485                 490                 495

Met Lys Asp Ile Trp Arg Asn Glu Leu Phe Lys Tyr Lys Val Val Arg
                500                 505                 510

Val Lys Pro Phe Ser Val Ala Pro Thr Pro Ile Ala Arg Pro Val Ile
            515                 520                 525

Gly Thr Gly Thr His Arg Glu Lys Arg Ala Val Gly Leu Gly Met Leu
        530                 535                 540

Phe Leu Gly Val Leu Ser Ala Ala Gly Ser Thr Met Gly Ala Ala Ala
545                 550                 555                 560

Thr Ala Leu Thr Val Gln Thr His Ser Val Ile Lys Gly Ile Val Gln
                565                 570                 575

Gln Gln Asp Asn Leu Leu Arg Ala Ile Gln Ala Gln Gln Glu Leu Leu
            580                 585                 590

Arg Leu Ser Val Trp Gly Ile Arg Gln Leu Arg Ala Arg Leu Leu Ala
        595                 600                 605

Leu Glu Thr Leu Ile Gln Asn Gln Gln Leu Leu Asn Leu Trp Gly Cys
    610                 615                 620

Lys Gly Arg Leu Ile Cys Tyr Thr Ser Val Lys Trp Asn Glu Thr Trp
625                 630                 635                 640

Arg Asn Thr Thr Asn Ile Asn Gln Ile Trp Gly Asn Leu Thr Trp Gln
                645                 650                 655

Glu Trp Asp Gln Gln Ile Asp Asn Val Ser Ser Thr Ile Tyr Glu Glu
            660                 665                 670

Ile Gln Lys Ala Gln Val Gln Gln Glu Gln Asn Glu Lys Lys Leu Leu
        675                 680                 685

Glu Leu Asp Glu Trp Ala Ser Leu Trp Asn Trp Leu Asp Ile Thr Lys
    690                 695                 700

Trp Leu
705

<210> SEQ ID NO 94
<211> LENGTH: 1470
<212> TYPE: DNA
<213> ORGANISM: Human Immunodeficiency Virus
<220> FEATURE:
<223> OTHER INFORMATION: Nucleotide sequence of the coding region of
      pGO-14pL

<400> SEQUENCE: 94
atgatcggtg gtgacatgaa agacatctgg cgtaacgaac tgttcaaata caaagttgtt      60
cgtgttaaac cgttctctgt tgctccgacc ccgatcgctc gtccggttat cggtactggc     120
acccaccgtg aaaaacgtgc tgtaggtctg ggtatgctgt tcctgggcgt tctgtctgca     180
gcaggttcca ctatgggtgc tgcagctacc gctctgaccg tacagaccca ctctgttatc     240
```

-continued

```
aaaggtatcg tacagcagca ggacaacctg ctgcgtgcaa tccaggcaca gcaggaactg        300
ctgcgtctgt ctgtatgggg tatccgtcag ctgcgtgctc gtctgctggc actggaaacc        360
ctgatccaga accagcagct gctgaacctg tggggctgca aggtcgtct gatctgctac         420 acctccgtta atggaacga aacctggcgt aacaccacca acatcaacca gatctggggt         480
aacctgacct ggcaggaatg ggaccagcag atcgacaacg tttcttccac catctacgaa        540
gaaatccaga aagctcaggt tcagcaggaa cagaacgaaa aaaaactgct ggaactggac        600
gaatgggctt ctctgtggaa ctggctggac atcaccaaat ggctgcgtaa catccgtcag        660
ggctaccagc cgctgtccct gcagatcccg acccgtcagc agtctgaagc tgaaactccg        720
ggtcgtaccg gtgaaggtcc gggtggtggt gacatgcgtg acaactggcg ttctgaactg        780
tacaaataca agttgttaa atcgaaccg ctgggtgttg ctccgactaa agctaaacgt          840
cgtgttgttc agcgtgaaaa acgcgccgtt ggtatcggtg cactgttcct gggtttcctg        900
ggtgctgctg gttctaccat gggtgctgct tctatgaccc tgactgttca ggcccgtcag        960
cttctgtctg gtatcgttca gcagcagaac aatctgctgc gtgctatcga agctcagcag       1020
catctgctgc aactgaccgt ttgggggtatc aaacagcttc aggctcgtat cctggctgtt      1080
gaacgttacc tgaaagacca gcagctgctg ggtatctggg gttgctctgg taaactgatc       1140
tgcactactg ctgttccgtg aacgcttct tggtctaaca atctctgga acagatctgg         1200 aacaacatga cttggatgga atgggaccgt gaaatcaaca actacacaag cttgatccac       1260
tctctgatcg aagaaagcca gaaccagcag gaaaaaaacg aacaggaact tctagaactg       1320
gacaaatggg ttaaccgtgt tcgtcagggt tactctccgc tgtctttcca gacccatctg       1380
ccgatcccgc gtggtccgga ccgtccggaa ggtatcgaag aagaaggcgg cgaacgtgac       1440
cgtgaccgtt ccattcgtct ggtataatag                                        1470
```

<210> SEQ ID NO 95
<211> LENGTH: 488
<212> TYPE: PRT
<213> ORGANISM: Human Immunodeficiency Virus
<220> FEATURE:
<223> OTHER INFORMATION: Encodes recombinant protein pGO-14PL

<400> SEQUENCE: 95

```
Met Ile Gly Gly Asp Met Lys Asp Ile Trp Arg Asn Glu Leu Phe Lys
 1               5                  10                  15

Tyr Lys Val Val Arg Val Lys Pro Phe Ser Val Ala Pro Thr Pro Ile
            20                  25                  30

Ala Arg Pro Val Ile Gly Thr Gly Thr His Arg Glu Lys Arg Ala Val
        35                  40                  45

Gly Leu Gly Met Leu Phe Leu Gly Val Leu Ser Ala Ala Gly Ser Thr
    50                  55                  60

Met Gly Ala Ala Ala Thr Ala Leu Thr Val Gln Thr His Ser Val Ile
65                  70                  75                  80

Lys Gly Ile Val Gln Gln Gln Asp Asn Leu Leu Arg Ala Ile Gln Ala
                85                  90                  95

Gln Gln Glu Leu Leu Arg Leu Ser Val Trp Gly Ile Arg Gln Leu Arg
            100                 105                 110

Ala Arg Leu Leu Ala Leu Glu Thr Leu Ile Gln Asn Gln Gln Leu Leu
        115                 120                 125

Asn Leu Trp Gly Cys Lys Gly Arg Leu Ile Cys Tyr Thr Ser Val Lys
    130                 135                 140
```

| | | | | | | | | | | | | |
|---|---|---|---|---|---|---|---|---|---|---|---|---|
| Trp | Asn | Glu | Thr | Trp | Arg | Asn | Thr | Thr | Asn | Ile | Asn | Gln | Ile | Trp | Gly |
| 145 | | | | 150 | | | | | 155 | | | | | 160 | |

Trp Asn Glu Thr Trp Arg Asn Thr Thr Asn Ile Asn Gln Ile Trp Gly
145                 150                 155                 160

Asn Leu Thr Trp Gln Glu Trp Asp Gln Gln Ile Asp Asn Val Ser Ser
            165                 170                 175

Thr Ile Tyr Glu Glu Ile Gln Lys Ala Gln Val Gln Gln Glu Gln Asn
            180                 185                 190

Glu Lys Lys Leu Leu Glu Leu Asp Glu Trp Ala Ser Leu Trp Asn Trp
                195                 200                 205

Leu Asp Ile Thr Lys Trp Leu Arg Asn Ile Arg Gln Gly Tyr Gln Pro
210                 215                 220

Leu Ser Leu Gln Ile Pro Thr Arg Gln Gln Ser Glu Ala Glu Thr Pro
225                 230                 235                 240

Gly Arg Thr Gly Glu Gly Pro Gly Gly Gly Asp Met Arg Asp Asn Trp
                245                 250                 255

Arg Ser Glu Leu Tyr Lys Tyr Lys Val Val Lys Ile Glu Pro Leu Gly
            260                 265                 270

Val Ala Pro Thr Lys Ala Lys Arg Arg Val Val Gln Arg Glu Lys Arg
            275                 280                 285

Ala Val Gly Ile Gly Ala Leu Phe Leu Gly Phe Leu Gly Ala Ala Gly
290                 295                 300

Ser Thr Met Gly Ala Ala Ser Met Thr Leu Thr Val Gln Ala Arg Gln
305                 310                 315                 320

Leu Leu Ser Gly Ile Val Gln Gln Gln Asn Asn Leu Leu Arg Ala Ile
                325                 330                 335

Glu Ala Gln Gln His Leu Leu Gln Leu Thr Val Trp Gly Ile Lys Gln
            340                 345                 350

Leu Gln Ala Arg Ile Leu Ala Val Glu Arg Tyr Leu Lys Asp Gln Gln
            355                 360                 365

Leu Leu Gly Ile Trp Gly Cys Ser Gly Lys Leu Ile Cys Thr Thr Ala
370                 375                 380

Val Pro Trp Asn Ala Ser Trp Ser Asn Lys Ser Leu Glu Gln Ile Trp
385                 390                 395                 400

Asn Asn Met Thr Trp Met Glu Trp Asp Arg Glu Ile Asn Asn Tyr Thr
                405                 410                 415

Ser Leu Ile His Ser Leu Ile Glu Glu Ser Gln Asn Gln Gln Glu Lys
            420                 425                 430

Asn Glu Gln Glu Leu Leu Glu Leu Asp Lys Trp Val Asn Arg Val Arg
            435                 440                 445

Gln Gly Tyr Ser Pro Leu Ser Phe Gln Thr His Leu Pro Ile Pro Arg
450                 455                 460

Gly Pro Asp Arg Pro Glu Gly Ile Glu Glu Glu Gly Gly Glu Arg Asp
465                 470                 475                 480

Arg Asp Arg Ser Ile Arg Leu Val
            485

<210> SEQ ID NO 96
<211> LENGTH: 1584
<212> TYPE: DNA
<213> ORGANISM: Human Immunodeficiency Virus
<220> FEATURE:
<223> OTHER INFORMATION: Nucleotide sequence of the coding region of
      pGO-15CKS

<400> SEQUENCE: 96
atgagttttg tggtcattat tcccgcgcgc tacgcgtcga cgcgtctgcc cggtaaacca    60

```
ttggttgata ttaacggcaa acccatgatt gttcatgttc ttgaacgcgc gcgtgaatca        120
ggtgccgagc gcatcatcgt ggcaaccgat catgaggatg ttgcccgcgc cgttgaagcc        180
gctggcggtg aagtatgtat gacgcgcgcc gatcatcagt caggaacaga acgtctggcg        240
gaagttgtcg aaaaatgcgc attcagcgac gacacggtga tcgttaatgt gcagggtgat        300
gaaccgatga tccctgcgac aatcattcgt caggttgctg ataacctcgc tcagcgtcag        360
gtgggtatga cgactctggc ggtgccaatc cacaatgcgg aagaagcgtt taacccgaat        420
gcggtgaaag tggttctcga cgctgaaggg tatgcactgt acttctctcg cgccaccatt        480
ccttgggatc gtgatcgttt tgcagaaggc cttgaaaccg ttggcgataa cttcctgcgt        540
catcttggta tttatggcta ccgtgcaggc tttatccgtc gttacgtcaa ctggcagcca        600
agtccgttag aacacatcga aatgttagag cagcttcgtg ttctgtggta cggcgaaaaa        660
atccatgttg ctgttgctca ggaagttcct ggcacaggtg tggatacccc tgaagatctc        720
gacccgtcga cgaattctat cggtggtgac atgaaagaca tctggcgtaa cgaactgttc        780
aaatacaaag ttgttcgtgt taaaccgttc tctgttgctc cgaccccgat cgctcgtccg        840
gttatcggta ctggcaccca ccgtgaaaaa cgtgctgtag gtctgggtat gctgttcctg        900
ggcgttctgt ctgcagcagg ttccactatg ggtgctgcag ctaccgctct gaccgtacag        960
acccactctg ttatcaaagg tatcgtacag cagcaggaca acctgctgcg tgcaatccag       1020
gcacagcagg aactgctgcg tctgtctgta tggggtatcc gtcagctgcg tgctcgtctg       1080
ctggcactgg aaaccctgat ccagaaccag cagctgctga acctgtgggg ctgcaaaggt       1140
cgtctgatct gctacacctc cgttaaatgg aacgaaacct ggcgtaacac caccaacatc       1200
aaccagatct ggggtaacct gacctggcag gaatgggacc agcagatcga caacgtttct       1260
tccaccatct acgaagaaat ccagaaagct caggttcagc aggaacagaa cgaaaaaaaa       1320
ctgctggaac tggacgaatg ggcttctctg tggaactggc tggacatcac caatggctg       1380 cgtaacatcc gtcagggcta ccagccgctg tccctgcaga tcccgacccg tcagcagtct       1440
gaagctgaaa ctccgggtcg taccggtgaa ggtggcggtt ctcgcctgct ggctctggaa       1500
actctgattc agaaccagca actgcttaac ctgtggggtt gcaagggccg cctgatttgc       1560
tacacttctg taaaatggta atag                                              1584
```

<210> SEQ ID NO 97
<211> LENGTH: 526
<212> TYPE: PRT
<213> ORGANISM: Human Immunodeficiency Virus
<220> FEATURE:
<223> OTHER INFORMATION: Encodes recombinant protein pGO-15CKS

<400> SEQUENCE: 97

```
Met Ser Phe Val Val Ile Ile Pro Ala Arg Tyr Ala Ser Thr Arg Leu
 1               5                  10                  15

Pro Gly Lys Pro Leu Val Asp Ile Asn Gly Lys Pro Met Ile Val His
             20                  25                  30

Val Leu Glu Arg Ala Arg Glu Ser Gly Ala Glu Arg Ile Ile Val Ala
         35                  40                  45

Thr Asp His Glu Asp Val Ala Arg Ala Val Glu Ala Ala Gly Gly Glu
     50                  55                  60

Val Cys Met Thr Arg Ala Asp His Gln Ser Gly Thr Glu Arg Leu Ala
 65                  70                  75                  80

Glu Val Val Glu Lys Cys Ala Phe Ser Asp Asp Thr Val Ile Val Asn
```

-continued

```
                85                  90                  95
Val Gln Gly Asp Glu Pro Met Ile Pro Ala Thr Ile Ile Arg Gln Val
                100                 105                 110
Ala Asp Asn Leu Ala Gln Arg Gln Val Gly Met Thr Thr Leu Ala Val
            115                 120                 125
Pro Ile His Asn Ala Glu Ala Phe Asn Pro Asn Ala Val Lys Val
        130                 135                 140
Val Leu Asp Ala Glu Gly Tyr Ala Leu Tyr Phe Ser Arg Ala Thr Ile
145                 150                 155                 160
Pro Trp Asp Arg Asp Arg Phe Ala Glu Gly Leu Glu Thr Val Gly Asp
                165                 170                 175
Asn Phe Leu Arg His Leu Gly Ile Tyr Gly Tyr Arg Ala Gly Phe Ile
                180                 185                 190
Arg Arg Tyr Val Asn Trp Gln Pro Ser Pro Leu Glu His Ile Glu Met
            195                 200                 205
Leu Glu Gln Leu Arg Val Leu Trp Tyr Gly Glu Lys Ile His Val Ala
        210                 215                 220
Val Ala Gln Glu Val Pro Gly Thr Gly Val Asp Thr Pro Glu Asp Leu
225                 230                 235                 240
Asp Pro Ser Thr Asn Ser Ile Gly Gly Asp Met Lys Asp Ile Trp Arg
                245                 250                 255
Asn Glu Leu Phe Lys Tyr Lys Val Val Arg Val Lys Pro Phe Ser Val
                260                 265                 270
Ala Pro Thr Pro Ile Ala Arg Pro Val Ile Gly Thr Gly Thr His Arg
            275                 280                 285
Glu Lys Arg Ala Val Gly Leu Gly Met Leu Phe Leu Gly Val Leu Ser
        290                 295                 300
Ala Ala Gly Ser Thr Met Gly Ala Ala Thr Ala Leu Thr Val Gln
305                 310                 315                 320
Thr His Ser Val Ile Lys Gly Ile Val Gln Gln Asp Asn Leu Leu
                325                 330                 335
Arg Ala Ile Gln Ala Gln Gln Glu Leu Leu Arg Leu Ser Val Trp Gly
            340                 345                 350
Ile Arg Gln Leu Arg Ala Arg Leu Leu Ala Leu Glu Thr Leu Ile Gln
        355                 360                 365
Asn Gln Gln Leu Leu Asn Leu Trp Gly Cys Lys Gly Arg Leu Ile Cys
    370                 375                 380
Tyr Thr Ser Val Lys Trp Asn Glu Thr Trp Arg Asn Thr Thr Asn Ile
385                 390                 395                 400
Asn Gln Ile Trp Gly Asn Leu Thr Trp Gln Glu Trp Asp Gln Ile
                405                 410                 415
Asp Asn Val Ser Ser Thr Ile Tyr Glu Glu Ile Gln Lys Ala Gln Val
            420                 425                 430
Gln Gln Glu Gln Asn Glu Lys Lys Leu Leu Glu Leu Asp Glu Trp Ala
        435                 440                 445
Ser Leu Trp Asn Trp Leu Asp Ile Thr Lys Trp Leu Arg Asn Ile Arg
    450                 455                 460
Gln Gly Tyr Gln Pro Leu Ser Leu Gln Ile Pro Thr Arg Gln Gln Ser
465                 470                 475                 480
Glu Ala Glu Thr Pro Gly Arg Thr Gly Glu Gly Gly Ser Arg Leu
                485                 490                 495
Leu Ala Leu Glu Thr Leu Ile Gln Asn Gln Gln Leu Leu Asn Leu Trp
                500                 505                 510
```

```
Gly Cys Lys Gly Arg Leu Ile Cys Tyr Thr Ser Val Lys Trp
        515                 520                 525
```

<210> SEQ ID NO 98
<211> LENGTH: 60
<212> TYPE: DNA
<213> ORGANISM: Human Immunodeficiency Virus
<220> FEATURE:
<223> OTHER INFORMATION: Synthetic oligonucleotide (pTB319+A)

<400> SEQUENCE: 98
gaccgtccgg aaggtatcga agaagaaggc ggcgaacgtg accgtgaccg ttccattcgt    60

<210> SEQ ID NO 99
<211> LENGTH: 53
<212> TYPE: DNA
<213> ORGANISM: Human Immunodeficiency Virus
<220> FEATURE:
<223> OTHER INFORMATION: Synthetic oligonucleotide (pTB319+B)

<400> SEQUENCE: 99
atggaacggt cacggtcacg ttcgccgcct tcttcttcga taccttccgg acg            53

<210> SEQ ID NO 100
<211> LENGTH: 20
<212> TYPE: DNA
<213> ORGANISM: Human Immunodeficiency Virus
<220> FEATURE:
<223> OTHER INFORMATION: Sequencing primer pTB-S4

<400> SEQUENCE: 100
atctctggaa cagatctgga                                                 20

<210> SEQ ID NO 101
<211> LENGTH: 20
<212> TYPE: DNA
<213> ORGANISM: Human Immunodeficiency Virus
<220> FEATURE:
<223> OTHER INFORMATION: Sequencing primer pTB-S7

<400> SEQUENCE: 101
agtactgaag cagattccac                                                 20

<210> SEQ ID NO 102
<211> LENGTH: 19
<212> TYPE: DNA
<213> ORGANISM: Human Immunodeficiency Virus
<220> FEATURE:
<223> OTHER INFORMATION: Sequencing primer pTB-S1

<400> SEQUENCE: 102
ccgtcgttac gtcaactgg                                                  19

<210> SEQ ID NO 103
<211> LENGTH: 18
<212> TYPE: DNA
<213> ORGANISM: Human Immunodeficiency Virus
<220> FEATURE:
<223> OTHER INFORMATION: Sequencing primer pTB-S2

<400> SEQUENCE: 103
cgccgttggt atcggtgc                                                   18

<210> SEQ ID NO 104
<211> LENGTH: 19

```
<210> SEQ ID NO 104
<211> LENGTH: 19
<212> TYPE: DNA
<213> ORGANISM: Human Immunodeficiency Virus
<220> FEATURE:
<223> OTHER INFORMATION: Sequencing primer pTB-S3

<400> SEQUENCE: 104
taccagacag aagctgacg                                              19

<210> SEQ ID NO 105
<211> LENGTH: 20
<212> TYPE: DNA
<213> ORGANISM: Human Immunodeficiency Virus
<220> FEATURE:
<223> OTHER INFORMATION: Sequencing primer pTB-S5

<400> SEQUENCE: 105
cttcgatcag agagtggatc                                             20

<210> SEQ ID NO 106
<211> LENGTH: 20
<212> TYPE: DNA
<213> ORGANISM: Human Immunodeficiency Virus
<220> FEATURE:
<223> OTHER INFORMATION: Sequencing primer pTB-S6

<400> SEQUENCE: 106
gacgatctgc gttctctgtg                                             20

<210> SEQ ID NO 107
<211> LENGTH: 1800
<212> TYPE: DNA
<213> ORGANISM: Human Immunodeficiency Virus
<220> FEATURE:
<223> OTHER INFORMATION: Nucleotide sequence of the coding region of
      pGM-1CKS

<400> SEQUENCE: 107
atgagttttg tggtcattat tcccgcgcgc tacgcgtcga cgcgtctgcc cggtaaacca     60
ttggttgata ttaacggcaa acccatgatt gttcatgttc ttaacgcgcg cgtgaatca    120 ggtgccgagc gcatcatcgt ggcaaccgat catgaggatg ttgcccgcgc cgttgaagcc   180
gctggcggtg aagtatgtat gacgcgcgcc gatcatcagt caggaacaga acgtctggcg   240
gaagttgtcg aaaaatgcgc attcagcgac gacacggtga tcgttaatgt gcagggtgat   300
gaaccgatga tccctgcgac aatcattcgt caggttgctg ataacctcgc tcagcgtcag   360
gtgggtatgg cgactctggc ggtgccaatc cacaatgcgc aagaagcgtt taacccgaat   420
gcggtgaaag tggttctcga cgctgaaggg tatgcactgt acttctctcg cgccaccatt   480
ccttgggatc gtgatcgttt tgcagaaggc cttgaaaccg ttggcgataa cttcctgcgt   540
catcttggta tttatggcta ccgtgcaggc tttatccgtc gttacgtcaa ctggcagcca   600
agtccgttag aacacatcga atgttagag cagcttcgtg ttctgtggta cggcgaaaaa   660
atccatgttg ctgttgctca ggaagttcct ggcacaggtg tggatacccc tgaagatccg   720
tcgacagccc ttatgaagat ccccggcgac ccgggtggtg gtgacatgcg tgacaactgg   780
cgttctgaac tgtacaaata caaagttgtt aaaatcgaac cgctgggtgt gctccgact   840 aaagctaaac gtcgtgttgt tcagcgtgaa aaacgcgccg ttggtatcgg tgcactgttc   900
ctgggtttcc tgggtgctgc tggttctacc atgggtgctg cttctatgac cctgactgtt   960
caggcccgtc agcttctgtc tggtatcgtt cagcagcaga caatctgct gcgtgctatc  1020 gaagctcagc agcatctgct gcaactgacc gtttggggta tcaaacagct tcaggctcgt  1080
```

-continued

```
atcctggctg ttgaacgtta cctgaaagac cagcagctgc tgggtatctg gggttgctct    1140
ggtaaactga tctgcactac tgctgttccg tggaacgctt cttggtctaa caaatctctg    1200
gaacagatct ggaacaacat gacttggatg aatgggacc gtgaaatcaa caactacaca     1260
agcttgatcc actctctgat cgaagaaagc cagaaccagc aggaaaaaaa cgaacaggaa    1320
cttctagaac tggacaaatg ggttaaccgt gttcgtcagg ttactctcc gctgtctttc     1380 cagacccatc tgccgatccc gcgtggtccg gaccgtccgg aaggtatcga agaagaaggc    1440
ggcgaacgtg accgtgaccg ttccattcgt ctggtaaacg ttctctggc tctgatctgg     1500 gacgatctgc gttctctgtg cctgttctct taccaccgtc tgcgtgatct gctgctgatc    1560
gtgactcgta tcgttgaact gctcggccgt cgtggttggg aagctctgaa atactggtgg    1620
aatctgcttc agtactggtc ccaggaactg aaaaactctg ctgtttctct gctgaacgct    1680
actgctatcg ctgttgctga aggcaccgat cgtgttatcg aagtagttca gggtgcttac    1740
cgtgctatcc gtcacattcc gcgtcgtatc cgtcagggtc tggaacgtat cctgctgtaa    1800
```

<210> SEQ ID NO 108
<211> LENGTH: 599
<212> TYPE: PRT
<213> ORGANISM: Human Immunodeficiency Virus
<220> FEATURE:
<223> OTHER INFORMATION: Encodes recombinant protein pGM-1CKS

<400> SEQUENCE: 108

```
Met Ser Phe Val Val Ile Ile Pro Ala Arg Tyr Ala Ser Thr Arg Leu
  1               5                  10                  15

Pro Gly Lys Pro Leu Val Asp Ile Asn Gly Lys P

-continued

Ser Thr Ala Leu Met Lys Ile Pro Gly Asp Pro Gly Gly Gly Asp Met
            245                 250                 255

Arg Asp Asn Trp Arg Ser Glu Leu Tyr Lys Tyr Lys Val Val Lys Ile
        260                 265                 270

Glu Pro Leu Gly Val Ala Pro Thr Lys Ala Lys Arg Arg Val Val Gln
    275                 280                 285

Arg Glu Lys Arg Ala Val Gly Ile Gly Ala Leu Phe Leu Gly Phe Leu
290                 295                 300

Gly Ala Ala Gly Ser Thr Met Gly Ala Ala Ser Met Thr Leu Thr Val
305                 310                 315                 320

Gln Ala Arg Gln Leu Leu Ser Gly Ile Val Gln Gln Gln Asn Asn Leu
                325                 330                 335

Leu Arg Ala Ile Glu Ala Gln Gln His Leu Leu Gln Leu Thr Val Trp
            340                 345                 350

Gly Ile Lys Gln Leu Gln Ala Arg Ile Leu Ala Val Glu Arg Tyr Leu
        355                 360                 365

Lys Asp Gln Gln Leu Leu Gly Ile Trp Gly Cys Ser Gly Lys Leu Ile
    370                 375                 380

Cys Thr Thr Ala Val Pro Trp Asn Ala Ser Trp Ser Asn Lys Ser Leu
385                 390                 395                 400

Glu Gln Ile Trp Asn Asn Met Thr Trp Met Glu Trp Asp Arg Glu Ile
                405                 410                 415

Asn Asn Tyr Thr Ser Leu Ile His Ser Leu Ile Glu Glu Ser Gln Asn
            420                 425                 430

Gln Gln Glu Lys Asn Glu Gln Glu Leu Leu Glu Leu Asp Lys Trp Val
        435                 440                 445

Asn Arg Val Arg Gln Gly Tyr Ser Pro Leu Ser Phe Gln Thr His Leu
    450                 455                 460

Pro Ile Pro Arg Gly Pro Asp Arg Pro Glu Gly Ile Glu Glu Glu Gly
465                 470                 475                 480

Gly Glu Arg Asp Arg Asp Arg Ser Ile Arg Leu Val Asn Gly Ser Leu
                485                 490                 495

Ala Leu Ile Trp Asp Asp Leu Arg Ser Leu Cys Leu Phe Ser Tyr His
            500                 505                 510

Arg Leu Arg Asp Leu Leu Leu Ile Val Thr Arg Ile Val Glu Leu Leu
        515                 520                 525

Gly Arg Arg Gly Trp Glu Ala Leu Lys Tyr Trp Trp Asn Leu Leu Gln
    530                 535                 540

Tyr Trp Ser Gln Glu Leu Lys Asn Ser Ala Val Ser Leu Leu Asn Ala
545                 550                 555                 560

Thr Ala Ile Ala Val Ala Glu Gly Thr Asp Arg Val Ile Glu Val Val
                565                 570                 575

Gln Gly Ala Tyr Arg Ala Ile Arg His Ile Pro Arg Arg Ile Arg Gln
            580                 585                 590

Gly Leu Glu Arg Ile Leu Leu
        595

<210> SEQ ID NO 109
<211> LENGTH: 47
<212> TYPE: DNA
<213> ORGANISM: Human Immunodeficiency Virus
<220> FEATURE:
<223> OTHER INFORMATION: PCR primer pTB/0-5'

<400> SEQUENCE: 109

```
gactacttgt agccattcgt ctggtaatcg gtggtgacat gaaagac         47
```

<210> SEQ ID NO 110
<211> LENGTH: 33
<212> TYPE: DNA
<213> ORGANISM: Human Immunodeficiency Virus
<220> FEATURE:
<223> OTHER INFORMATION: Sequencing primer pGO-9/Kpn

<400> SEQUENCE: 110

```
acaatgatgg tacctattat tcaccggtac gac                        33
```

<210> SEQ ID NO 111
<211> LENGTH: 18
<212> TYPE: DNA
<213> ORGANISM: Human Immunodeficiency Virus
<220> FEATURE:
<223> OTHER INFORMATION: Sequencing primer 3962

<400> SEQUENCE: 111

```
attggttgat attaacgg                                         18
```

<210> SEQ ID NO 112
<211> LENGTH: 20
<212> TYPE: DNA
<213> ORGANISM: Human Immunodeficiency Virus
<220> FEATURE:
<223> OTHER INFORMATION: Sequencing primer Sy120-S1

<400> SEQUENCE: 112

```
tcggtggtga catgaaagac                                       20
```

<210> SEQ ID NO 113
<211> LENGTH: 20
<212> TYPE: DNA
<213> ORGANISM: Human Immunodeficiency Virus
<220> FEATURE:
<223> OTHER INFORMATION: Sequencing primer 3965

<400> SEQUENCE: 113

```
aaaataggcg tatcacgagg                                       20
```

<210> SEQ ID NO 114
<211> LENGTH: 40
<212> TYPE: DNA
<213> ORGANISM: Human Immunodeficiency Virus
<220> FEATURE:
<223> OTHER INFORMATION: PCR primer pGO-8/Kpn

<400> SEQUENCE: 114

```
acaatgatgg tacctattac agccatttgg tgatgtccag                 40
```

<210> SEQ ID NO 115
<211> LENGTH: 46
<212> TYPE: DNA
<213> ORGANISM: Human Immunodeficiency Virus
<220> FEATURE:
<223> OTHER INFORMATION: PCR primer pTB/Age5'

<400> SEQUENCE: 115

```
taacgatcag ctaccggtga aggtccgggt ggtggtgaca tgcgtg          46
```

<210> SEQ ID NO 116
<211> LENGTH: 38
<212> TYPE: DNA

<213> ORGANISM: Human Immunodeficiency Virus
<220> FEATURE:
<223> OTHER INFORMATION: PCR primer pGO/B-3'

<400> SEQUENCE: 116
caagatggat cctattatac cagacgaatg gaacggtc                    38

<210> SEQ ID NO 117
<211> LENGTH: 122
<212> TYPE: DNA
<213> ORGANISM: Human Immunodeficiency Virus
<220> FEATURE:
<223> OTHER INFORMATION: Synthetic oligonucleotide (synIDR#2-A)

<400> SEQUENCE: 117
ccggtgaagg tggcggttct cgcctgctgg ctctggaaac tctgattcag aaccagcaac    60
tgcttaacct gtggggttgc aagggccgcc tgatttgcta cacttctgta aatggtaat   120 ag                                                                 122

<210> SEQ ID NO 118
<211> LENGTH: 122
<212> TYPE: DNA
<213> ORGANISM: Human Immunodeficiency Virus
<220> FEATURE:
<223> OTHER INFORMATION: Synthetic oligonucleotide (synIDR#2-B)

<400> SEQUENCE: 118
gatcctatta ccattttaca gaagtgtagc aaatcaggcg gcccttgcaa ccccacaggt    60
taagcagttg ctggttctga atcagagttt ccagagccag caggcgagaa ccgccacctt   120
ca                                                                 122

<210> SEQ ID NO 119
<211> LENGTH: 849
<212> TYPE: DNA
<213> ORGANISM: Human Immunodeficiency Virus
<220> FEATURE:
<223> OTHER INFORMATION: Nucleotide sequence of the coding region of
      pGO-15PL

<400> SEQUENCE: 119
atgatcggtg gtgacatgaa agacatctgg cgtaacgaac tgttcaaata caaagttgtt    60
cgtgttaaac cgttctctgt tgctccgacc ccgatcgctc gtccggttat cggtactggc   120
acccaccgtg aaaaacgtgc tgtaggtctg ggtatgctgt tcctgggcgt tctgtctgca   180
gcaggttcca ctatgggtgc tgcagctacc gctctgaccg tacagaccca ctctgttatc   240
aaaggtatcg tacagcagca ggacaacctg ctgcgtgcaa tccaggcaca gcaggaactg   300
ctgcgtctgt ctgtatgggg tatccgtcag ctgcgtgctc gtctgctggc actggaaacc   360
ctgatccaga accagcagct gctgaacctg tggggctgca aggtcgtct gatctgctac   420 acctccgtta atggaacga acctggcgt aacaccacca catcaacca gatctgggt   480 aacctgacct ggcaggaatg ggaccagcag atcgacaacg tttcttccac catctacgaa   540
gaaatccaga aagctcaggt tcagcaggaa cagaacgaaa aaaaactgct ggaactggac   600
gaatgggctt ctctgtggaa ctggctggac atcaccaaat ggctgcgtaa catccgtcag   660
ggctaccagc cgctgtccct gcagatcccg accgtcagc agtctgaagc tgaaactccg   720
ggtcgtaccg gtgaaggtgg cggttctcgc ctgctggctc tggaaactct gattcagaac   780
cagcaactgc ttaacctgtg gggttgcaag ggccgcctga tttgctacac ttctgtaaaa   840

-continued tggtaatag                                                                849

<210> SEQ ID NO 120
<211> LENGTH: 281
<212> TYPE: PRT
<213> ORGANISM: Human Immunodeficiency Virus
<220> FEATURE:
<223> OTHER INFORMATION: Encodes recombinant protein pGO-15PL

<400> SEQUENCE: 120

Met Ile Gly Gly Asp Met Lys Asp Ile Trp Arg Asn Glu Leu Phe Lys
 1               5                  10                  15

Tyr Lys Val Val Arg Val Lys Pro Phe Ser Val Ala Pro Thr Pro Ile
            20                  25                  30

Ala Arg Pro Val Ile Gly Thr Gly Thr His Arg Glu Lys Arg Ala Val
        35                  40                  45

Gly Leu Gly Met Leu Phe Leu Gly Val Leu Ser Ala Ala Gly Ser Thr
    50                  55                  60

Met Gly Ala Ala Ala Thr Ala Leu Thr Val Gln Thr His Ser Val Ile
65                  70                  75                  80

Lys Gly Ile Val Gln Gln Gln Asp Asn Leu Leu Arg Ala Ile Gln Ala
                85                  90                  95

Gln Gln Glu Leu Leu Arg Leu Ser Val Trp Gly Ile Arg Gln Leu Arg
            100                 105                 110

Ala Arg Leu Leu Ala Leu Glu Thr Leu Ile Gln Asn Gln Gln Leu Leu
        115                 120                 125

Asn Leu Trp Gly Cys Lys Gly Arg Leu Ile Cys Tyr Thr Ser Val Lys
130                 135                 140

Trp Asn Glu Thr Trp Arg Asn Thr Thr Asn Ile Asn Gln Ile Trp Gly
145                 150                 155                 160

Asn Leu Thr Trp Gln Glu Trp Asp Gln Gln Ile Asp Asn Val Ser Ser
                165                 170                 175

Thr Ile Tyr Glu Glu Ile Gln Lys Ala Gln Val Gln Gln Glu Gln Asn
            180                 185                 190

Glu Lys Lys Leu Leu Glu Leu Asp Glu Trp Ala Ser Leu Trp Asn Trp
        195                 200                 205

Leu Asp Ile Thr Lys Trp Leu Arg Asn Ile Arg Gln Gly Tyr Gln Pro
    210                 215                 220

Leu Ser Leu Gln Ile Pro Thr Arg Gln Gln Ser Glu Ala Glu Thr Pro
225                 230                 235                 240

Gly Arg Thr Gly Glu Gly Gly Gly Ser Arg Leu Leu Ala Leu Glu Thr
                245                 250                 255

Leu Ile Gln Asn Gln Gln Leu Leu Asn Leu Trp Gly Cys Lys Gly Arg
            260                 265                 270

Leu Ile Cys Tyr Thr Ser Val Lys Trp
        275                 280

<210> SEQ ID NO 121
<211> LENGTH: 22
<212> TYPE: DNA
<213> ORGANISM: Human Immunodeficiency Virus
<220> FEATURE:
<223> OTHER INFORMATION: PCR Primer 63168

<400> SEQUENCE: 121
acgttcgccg ccttcttctt cg                                                  22

What is claimed is:

1. An isolated antigen construct wherein said antigen construct comprises a fusion protein, said fusion protein comprising a first HIV-1 Group O gp120 polypeptide fused to a second HIV-1 Group O gp41 polypeptide, further wherein the first polypeptide comprises amino acid residues 476 through 520 of SEQ ID NO:61 and the second polypeptide comprises amino acid residues 47 through 245 of SEQ ID NO:48.

2. An isolated antigen construct wherein said antigen construct comprises a fusion protein, said fusion protein comprising a first HIV-1 Group O gp120 polypeptide comprising amino acid residues 476 through 520 of SEQ ID NO:61 fused to a second HIV-1 Group O gp41 polypeptide wherein the antigen construct is pGO-9PL.

3. The isolated antigen construct of claim 2, wherein the construct comprises the amino acid sequence of SEQ ID NO:48.

* * * * *

UNITED STATES PATENT AND TRADEMARK OFFICE
CERTIFICATE OF CORRECTION

PATENT NO. : 7,615,613 B2
APPLICATION NO. : 11/954351
DATED : November 10, 2009
INVENTOR(S) : John R. Hackett, Jr. et al.

It is certified that error appears in the above-identified patent and that said Letters Patent is hereby corrected as shown below:

On the Title page, Item (54) and Col. 1 lines 1-3
Title, "ANTIGEN CONSTRUCTS USEFUL IN THE DETECTION AND DIFFERENTIATION OF ANTIBODIES TO HIV" should read -- NOVEL ANTIGEN CONSTRUCTS USEFUL IN THE DETECTION AND DIFFERENTIATION OF ANTIBODIES TO HIV --.

Signed and Sealed this

Twelfth Day of October, 2010

David J. Kappos
*Director of the United States Patent and Trademark Office*